United States Patent
Duan et al.

(10) Patent No.: US 12,152,242 B2
(45) Date of Patent: Nov. 26, 2024

(54) CRISPR THERAPY

(71) Applicants: THE CURATORS OF THE UNIVERSITY OF MISSOURI, Columbia, MO (US); THE GOVERNMENT OF THE UNITED STATES OF AMERICA AS REPRESENTED BY THE SECRETARY OF THE DEPARTMENT OF HEALTH AND HUMAN SERVICES, NATIONAL INSTITUTES OF HEALTH, Rockville, MD (US)

(72) Inventors: Dongsheng Duan, Columbia, MO (US); Chady Hakim, Columbia, MO (US); Nalinda B. Wasala, Columbia, MO (US); Yongping Yue, Columbia, MO (US)

(73) Assignees: The Curators of the University of Missouri, Columbia, MO (US); The Government of the United States of America as Represented by the Secretary of the Department of Health and Human Services, Rockville, MD (US)

( * ) Notice: Subject to any disclaimer, the term of this patent is extended or adjusted under 35 U.S.C. 154(b) by 1016 days.

(21) Appl. No.: 17/049,980

(22) PCT Filed: Apr. 23, 2019

(86) PCT No.: PCT/US2019/028635
§ 371 (c)(1),
(2) Date: Oct. 23, 2020

(87) PCT Pub. No.: WO2019/209777
PCT Pub. Date: Oct. 31, 2019

(65) Prior Publication Data
US 2021/0163939 A1   Jun. 3, 2021

Related U.S. Application Data

(60) Provisional application No. 62/661,391, filed on Apr. 23, 2018.

(51) Int. Cl.
| | |
|---|---|
| *C12N 15/113* | (2010.01) |
| *C12N 9/22* | (2006.01) |
| *C12N 15/10* | (2006.01) |
| *C12N 15/86* | (2006.01) |

(52) U.S. Cl.
CPC ............ *C12N 15/113* (2013.01); *C12N 9/22* (2013.01); *C12N 15/102* (2013.01); *C12N 15/86* (2013.01); *C12N 2310/20* (2017.05); *C12N 2320/32* (2013.01); *C12N 2750/14141* (2013.01); *C12N 2830/008* (2013.01); *C12N 2830/50* (2013.01); *C12Y 301/00* (2013.01)

(58) Field of Classification Search
CPC ...... C12N 15/113; C12N 9/22; C12N 15/102; C12N 15/86; C12N 2310/20; C12N 2320/32; C12N 2750/14141; C12N 2830/008; C12N 2830/50; C12N 15/90; C12N 2750/14143; C07K 14/4707
See application file for complete search history.

(56) References Cited

U.S. PATENT DOCUMENTS

| | | | |
|---|---|---|---|
| 2016/0201089 A1 | 7/2016 | Gerbach et al. | |
| 2017/0204073 A1 | 7/2017 | Almstead et al. | |
| 2018/0010117 A1 | 1/2018 | Paschon | |
| 2018/0353615 A1 | 12/2018 | Gersbach et al. | |

FOREIGN PATENT DOCUMENTS

| | | |
|---|---|---|
| WO | 2016176191 A1 | 11/2016 |
| WO | 2017035416 A2 | 3/2017 |
| WO | 2017193029 A2 | 11/2017 |

OTHER PUBLICATIONS

Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10:8-9. (Year: 2002).*
Addgene; CRISPR Guide. Website Addgene, Jan. 12, 2018 [retrieved on Jun. 27, 2019]. Retrieved from the Internet: <www.addgene.org/crispr/guide/>; p. 4, paragraph 4.
Chew et al., A Multifunctional AAV-CRISPER-Cas9 and its host response; Nature Methods; Oct. 2016, vol. 13, No. 10, pp. 868-849.
Kouranova et al., Jun. 1, 2016, CRISPRs for Optimal Targeting; Deliver of CRISPR Components as DNA, RNA and Protein into Cultured Cells and Single-Cell Embryos; Human Gene Therapy, vol. 27, No. 6, p. 99 464-477.
Li et al., High Efficiency Targeting of Non-coding Sequences Using CRISPR/Cas9 System in Tilapia; Genes; Genomes/Genetics; 2019, vol. 9, pp. 287-295.
Liu et al., 2019, Chaper 2, Molecular Basis of Muscle Disease; Muscle Gene Therapy, 27-pages.

(Continued)

*Primary Examiner* — Iqbal H Chowdhury
(74) *Attorney, Agent, or Firm* — Sandberg Phoenix

(57) ABSTRACT

Disclosed herein are methods for systemically editing a gene in a subject and for systemically treating a genetic condition in a subject using a dual-vector CRISPR-Cas therapy. The methods comprise administering to the subject, via systemic administration, a gene editing AAV vector encoding a CRISPR effector protein (e.g., a Cas protein) and a targeting AAV vector providing one or more gRNAs targeted to the gene. In the methods, the ratio of the targeting AAV vector to the gene editing vector is greater than or equal to 2. Also provided are dual-vector systems for editing a gene or treating a genetic disease in a subject.

19 Claims, 45 Drawing Sheets

Specification includes a Sequence Listing.

(56) References Cited

OTHER PUBLICATIONS

Muller et al., *Streptococcus thermophilus* CRISPR-Cas9 Systems Enable Specific Editing of the Human Genome; The American Society of Gene & Cell Therapy; www.moleculartherapy.org vol. 24 No. 3, 636-644, Mar. 2016.

Nakayama et al., Simple and efficient CRISPR/Cas9-mediated targeted mutagenesis in Xenopus tropicalis; Genesis, Dec. 2013, vol. 51, No. 12, pp. 835-843.

Nelson et al., In vivo genome editing improves muscle function in a mouse model of Duchenne muscular dystrophy; Science; Jan. 22, 2016, vol. 351, No. 6271, pp. 403-408.

Nelson et al., In vivo genome editing improves muscle function in a mouse model of Duchenne muscular dystrophy; Science; Supplemental—published Dec. 31, 2015, pp. 1-30.

Robak et al., Excessive burden of lysosomal storage disorder gene variants in Parkinson's disease; Brain, 2017, vol. 40, pp. 3191-3203.

Senis et al., CRISPR/Cas9-mediated genome engineering: An adeno-associated viral (AAV) vector toolbox; Biotechnology Journal, 2014, vol. 9, pp. 1402-1412.

Swiech et al., In vivo interrogation of gene function in the mammalian brain using CRISPR-Cas9; Nature biotechnology; Jan. 2015, vol. 33, No. 1, pp. 102-106.

Yang et al., A dual AAV system enables the Cas9-mediated correction of a metabolic liver disease in newborn mice; Nature Biotechnology, Mar. 2016, vol. 3, No. 3, 334-338.

Yang et al., Feb. 1, 2016, Nature Biotechnology, 34, Supplemental, 13-pages.

\* cited by examiner

```
                        SEQUENCE LISTING

<160> NUMBER OF SEQ ID NOS: 29

<210> SEQ ID NO 1
<211> LENGTH: 21
<212> TYPE: DNA
<213> ORGANISM: Artificial Sequence
<220> FEATURE:
<223> OTHER INFORMATION: Synthetic construct

<400> SEQUENCE: 1
cgactgtgcc ttctagttgc c                                              21

<210> SEQ ID NO 2
<211> LENGTH: 24
<212> TYPE: DNA
<213> ORGANISM: Artificial Sequence
<220> FEATURE:
<223> OTHER INFORMATION: Synthetic construct

<400> SEQUENCE: 2
gacacctact cagacaatgc gatg                                           24

<210> SEQ ID NO 3
<211> LENGTH: 25
<212> TYPE: DNA
<213> ORGANISM: Artificial Sequence
<220> FEATURE:
<223> OTHER INFORMATION: Synthetic construct

<400> SEQUENCE: 3
agcaatagca tcacaaattt cacaa                                          25

<210> SEQ ID NO 4
<211> LENGTH: 29
<212> TYPE: DNA
<213> ORGANISM: Artificial Sequence
<220> FEATURE:
<223> OTHER INFORMATION: Synthetic construct

<400> SEQUENCE: 4
ccagacatga taagatacat tgatgagtt                                      29

<210> SEQ ID NO 5
<211> LENGTH: 25
<212> TYPE: DNA
<213> ORGANISM: Artificial Sequence
<220> FEATURE:
<223> OTHER INFORMATION: Synthetic construct

<400> SEQUENCE: 5
cgcacagaag atgatcaatg agatg                                          25
```

<210> SEQ ID NO 6
<211> LENGTH: 26
<212> TYPE: DNA
<213> ORGANISM: Artificial Sequence
<220> FEATURE:
<223> OTHER INFORMATION: Synthetic construct

<400> SEQUENCE: 6
ttcggataat ctcttcaatg cgttca                                          26

<210> SEQ ID NO 7
<211> LENGTH: 16
<212> TYPE: DNA
<213> ORGANISM: Artificial Sequence
<220> FEATURE:
<223> OTHER INFORMATION: Synthetic construct

<400> SEQUENCE: 7
ttggtctgcc ggtttc                                                     16

<210> SEQ ID NO 8
<211> LENGTH: 21
<212> TYPE: DNA
<213> ORGANISM: Artificial Sequence
<220> FEATURE:
<223> OTHER INFORMATION: Synthetic construct

<400> SEQUENCE: 8
gagcgcacca tcttcttcaa g                                               21

<210> SEQ ID NO 9
<211> LENGTH: 19
<212> TYPE: DNA
<213> ORGANISM: Artificial Sequence
<220> FEATURE:
<223> OTHER INFORMATION: Synthetic construct

<400> SEQUENCE: 9
tgtcgccctc gaacttcac                                                  19

<210> SEQ ID NO 10
<211> LENGTH: 15
<212> TYPE: DNA
<213> ORGANISM: Artificial Sequence
<220> FEATURE:
<223> OTHER INFORMATION: Synthetic construct

<400> SEQUENCE: 10
acgacggcaa ctaca                                                      15

<210> SEQ ID NO 11
<211> LENGTH: 30
<212> TYPE: DNA
<213> ORGANISM: Artificial Sequence
<220> FEATURE:
<223> OTHER INFORMATION: Synthetic construct

<400> SEQUENCE: 11
ctgaatatga aataatggag gagagactcg                                      30

<210> SEQ ID NO 12
<211> LENGTH: 26
<212> TYPE: DNA
<213> ORGANISM: Artificial Sequence
<220> FEATURE:

<223> OTHER INFORMATION: Synthetic construct

<400> SEQUENCE: 12
agttgaagcc attttgttgc tctttc                                              26

<210> SEQ ID NO 13
<211> LENGTH: 16
<212> TYPE: DNA
<213> ORGANISM: Artificial Sequence
<220> FEATURE:
<223> OTHER INFORMATION: Synthetic construct

<400> SEQUENCE: 13
cagagcctgt aatttc                                                         16

<210> SEQ ID NO 14
<211> LENGTH: 25
<212> TYPE: DNA
<213> ORGANISM: Artificial Sequence
<220> FEATURE:
<223> OTHER INFORMATION: Synthetic construct

<400> SEQUENCE: 14
aggagagact cgggaaatta cagaa                                               25

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
ggcaggccat tcctctttca                                                     20

<210> SEQ ID NO 16
<211> LENGTH: 16
<212> TYPE: DNA
<213> ORGANISM: Artificial Sequence
<220> FEATURE:
<223> OTHER INFORMATION: Synthetic construct

<400> SEQUENCE: 16
cagccatcca tttctg                                                         16

<210> SEQ ID NO 17
<211> LENGTH: 25
<212> TYPE: DNA
<213> ORGANISM: Artificial Sequence
<220> FEATURE:
<223> OTHER INFORMATION: Synthetic construct

<400> SEQUENCE: 17
gggatgctga atcctgaaa aaaca                                                25

<210> SEQ ID NO 18
<211> LENGTH: 26
<212> TYPE: DNA
<213> ORGANISM: Artificial Sequence
<220> FEATURE:
<223> OTHER INFORMATION: Synthetic construct

<400> SEQUENCE: 18
ttctgcccac cttcattaac actatt                                              26

<210> SEQ ID NO 19
<211> LENGTH: 19
<212> TYPE: DNA
<213> ORGANISM: Artificial Sequence
<220> FEATURE:
<223> OTHER INFORMATION: Synthetic construct

<400> SEQUENCE: 19
tcaaacaatg cagactttt                                          19

<210> SEQ ID NO 20
<211> LENGTH: 60
<212> TYPE: DNA
<213> ORGANISM: Artificial Sequence
<220> FEATURE:
<223> OTHER INFORMATION: Synthetic construct

<400> SEQUENCE: 20
tcgtcggcag cgtcagatgt gtataagaga cagtttctgt ctaaatataa tatgccctgt    60

<210> SEQ ID NO 21
<211> LENGTH: 59
<212> TYPE: DNA
<213> ORGANISM: Artificial Sequence
<220> FEATURE:
<223> OTHER INFORMATION: Synthetic construct

<400> SEQUENCE: 21
gtctcgtggg ctcggagatg tgtataagag acaggcagag cctcaaaatt aaatagaag     59

<210> SEQ ID NO 22
<211> LENGTH: 54
<212> TYPE: DNA
<213> ORGANISM: Artificial Sequence
<220> FEATURE:
<223> OTHER INFORMATION: Synthetic construct

<400> SEQUENCE: 22
tcgtcggcag cgtcagatgt gtataagaga caggagctca tcctctttca tgct          54

<210> SEQ ID NO 23
<211> LENGTH: 54
<212> TYPE: DNA
<213> ORGANISM: Artificial Sequence
<220> FEATURE:
<223> OTHER INFORMATION: Synthetic construct

<400> SEQUENCE: 23
gtctcgtggg ctcggagatg tgtataagag acaggaagga ggaacaggca ggag           54

<210> SEQ ID NO 24
<211> LENGTH: 56
<212> TYPE: DNA
<213> ORGANISM: Artificial Sequence
<220> FEATURE:
<223> OTHER INFORMATION: Synthetic construct

<400> SEQUENCE: 24
tcgtcggcag cgtcagatgt gtataagaga cagaaagttg ttagagcctg ctcatt         56

<210> SEQ ID NO 25
<211> LENGTH: 57
<212> TYPE: DNA
<213> ORGANISM: Artificial Sequence
<220> FEATURE:
<223> OTHER INFORMATION: Synthetic construct

```
<400> SEQUENCE: 25
gtctcgtggg ctcggagatg tgtataagag acagtttagt agacggaaga aagctca       57

<210> SEQ ID NO 26
<211> LENGTH: 53
<212> TYPE: DNA
<213> ORGANISM: Artificial Sequence
<220> FEATURE:
<223> OTHER INFORMATION: Synthetic construct

<400> SEQUENCE: 26
tcgtcggcag cgtcagatgt gtataagaga cagtggatat cctcctggga atg           53

<210> SEQ ID NO 27
<211> LENGTH: 54
<212> TYPE: DNA
<213> ORGANISM: Artificial Sequence
<220> FEATURE:
<223> OTHER INFORMATION: Synthetic construct

<400> SEQUENCE: 27
gtctcgtggg ctcggagatg tgtataagag acaggcctca actggaaact gagc          54

<210> SEQ ID NO 28
<211> LENGTH: 43
<212> TYPE: DNA
<213> ORGANISM: Artificial Sequence
<220> FEATURE:
<223> OTHER INFORMATION: Synthetic construct

<400> SEQUENCE: 28
aatgatacgg cgaccaccga gatctacact cgtcggcagc gtc                      43

<210> SEQ ID NO 29
<211> LENGTH: 45
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (25)..(30)
<223> OTHER INFORMATION: n is a, c, g, or t

<400> SEQUENCE: 29
caagcagaag acggcatacg agatnnnnnn gtctcgtggg ctcgg                    45
```

CRISPR THERAPY

CROSS-REFERENCE TO RELATED APPLICATIONS

This application is based on and claims priority to U.S. Provisional Application Ser. No. 62/661,391 filed on Apr. 23, 2018, which is incorporated herein by reference in its entirety.

This invention was made with government support under W81XWH-16-1-0221 awarded by the Medical Research and Development Command, and AR069085 awarded by the National Institutes of Health. The government has certain rights in the invention.

REFERENCE TO SEQUENCE LISTING SUBMITTED ELECTRONICALLY

The official copy of the sequence listing is submitted electronically as an ASCII-formatted sequence listing with a file named "0800528.0157 gene seq listing (.txt).TXT" created on Apr. 22, 2019, and having a size of 6.0 kilobytes, filed concurrently with the specification. The sequence listing contained in this ASCII-formatted document is part of the specification and is herein incorporated by reference in its entirety.

FIELD OF THE INVENTION

The present invention relates to improved methods for systemically editing a gene in a subject using CRISPR therapy. The methods can be used to treat and ameliorate a genetic disorder or condition. Also provided are dual-vector systems that can be used to systemically edit a gene in a subject.

BACKGROUND OF THE INVENTION

CRISPR/Cas-based gene editing systems can be used to introduce site-specific double stranded breaks at targeted genomic loci. This DNA cleavage stimulates the natural DNA-repair machinery, leading to one of two possible repair pathways. In the absence of a donor template, the break will be repaired by non-homologous end-joining (NHEJ), an error prone repair pathway that leads to small insertions or deletions of DNA. This method can be used to intentionally disrupt, delete, or alter the reading frame of targeted gene sequences. However, if a donor template is provided along with the nucleases, then the cellular machinery will repair the break by homologous recombination, which is enhanced several orders of magnitude in the presence of DNA cleavage. This method can be used to introduce specific changes in the DNA sequence at target sites. Engineered nucleases have been used for gene editing in a variety of human stem cells and cell lines, for gene editing in the mouse liver and in a localized fashion in vivo. However, the major hurdle for implementation of these technologies is that they haven't demonstrated that it is possible to deliver a gene editing system, systemically and continuously so that a therapeutic protein may be restored over an extended period throughout a subject. This is particularly important in therapies to treat disorders characterized by a widespread loss of a gene in an individual.

Hereditary genetic diseases have devastating effects on children in the United States. These diseases currently have no cure and can only be managed by attempts to alleviate the symptoms. For decades, the field of gene therapy has promised a cure for these disease. However, technical hurdles regarding the safe and efficient delivery of therapeutic genes to cells and patients have limited this approach. Duchenne Muscular Dystrophy (DMD) is the most common hereditary monogenetic disease and occurs in 1 in 3500 males. Dystrophin is a key component of a protein complex that is responsible for regulating muscle cell integrity and function. DMD patients typically lose the ability to physically support themselves during childhood, become progressively weaker during the teenage years, and die in their twenties. DMD is the result of inherited or spontaneous mutations in the dystrophin gene that results in the loss of functional dystrophin. Most mutations causing DMD are a result of deletions of exon(s), pushing the translational reading frame out of frame. Current experimental gene therapy strategies for DMD require repeated administration of transient gene delivery vehicles or rely on permanent integration of foreign genetic material into the genomic DNA. Both of these methods have serious safety concerns. Furthermore, these strategies have been limited by an inability to deliver the large and complex dystrophin gene sequence.

Recent studies suggest that delivery of CRISPR gene editing tools by adeno-associated virus (AAV) can reframe the mutated dystrophin gene and restore dystrophin expression in DMD patient cells in vitro and in short-term mouse studies in vivo. At the same time, since DMD is a chronic disease, a desirable therapy would require persistent, lifelong, dystrophin restoration and disease amelioration. No methods have been developed for one-time systemic AAV CRISPR therapy that can lead to long-term dystrophin restoration and disease amelioration. Therefore, a need exists for a systemic AAV therapy that can restore the reading frame of a mutated gene and thus overcome loss of expression mutations in various genetic disorders. The suitable therapy would lead to widespread restoration in gene expression and protein function.

BRIEF SUMMARY OF THE INVENTION

Provided herein are methods for systemically editing a gene in a subject, the methods comprising co-administering to the subject via systemic delivery: a gene editing AAV vector comprising a Cas gene under control of regulatory sequences which direct its expression in a target cell of the subject; and a targeting AAV vector providing at least one guide ribonucleic acid (gRNA) targeted to the gene; wherein the ratio of the targeting AAV vector to the gene editing AAV vector is greater than or equal to about 2:1 and wherein administering the mixture of the gene editing AAV and targeting AAV vector edits the gene by inducing a double stranded break (DSB) in the gene that is repaired using non-homologous end joining (NHEJ).

Also provided are methods for systemically treating a genetic disorder in a subject, the methods comprising administering to the subject via systemic delivery a gene editing AAV vector comprising a Cas gene under control of regulatory sequences which direct its expression in a target cell of the subject; and a targeting AAV vector comprising at least one gRNA, wherein the gRNAs target a gene comprising a mutation causing the genetic disorder in the subject; and wherein the ratio of the targeting AAV vector to the gene editing AAV vector is greater than or equal to about 2:1; and inducing a double stranded break (DSB) in the target gene that is repaired using non-homologous end joining (NHEJ).

Also provided is a dual vector system for systemically editing a gene in a subject, the system comprising: a gene editing AAV vector comprising a Cas gene under control of regulatory sequences which direct its expression in a cell of the subject; and a targeting AAV vector providing at least one gRNA, wherein the gRNA targets the gene; and wherein the ratio of the targeting AAV vector to the gene editing AAV vector is greater than or equal to about 2:1, and wherein the system induces at least one double stranded break in the gene that is repaired using non-homologous end joining (NHEJ).

Other objects and features will be in part apparent and in part pointed out hereinafter.

BRIEF DESCRIPTION OF THE SEVERAL VIEWS OF THE DRAWINGS

Corresponding reference characters indicate corresponding parts throughout the drawings.

DETAILED DESCRIPTION OF THE INVENTION

Figure 1A:
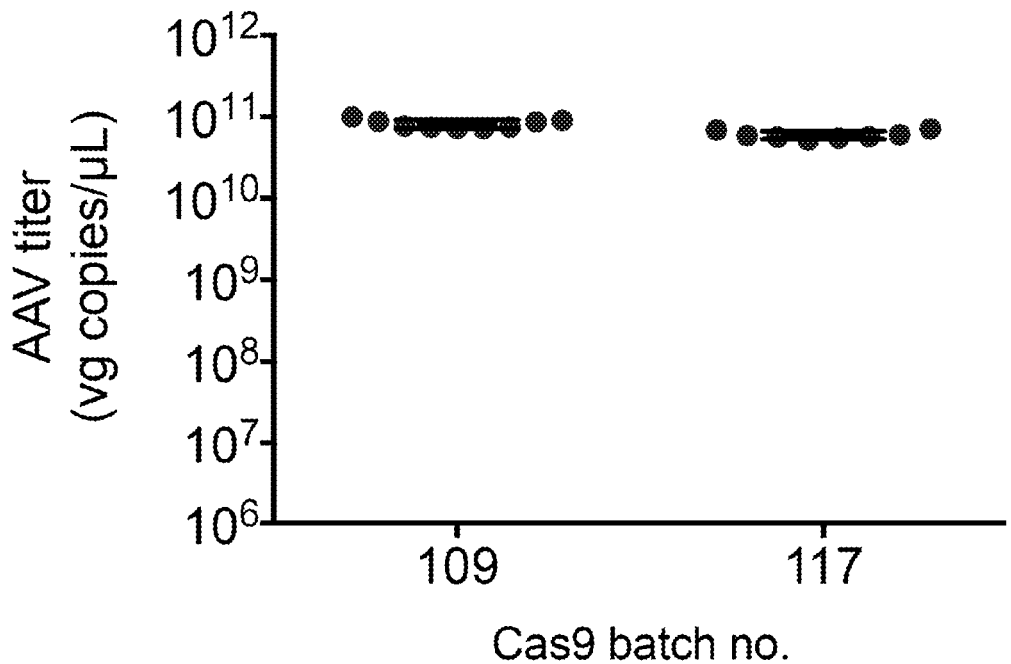
FIG. 1A depicts a scatter plot with individual AAV titer values (viral genome (vg) copies/µg) generated from different samples taken from two Cas9 batches prepared.

Provided herein are methods for systemically editing a gene in a subject or for systemically treating a genetic disorder in a subject using a dual-vector CRISPR-Cas gene editing system. Also provided are dual-vector systems for editing a gene. The methods provided herein use a dual-vector approach to systemically deliver a gene editing adeno-associated virus (AAV) and a targeting AAV vector to a subject. The methods described herein advantageously describe how to systemically administer a CRISPR-Cas system to a subject, thus allowing for widespread expression of a protein product. Importantly, the system described herein addresses a heretofore unknown problem with systemic administration of two vectors in which the targeting vector providing for a targeting RNA sequence (e.g., the gRNA) can be selectively degraded in vivo which results in a failure of gene editing in the targeted cells of the subject. To overcome this, the methods described herein employ a specific ratio of the targeting AAV vector to the gene editing AAV vector.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and material similar or equivalent to those described herein can be used in practice or testing of the present invention. All publications, patent applications, patents and other references mentioned herein are incorporated by reference in their entirety. The materials, methods and examples disclosed herein are illustrative only and not intended to be limiting.

"Adeno-associated virus" or "AAV" as used interchangeably herein refers to a small virus belonging to the genus Dependovirus of the Parvoviridae family that infects humans and some other primate species. AAV is not currently known to cause disease and consequently the virus causes a very mild immune response.

"Binding region" as used herein refers to the region within a nuclease target region that is recognized and bound by the nuclease.

"Cardiac muscle" or "heart muscle" as used interchangeably herein means a type of involuntary striated muscle found in the walls and histological foundation of the heart, the myocardium. Cardiac muscle is made of cardiomyocytes or myocardiocytes. Myocardiocytes show striations similar to those on skeletal muscle cells but contain only one, unique nucleus, unlike the multinucleated skeletal cells. In certain embodiments, "cardiac muscle condition" refers to a condition related to the cardiac muscle, such as cardiomyopathy, heart failure, arrhythmia, and inflammatory heart disease.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimized.

"Complement" or "complementary" as used herein can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Correcting", "genome editing" and "restoring" as used herein refers to changing a mutant gene that encodes a truncated protein or no protein at all, such that a full-length functional or partially full-length functional protein expression is obtained. Correcting or restoring a mutant gene may include repairing a frameshift mutation that causes a premature stop codon, an aberrant splice acceptor site or an aberrant splice donor site, by generating a double stranded break in the gene that is then repaired using non-homologous end joining (NHEJ). NHEJ may add or delete at least one base pair during repair which may restore the proper reading frame and eliminate the premature stop codon. Correcting or restoring a mutant gene may also include disrupting an aberrant splice acceptor site or splice donor sequence. Correcting or restoring a mutant gene may also include deleting a non-essential gene segment by the simultaneous action of two nucleases on the same DNA strand in order to restore the proper reading frame by removing the DNA between the two nuclease target sites and repairing the DNA break by NHEJ.

"Donor DNA", "donor template" and "repair template" as used interchangeably herein refers to a double-stranded DNA fragment or molecule that includes at least a portion of the gene of interest. The donor DNA may encode a full-functional protein or a partially-functional protein. As is understood in the art, a donor DNA is used to facilitate homologous recombination (HR). Preferably, the methods and constructs described herein do not comprise a donor DNA, donor template or a repair template.

"Duchenne muscular dystrophy" or "DMD" as used interchangeably herein refers to a recessive, fatal, X-linked disorder that results in muscle degeneration and eventual death. DMD is a common hereditary monogenic disease and occurs in 1 in 3500 males. DMD is the result of inherited or spontaneous mutations that cause nonsense or frame shift mutations in the dystrophin gene. The majority of dystrophin mutations that cause DMD are deletions of exons that disrupt the reading frame and cause premature translation termination in the dystrophin gene. DMD patients typically lose the ability to physically support themselves during childhood, become progressively weaker during the teenage years, and die in their twenties.

"Dystrophin" as used herein refers to a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane that is responsible for regulating muscle cell integrity and function. The dystrophin gene or "DMD gene" as used interchangeably herein is 2.2 megabases at locus Xp21. The primary transcription measures about 2,400 kb with the mature mRNA being about 14 kb. 79 exons code for the protein which is over 3500 amino acids.

"Exon 51" as used herein refers to the 51st exon of the dystrophin gene. Exon 51 is frequently adjacent to frame-disrupting deletions in DMD patients and has been targeted in clinical trials for oligonucleotide-based exon skipping. A clinical trial for the exon 51 skipping compound eteplirsen recently reported a significant functional benefit across 48 weeks, with an average of 47% dystrophin positive fibers compared to baseline. Mutations in exon 51 are ideally suited for permanent correction by NHEJ-based genome editing.

"Frameshift" or "frameshift mutation" as used interchangeably herein refers to a type of gene mutation wherein the addition or deletion of one or more nucleotides causes a shift in the reading frame of the codons in the mRNA. The shift in reading frame may lead to the alteration in the amino acid sequence at protein translation, such as a missense mutation or a premature stop codon.

"Functional" and "full-functional" as used herein describes protein that has biological activity. A "functional gene" refers to a gene transcribed to mRNA, which is translated to a functional protein.

"Fusion protein" as used herein refers to a chimeric protein created through the joining of two or more genes that originally coded for separate proteins. The translation of the fusion gene results in a single polypeptide with functional properties derived from each of the original proteins.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genetic disease" as used herein refers to a disease, partially or completely, directly or indirectly, caused by one or more abnormalities in the genome, especially a condition that is present from birth. The abnormality may be a mutation, an insertion or a deletion. The abnormality may affect the coding sequence of the gene or its regulatory sequence. The genetic disease may be selected from the group consisting of an inherited muscle disease (e.g., congenital myopathy or a muscular dystrophy), a lysosomal storage disease, a heritable disorder of connective tissue, a neurodegenerative disorder, and a skeletal dysplasia. For example, the genetic disease may be, but is not limited to, Duchenne muscular dystrophy (DMD), Becker's muscular dystrophy, Lamb-girdle muscular dystrophy, dysferlinopathy, dystroglycanopathy, aspartylglucosaminuria, Batten disease, cystinosis, Fabry disease, Gaucher disease, Pompe disease, Tay Sachs disease, Sandhoff disease, metachromatic leukodystrophy, mucolipidosis, mucopolysaccharide storage diseases, Niemann-Pick disease, Schindler disease, Krabbe disease, Ehlers-Danlos syndrome, epidermolysis bullosa, Marfan syndrome, neurofibromatosis, spinal muscular atrophy, amyotrophic lateral sclerosis, progressive muscular atrophy, fragile X syndrome, Charcot-Marie-Tooth disease, osteogenesis imperfecta, achondroplasia, or osteopetrosis. Other genetic diseases include hemophilia, cystic fibrosis, Huntington's chorea, familial hypercholesterolemia (LDL receptor defect), hepatoblastoma, Wilson's disease, congenital hepatic *porphyria*, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, and Tay-Sachs disease.

"Homology-directed repair" or "HDR", as used interchangeably herein refers to a mechanism in cells to repair double strand DNA lesions when a homologous piece of DNA is present in the nucleus, mostly in G2 and S phase of the cell cycle. HDR uses a donor DNA template to guide repair and may be used to create specific sequence changes to the genome, including the targeted addition of whole genes. If a donor template is provided along with the CRISPR/Cas9-based gene editing system, then the cellular machinery will repair the break by homologous recombination, which is enhanced several orders of magnitude in the presence of DNA cleavage. When the homologous DNA piece is absent, non-homologous end joining may take place instead.

"Genome editing" as used herein refers to changing a gene. Genome editing may include correcting or restoring a mutant gene. Genome editing may include knocking out a gene, such as a mutant gene or a normal gene. Genome editing may be used to treat disease or enhance muscle repair by changing the gene of interest.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Mutant gene" or "mutated gene" as used interchangeably herein refers to a gene that has undergone a detectable mutation. A mutant gene has undergone a change, such as the loss, gain, or exchange of genetic material, which affects the normal transmission and expression of the gene. A "disrupted gene" as used herein refers to a mutant gene that has a mutation that causes a premature stop codon. The disrupted gene product is truncated relative to a full-length undisrupted gene product.

"Non-homologous end joining (NHEJ) pathway" as used herein refers to a pathway that repairs double-strand breaks in DNA by directly ligating the break ends without the need for a homologous template. The template-independent re-ligation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called microhomologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible.

"Normal gene" as used herein refers to a gene that has not undergone a change, such as a loss, gain, or exchange of genetic material. The normal gene undergoes normal gene transmission and gene expression.

"Nuclease mediated NHEJ" as used herein refers to NHEJ that is initiated after a nuclease, such as a Cas molecule, cuts double stranded DNA.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Partially functional" as used herein describes a protein that is encoded by a mutant gene and has less biological activity than a functional protein but more than a nonfunctional protein.

"Premature stop codon" or "out of frame stop codon" used interchangeably herein refers to nonsense mutation in a sequence of DNA, which results in a stop codon at location not normally found in the wild-type gene. A premature stop codon may cause a protein to be truncated or shorter compared to the full-length version of the protein.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter, human U6 (hU6) promoter, and CMV IE promoter.

"Skeletal muscle" as used herein refers to a type of striated muscle, which is under the control of the somatic nervous system and attached to bones by bundles of collagen fibers known as tendons. Skeletal muscle is made up of individual components known as myocytes, or "muscle cells", sometimes colloquially called "muscle fibers." Myocytes are formed from the fusion of developmental myoblasts (a type of embryonic progenitor cell that gives rise to a muscle cell) in a process known as myogenesis. These long, cylindrical, multinucleated cells are also called myofibers. Skeletal muscle can include the gastrocnemius or the quadriceps.

"Skeletal muscle condition" as used herein refers to a condition related to the skeletal muscle, such as muscular dystrophies, aging, muscle degeneration, wound healing, and muscle weakness or atrophy.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Target gene" as used herein refers to any nucleotide sequence encoding a known or putative gene product. The target gene may be a mutated gene involved in a genetic disease. In certain embodiments, the target gene is a human dystrophin gene. In certain embodiments, the target gene is a mutant human dystrophin gene.

"Target region" as used herein refers to the region of the target gene to which the CRISPR/Cas-based gene editing system is designed to bind and cleave.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. Most preferably, the vector is an AAV vector. The vector may encode a Cas protein or at least one gRNA molecule. Suitable transcripts encoding a Cas protein (e.g., Cas9) or gRNA are described in US 2016/0201089, US2018/0353614 and WO2017/193029, hereby incorporated by reference.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

I. Methods of Systemically Editing a Gene in a Subject Using Dual-Vector System

Provided herein are methods for inducing edits in a gene of interest, the methods comprising administering to a subject, via systemic administration, a mixture of two AAV vectors (e.g., gene editing vector and targeting vector) described herein below. As described below, the gene editing vector contains a nucleic acid encoding a preferred Cas protein, and associated regulatory regions that enable its expression in vivo (i.e., in the subject). The targeting vector includes the gRNAs or a coding sequence that when transcribed in a cell will generate the gRNAs. When delivered systemically, the two vectors will be taken up into cells and expressed. Once inside the cell, the Cas protein and gRNAs (herein after referred to as the "CRISPR system") induce a double stranded break which is subsequently repaired using non-homologous end joining (NHEJ).

Restoration of protein expression from an endogenous mutated gene may preferably be through template-free NHEJ mediated DNA repair. In contrast to a transient method targeting the target gene RNA, the correction of the target gene reading frame in the genome by a transiently expressed CRISPR/Cas9 based gene editing system may lead to permanently restored target gene expression by each modified cell and all of its progeny. In certain embodiments, NHEJ is a nuclease mediated NHEJ, which in certain embodiments refers to NHEJ that is initiated when a Cas molecule (e.g., Cas9 or Cas12) cuts double stranded DNA.

Nuclease mediated NHEJ gene correction may correct the mutated gene target and offers several potential advantages over the homologous recombination (HR) pathway. For example, NHEJ does not require a donor template, which may cause non-specific insertional mutagenesis. In contrast to HR, NHEJ operates efficiently in all stages of the cell cycle and therefore may be effectively exploited in both cycling and post-mitotic cells, such as muscle fibers. This provides a robust, permanent gene restoration alternative to oligonucleotide-based exon skipping or pharmacologic forced read-through of stop codons and could theoretically require as few as one drug treatment.

The dual vector system comprises one vector expressing a Cas nuclease (e.g., a Cas9 or Cas12 nuclease) and a second vector providing one or more gRNA. The gRNAs direct the Cas protein to the gene target. The one or more gRNAs can target at least one of an exon, an intron, a promoter region, an enhancer region or a transcribed region of the target gene. The target regions can be chosen immediately upstream of possible out-of-frame stop codons such that insertions or deletions during the repair process restore the reading frame of the target gene by frame conversion. Target regions can also be splice acceptor sites or splice donor sites, such that insertions or deletions during the repair process disrupt splicing and restore the reading frame of the gene by splice site disruption and exon exclusion. Target regions can also be aberrant stop codons such that insertions or deletions during the repair process restore the reading frame of the gene by eliminating or disrupting the stop codon.

In various embodiments, the target gene may comprise a frameshift mutation that results in a loss of an open reading frame. In editing the gene, according to the methods described herein, the open reading frame may be restored. The mutation can result in a premature stop codon and the system can delete a portion of the target gene comprising the premature stop codon (e.g., an exon). Alternatively or in addition, the mutation can result in alternative splicing of the gene and the system induces an insertion or deletion in the gene to restore normal splicing of the gene. For example, the system can modify the gene in at least one of: a splicing signal, an exonic splicing enhancer/silencer (ESE/ESS), or an intronic splicing enhancer/silencer (ISE/ISS). In all methods described herein, the dual-vector CRISPR system does not comprise a donor sequence. Therefore, the methods described herein are designed to induce non-homologous end joining The dual vector system described herein may be used to correct or modify systemically any gene in a subject. In various embodiments, the system comprises two gRNAs, each targeting two different nucleic acid targets in the gene of interest. When two gRNAs are used in this way, they can induce a deletion in the gene corresponding to the distance between the two PAM regions for the gRNAs.

It has been discovered that the ratio of the gene editing vector to the targeting vector in the dual-vector system described herein must be carefully considered in view of the mode of administration of the system. Earlier work has shown successful genetic editing when a 1:1 ratio of the gene editing vector and the targeting vector is administered locally (e.g., intramuscularly) (e.g., see Nelson et al., "In vivo genome editing improves muscle function in a mouse model of Duchenne muscular dystrophy" *Science.* 2015 351(6271): 403-407, incorporated herein by reference in its entirety). However, the inventors have made the surprising discovery that using this ratio in systemic administration fails to achieve the desired result. Instead, systemic administration appears to result in selective degradation of the targeting vector providing the gRNA over the gene editing vector delivering the Cas gene. Thus, to achieve suitable genetic editing with systemic administration, the ratio of the gene editing vector to the targeting vector is suitably chosen so that there is an excess of the targeting vector (i.e., the gRNA) to the gene editing vector (i.e., the Cas gene). Preferably, the ratio of the targeting vector to the gene editing vector is greater than or equal to 2:1. For example, the ratio of the targeting vector to the gene editing vector can be from about 2:1 to about 10:1. For example, the ratio of the targeting vector to the gene editing vector can be about 2:1, about 3:1, about 4:1, about 5:1, about 6:1, about 7:1, about 8:1, about 9:1, or about 10:1. More preferably, the ratio of the targeting vector to the gene editing vector can be from about 2:1 to about 4:1. For example, the ratio of the targeting vector to the gene editing vector can be about 3:1.

The compositions containing the CRISPR-Cas system described herein are administered systemically to a subject. As used herein, "systemic" refers to the administration of the CRISPR-Cas system to multiple organs and/or tissues. Systemic administration can include intravascular administration (such as intravenous injection, intraarterial injection, intracardiac cavity injection) and vascular independent systemic administration such as intraperitoneal injection.

II. Methods for Systemically Treating a Genetic Disorder in a Subject

Also provided are methods of treating a genetic disorder in a subject. Preferably, the genetic disorder is caused by a systemic/widespread mutation in a vital gene of an organism or organ system that result in a truncated, missing or otherwise nonfunctional essential protein. Thus, the methods described herein are directed to treating a genetic disorder that requires bodywide systemic gene therapy that allows for normal expression of a functional protein. Further, in the methods provided herein, the genetic disorder may be treated by co-delivery via systemic administration of the gene editing AAV vector as described herein and the targeting vector as described herein, wherein the targeting vector is provided in excess of the gene editing AAV vector, including in any of the ratios discussed above.

Genetic disorders that may be treated using the methods described herein can include, but are not limited to: an inherited muscle disease, a lyosomal storage disease, a heritable disorder of connective tissue, a neurodegenerative disorder and a skeletal dysplasia.

In various embodiments, the inherited muscle disease may be, for example, a congenital myopathy (e.g., X-linked myotubular myopathy) or a muscular dystrophy (e.g., Duchenne muscular dystrophy, Becker's muscular dystrophy, Lamb-girdle muscular dystrophy, dysferlinopathy, or dystroglycanopathy). Representative muscular dystrophies that may be treated using the methods described herein can include Duchenne muscular dystrophy and Becker's muscular dystrophy.

In various embodiments, the lyososomal storage disease may be selected from the group consisting of aspartylglucosaminuria, Batten disease, cystinosis, Fabry disease, Gaucher disease, Pompe disease, Tay Sachs disease, Sandhoff disease, metachromatic leukodystrophy, mucolipidosis, mucopolysaccharide storage diseases, Niemann-Pick disease, Schindler disease and Krabbe disease.

In various embodiments, the heritable disorder of connective tissue may be selected from the group consisting of Ehlers-Danlos syndrome, epidermolysis bullosa, and Marfan syndrome.

In various embodiments, the neurodegenerative disorder may be selected from the group consisting of neurofibromatosis, spinal muscular atrophy, amyotrophic lateral sclerosis, progressive muscular atrophy, fragile X syndrome, and Charcot-Marie-Tooth disease.

In various embodiments, the skeletal dysplasia is selected from the group consisting of osteogenesis imperfecta, achondroplasia, and osteopetrosis. As described in more detail below, the CRISPR-Cas system works by using a Cas nuclease and a corresponding gRNA that targets the Cas protein to a specific region of the gene of interest. Thus, this system may be modified to target and modify any gene by modifying the gRNA. For example, the gRNA may target a gene such as the AGA gene (aspartylglucosaminuria), CLN3 gene (Batten disease), CTNSgene (cystinosis), GLA gene (Fabry disease), GBA gene (Gaucher disease), GAA gene (Pompe disease), HEXA gene (Tay Sachs disease), HEXB gene (Sandhoff disease), APS A gene (metachromatic leukodystrophy), GNPTAB gene (mucolipidosis), NPCI gene (Niemann-Pick disease), NAGA gene (Schindler disease) and GALC gene (Krabbe disease), or the DMD gene (Duchenne muscular dystrophy, Becker muscular dystrophy, and X-linked dilated cardiomyopathy). Mucopolysaccharide storage diseases (MPS) is a class of disease, not a single one. Some MPS disease genes that may be modified according to the methods described herein include the aspartylglucosaminidase gene (aspartylglucosaminuria), the α-galactosidase A gene (Fabry disease), and the arylsulfatase-A gene (metachromatic leukodystrophy).

In various embodiments, the disease is a muscular dystrophy or a congenital myopathy, such as those listed in Table 1 below. In various embodiments, the CRISPR-Cas system described herein targets any of the genes listed in Table 1. For example, the CRISPR-Cas system may target the DMD gene (Duchenne muscular dystrophy, Becker muscular dystrophy, and X-linked dilated cardiomyopathy), the TTID gene, the LMNA gene, the CAV3 gene, the CAPN3 gene, the DYSF gene, the SGCG gene, the SGCA gene, the SGCB gene, the SGCD gene, the TCAP gene, the TRIM32 gene, the FKRP gene, the TIN gene, the POMT1 gene, or the ANO5 gene (Lamb-girdle muscular dystrophy).

TABLE 1

| Category | Disease Symbol | Disease Name | Inheritance | Genes | Protein Encoded |
|---|---|---|---|---|---|
| Congenital myopathy | NM | Nemaline myopathy | AD, AR | TPM3 | Tropmyosin alplia-3 |
| | | | AR | NEB | Nebulin |
| | | | AD, AR | ACTA1 | Skeletal muscle alpha actin |
| | | | AD | TM2 | Tropomyosin beta-2 |
| | | | AR | TNNT1 | Troponin T slow |
| | | | AR | KBTBD13 | Kelch repeat and BTB Domain containing protein 13 |
| | | | AR | CFL2 | Cofilin 2 |
| | | | AR | KLHL40 | Kelch-like family member 40 |
| | | | AR | KLHL41 | Kelch-like family member 41 |
| | | | AR | LMOD3 | Leiomodin-3 |
| | CNM | Centronuclear myopathy | XL | MTM1 | Myotubularin |
| | | | AD | DNM2 | Dynamin 2 |
| | | | AR | BIN1 | Amphiphysin 2 |
| | | | AR | RYR1 | Skeletal muscle ryanodine receptor |
| | | | AR | TTN | Titin |
| | | | AR | MTMR14 | HJUMPY |
| | | | AD | CCDC78 | Coiled-coil domain containing protein 78 |
| | CCM | Central core myopathy | AD, AR | RYR1 | Skeletal muscle ryanodine receptor |
| | | | AR | SEPN1 | Selenoprotein 1 |
| | | | AD | ACTA1 | Skeletal muscle alpha actin |
| | | | AR | TTN | Titin |

TABLE 1-continued

| Category | Disease Symbol | Disease Name | Inheritance | Genes | Protein Encoded |
|---|---|---|---|---|---|
| Muscular dystrophy | DMD | Duchenne muscular dystrophy | XL | DMD | Dystrophin |
| | BMD | Becker muscular dystrophy | XL | DMD | Dystrophin |
| | LGMD1A | Lamb-girdle muscular dystrophy type 1A | AD | TTID | Myotilin |
| | LGMDIB | Lamb-girdle muscular dystrophy type 1B | AD | LMNA | Lamin A/C |
| | LGMD1C | Lamb-girdle muscular dystrophy type 1C | AD | CAV3 | Caveolin 3 |
| | LGMD2A | Lamb-girdle muscular dystrophy type 2A | AR | CAPN3 | Calpain 3 |
| | LGMD2B | Lamb-girdle muscular dystrophy type 2B | AR | DYSF | Dysferlin |
| | LGMD2C | Lamb-girdle muscular dystrophy type 2C | AR | SGCG | γ-Sarcoglycan |
| | LGMD2D | Lamb-girdle muscular dystrophy type 2D | AR | SGCA | α-Sarcoglycan |
| | LGMD2E | Lamb-girdle muscular dystrophy type 2E | AR | SGCB | β-Sarcoglycan |
| | LGMD2F | Lamb-girdle muscular dystrophy type 2F | AR | SGCD | δ-Sarciglycan |
| | LGMD2G | Lamb-girdle muscular dystrophy type 2G | AR | TCAP | Telethonin |
| | LGMD2H | Lamb-girdle muscular dystrophy type 2H | AR | TRIM32 | Tripartite motif containing 32 |
| | LGMD2I | Lamb-girdle muscular dystrophy type 2I | AR | FKRP | Fukutin-related protein |
| | LGMD2J | Lamb-girdle muscular dystrophy type 2J | AR | TTN | Titin |
| | LGMD2K | Lamb-girdle muscular dystrophy type 2K | AR | POMT1 | Protein-O-mannosyl transferease 1 |
| | LGMD2L | Lamb-girdle muscular dystrophy type 2L | AR | ANO5 | Anoctamin 5 |
| | CMD | Congenital muscular dystrophy | AR | POMT1 | Protein-O-mannosyl transferease 1 |
| | | | AR | POMT2 | Protein-O-mannosyl transferease 2 |

TABLE 1-continued

| Category | Disease Symbol | Disease Name | Inheritance | Genes | Protein Encoded |
|---|---|---|---|---|---|
| | | | AR | POMGnT1 | Protein-O-mannose 1,2-N-acetylglucosaminyl transferase |
| | | | AR | FKRP | Fukitin-related protein |
| | | | AR | LARGE | Glycosyltransferase-like protein LARGE1 |
| | | | AR | LAMA2 | Laminin α2 |
| | | | AR | ITGA7 | Integrin α7 |
| | FSHD | Facioscapulohumeral muscular dystrophy | AD | DUX4 | Double homeobox 4 |
| | DM1 | Myotonic muscular dystrophy type 1 | AD | DMPK | Myotonin-protein kinase |
| | DM2 | Myotonic muscular dystrophy type 1 | AD | CNBP/ZNF9 | Zinc Finger 9 |
| | EDMD | Emery Dreifuss muscular dystrophy | XL | EMD | Emerin |
| | | | AD | LMNA | Lamin A/C |

AD autosomal dominant,
AR autosomal recessive,
XL X-linked.

In the methods described herein, the mutated gene that causes the genetic disease may comprise a frameshift mutation that results in a loss of an open reading frame. In treating the disorder, according to the methods described herein, the mutant gene is edited so that the open reading frame is restored. The mutation can result in a premature stop codon and the system can delete a portion of the target gene comprising the premature stop codon. Alternatively or in addition, the mutation can result in alternative splicing of the gene and the system induces an insertion or deletion in the gene to restore normal splicing of the gene. For example, the system can modify the gene in at least one of: a splicing signal, an exonic splicing enhancer/silencer (ESE/ESS), or an intronic splicing enhancer/silencer (ISE/ISS). In all methods described herein, the dual-vector CRISPR system does not comprise a donor sequence. Therefore, the methods described herein are designed to induce non-homologous end joining.

In the methods of treating a subject, the CRISPR-Cas system described herein may be administered systemically to a subject. As used herein, "systemic" refers to the administration of the CRISPR-Cas system to multiple organs and/or tissues. Systemic administration can include intravascular administration (such as intravenous injection, intraarterial injection, intracardiac cavity injection) and vascular independent systemic administration such as intraperitoneal injection.

For illustration purposes, methods of specifically correctly the dystrophin gene are described herein. These methods can be used to systemically treat Duchenne muscular dystrophy or Becker muscular dystrophy.

Dystrophin

Dystrophin is a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane. The dystrophin gene is 2.2 megabases at locus Xp21. The primary transcription measures about 2,400 kb with the mature mRNA being about 14 kb. 79 exons code for the protein which is over 3500 amino acids. Normal skeleton muscle tissue contains only small amounts of dystrophin but its absence of abnormal expression leads to the development of severe and incurable symptoms. Some mutations in the dystrophin gene lead to the production of defective dystrophin and severe dystrophic phenotype in affected patients. Some mutations in the dystrophin gene lead to partially-functional dystrophin protein and a much milder dystrophic phenotype in affected patients.

DMD is the result of inherited or spontaneous mutations that cause nonsense or frame shift mutations in the dystrophin gene. Naturally occurring mutations and their consequences are relatively well understood for DMD. It is known that in-frame deletions that occur in the exon 45-55 region contained within the rod domain can produce highly functional dystrophin proteins, and many carriers are asymptomatic or display mild symptoms. Furthermore, more than 60% of patients may theoretically be treated by targeting exons in this region of the dystrophin gene. Efforts have been made to restore the disrupted dystrophin reading frame in DMD patients by skipping non-essential exons during mRNA splicing to produce internally deleted but functional dystrophin proteins. The deletion of internal dystrophin exons retain the proper reading frame but cause the less severe Becker muscular dystrophy A CRISPR/Cas-based dual-vector system specific for dystrophin gene are disclosed herein. The CRISPR/Cas-based dual-vector system comprises a first AAV vector encoding a Cas protein (e.g., Cas9 or Cas12) and second AAV vector encoding a gRNA targeting the dystrophin gene. In the systems herein, the ratio of the gRNA-encoding AAV vector to the Cas-encoding AAV vector is greater than or equal to 2:1. Preferably, the ratio of the gRNA-encoding AAV vector to the Cas-encoding AAV vector is from about 2:1 to about 10:1. For example, the ratio can be about 2:1, about 3:1, about 4:1, about 5:1, about 6:1, about 7:1, about 8:1, about 9:1 or about 10:1. Preferably, the ratio is about 3:1.

When delivered to a cell, the two vectors facilitate the expression of the Cas protein and the gRNA which bind and recognize a target region. The target regions may be chosen immediately upstream of possible out-of-frame stop codons such that insertions or deletions during the repair process restore the dystrophin reading frame by frame conversion. Target regions may also be splice acceptor sites or splice donor sites, such that insertions or deletions during the repair process disrupt splicing and restore the dystrophin reading frame by splice site disruption and exon exclusion. Target regions may also be aberrant stop codons such that insertions or deletions during the repair process restore the dystrophin reading frame by eliminating or disrupting the stop codon.

In various embodiments, a dual-vector system for systemically targeting the dystrophin gene in a subject is disclosed. The dual vector system can comprise an AAV vector containing at least one gRNA, as described above. The CRISPR/Cas-based system may use gRNA of varying sequences and lengths. Examples of gRNAs that target the dystrophin gene may be found in US2016/0201089 hereby incorporated by reference. In various embodiments, the CRISPR-Cas dual-vector systems described herein may be engineered to mediate highly efficient gene editing at exon 51 of the dystrophin gene. These CRISPR/Cas-based dual-vector systems restored dystrophin protein expression in cells from DMD patients.

In certain embodiments, the targeting vector comprises a gRNA pair comprising two gRNAs chosen to target two different target regions in the dystrophin gene. The gRNAs can facilitate Cas-mediated cleavage of the dystrophin gene, resulting in a deletion proportional to the distance between the PAM sequences of the gene being targeted (e.g., dystrophin). Thus, in various embodiments, the targeting vector comprises at least one gRNA described in US2016/0201089, incorporated herein by reference. In other embodiments, the targeting vector comprises a first gRNA and a second gRNA such as those described in US2018/0353615, incorporated herein by reference.

In addition, single or multiplexed sgRNAs may be designed to restore the dystrophin reading frame by targeting the mutational hotspot at exons 45-55 and introducing either intraexonic small insertions and deletions, or large deletions of one or more exons.

Exon 51 is frequently adjacent to frame-disrupting deletions in DMD. Elimination of exon 51 from the dystrophin transcript by exon skipping can be used to treat approximately 15% of all DMD patients. This class of DMD mutations is ideally suited for permanent correction by NHEJ-based genome editing and HDR. The CRISPR/Cas9-based systems described herein have been developed for targeted modification of exon 51 in the human dystrophin gene. These CRISPR/Cas9-based systems were transfected into human DMD cells and mediated efficient gene modification and conversion to the correct reading frame. Protein restoration was concomitant with frame restoration and detected in a bulk population of CRISPR/Cas9-based system-treated cells. Similarly, the elimination of exons 45-55 of the dystrophin transcript can be used to treat approximately 62% of all DMD patients.

III. Dual Vector System for Gene Editing

Provided herein are CRISPR/Cas-based dual vector systems for use in genome editing and treating genetic diseases. Any of the dual vector systems provided herein may be used in the methods described above for editing a gene and/or treating a genetic disease in a subject. To that end, the CRISPR/Cas-based dual vector systems may be designed to target any gene, including genes involved in a genetic disease, aging, tissue regeneration, or wound healing. The CRISPR/Cas-based systems may include two AAV vectors, the first AAV vector ("gene editing AAV vector") comprising a gene encoding a Cas protein or Cas fusion protein and the second AAV vector ("targeting AAV vector" comprising at least one gRNA. The Cas fusion protein may, for example, include a domain that has a different activity that what is endogenous to the Cas, such as a transactivation domain. Also provided are constructs and plasmids useful for constructing these AAV vectors as well as pharmaceutical compositions for delivery.

1. Gene Editing Vector: Cas Protein

"Clustered Regularly Interspaced Short Palindromic Repeats" and "CRISPRs", as used interchangeably herein refers to loci containing multiple short direct repeats that are found in the genomes of approximately 40% of sequenced bacteria and 90% of sequenced archaea. The CRISPR system is a microbial nuclease system involved in defense against invading phages and plasmids that provides a form of acquired immunity. The CRISPR loci in microbial hosts contain a combination of CRISPR-associated (Cas) genes as well as non-coding RNA elements capable of programming the specificity of the CRISPR-mediated nucleic acid cleavage. Short segments of foreign DNA, called spacers, are incorporated into the genome between CRISPR repeats, and serve as a 'memory' of past exposures.

CRISPR classification and nomenclature is described in detail in Makarova et al., 2018, hereby incorporated by reference (Makarova et al., "Classification and Nomenclature of CRISPR-Cas Systems: Where from Here?" *The Crispr Journal*. Vol. 1. No. 5. 2018). There are two classes of CRISPR systems (Class 1 and Class 2) which are defined by the configuration of their effector modules. Each comprise different types of effector systems (e.g., the Cas-type nucleases). Class 1 CRISPR systems utilize several Cas proteins and comprise type I, IV and III effector systems. Class 2 systems employ a large single component Cas protein and include the Type II, V, and VI effector systems. At the level of the currently known two classes and Cas types, the classification criteria are straightforward: the fundamental difference in the organization of the effector modules between the classes and the unique signature genes for each of the types. These signatures include cas3 for type I, cas 10 for type III, cas9 for type II, csf1 (large subunit, cavk-like) for type IV, cas 12 for type V, and cas13 for type VI. The Class 2 effectors have a much simpler organization than Class 1 and have an "effector module" consisting of a single, large, multidomain and multifunctional protein. As a result, class 2 effectors have been exploited the most in current genetic engineering methods.

In various embodiments, the gene editing AAV vectors described herein can comprise a Cas gene encoding a Cas protein selected from any of the major types of Cas (e.g., type I Cas, Type II Cas, Type III Cas, Type IV Cas, Type V Cas, Type VI Cas). Preferably, the Cas protein has the ability to generate a targeted, double stranded DNA break. Therefore, in preferred embodiments, the Cas protein is a Type II or Type V Cas, For example, the Cas protein can be a Cas9 (Type II), or a Cas 12 (Type V).

a. Type II: Cas9

The most common CRISPR-system used in eukaryotic cells is the Type II effector system which carries out targeted DNA double-strand break in four sequential steps, using a single effector enzyme, Cas9, to cleave dsDNA. The Type II effector system consists of a long pre-crRNA, which is transcribed from the spacer-containing CRISPR locus, the Cas9 protein, and a tracrRNA, which is involved in pre-crRNA processing. The tracrRNAs hybridize to the repeat regions separating the spacers of the pre-crRNA, thus initiating dsRNA cleavage by endogenous RNase III. This cleavage is followed by a second cleavage event within each spacer by Cas9, producing mature crRNAs that remain associated with the tracrRNA and Cas9, forming a Cas9:crRNA-tracrRNA complex. The Cas9 protein can also be directed to genomic target sites by a synthetically reconstituted "guide RNA" ("gRNA", also used interchangeably herein as a chimeric single guide RNA ("sgRNA")), which is a crRNA-tracrRNA fusion that obviates the need for RNase III and crRNA processing in general.

The Cas9:crRNA-tracrRNA complex unwinds the DNA duplex and searches for sequences matching the crRNA to cleave. Target recognition occurs upon detection of complementarity between a "protospacer" sequence in the target DNA and the remaining spacer sequence in the crRNA. Cas9 mediates cleavage of target DNA if a correct protospacer-adjacent motif (PAM) is also present at the 3' end of the protospacer. For protospacer targeting, the sequence must be immediately followed by the protospacer-adjacent motif (PAM), a short sequence recognized by the Cas9 nuclease that is required for DNA cleavage. Different Type II systems have differing PAM requirements. The *S. pyogenes* CRISPR system may have the PAM sequence for this Cas9 (SpCas9) as 5'-NRG-3', where R is either A or G, and characterized the specificity of this system in human cells. A unique capability of the CRISPR/Cas9 system is the straightforward ability to simultaneously target multiple distinct genomic loci by co-delivery of a single Cas9 protein with two or more sgRNAs. For example, the *Streptococcus pyogenes* Type II system naturally prefers to use an "NGG" sequence, where "N" can be any nucleotide, but also accepts other PAM sequences, such as "NAG" in engineered systems (Hsu et al., Nature Biotechnology (2013) doi:10.1038/nbt.2647). Similarly, the Cas9 derived from *Neisseria meningitidis* (NmCas9) normally has a native PAM of NNNNGATT, but has activity across a variety of PAMs, including a highly degenerate NNNNGNNN PAM (Esvelt et al. Nature Methods (2013) doi:10.1038/nmeth.2681).

A Cas9 molecule of *S. aureus* recognizes the sequence motif NNGRR (R=A or G) and directs cleavage of a target nucleic acid sequence 1 to 10, e.g., 3 to 5, bp upstream from that sequence. In certain embodiments, a Cas9 molecule of *S. aureus* recognizes the sequence motif NNGRRN (R=A or G) and directs cleavage of a target nucleic acid sequence 1 to 10, e.g., 3 to 5, bp upstream from that sequence. In certain embodiments, a Cas9 molecule of *S. aureus* recognizes the sequence motif NNGRRT (R=A or G) and directs cleavage of a target nucleic acid sequence 1 to 10, e.g., 3 to 5, bp upstream from that sequence. In certain embodiments, a Cas9 molecule of *S. aureus* recognizes the sequence motif NNGRRV (R=A or G) and directs cleavage of a target nucleic acid sequence 1 to 10, e.g., 3 to 5, bp upstream from that sequence. In the aforementioned embodiments, N can be any nucleotide residue, e.g., any of A, G, C, or T. Cas9 molecules can be engineered to alter the PAM specificity of the Cas9 molecule.

Exemplary Cas9 nucleases that may be used in the present invention are described in U.S Patent Application No. 2018/0353615, incorporated herein by reference.

b. Type V: Cas12

Another Cas system capable of generating double stranded breaks include Type V. An exemplary Cas protein that works in this system is Cas12 (Cpf1) (Zetsche B. et al. "Cpf1 is a single RNA-guided endonuclease of a Class 2 CRISPR-Cas System" (2015) *Cell* 163:759-771). As described in Zetsche et al., incorporated herein by reference in its entirety, Cas12/Cpf1 containing CRISPR systems have three features. First, Cas12/Cpf1-associated CRISPR arrays are processed into mature crRNAs without the requirement of an additional/ram-activating crRNA (tracrRNA). Instead, they only require a single guide RNA (gRNA) complementary to the target sequence. Second, Cas12/Cpf1-crRNA complexes efficiently cleave target DNA proceeded by short 5' T-rich protospacer-adjacent motif (PAM) on the DNA strand opposite the target sequence, in contrast to the G-rich PAM following the target DNA for Cas9 systems. Third, Cas12/Cpf1 introduces a staggered DNA double stranded break 18 bases 3' of the PAM with a 4 or 5 nt 5' overhang. The structure of the cleavage product makes it particularly advantageous for facilitating non-homologous end joining (NHEJ)-based gene insertion.

Exemplary Cas12 nucleases that can be used in the present invention are described in U.S. Pat. No. 9,790,490 hereby incorporated by reference.

In various embodiments, the gene editing vector can express a Cas-fusion protein. The fusion protein can comprise two heterologous polypeptide domains, wherein the first polypeptide domain comprises a Cas protein and the second polypeptide domain has an activity such as transcription activation activity, transcription repression activity, transcription release factor activity, histone modification activity, nuclease activity, nucleic acid association activity, methylase activity, or demethylase activity. The fusion protein can include a Cas protein or a mutated Cas protein, fused to a second polypeptide domain that has an activity such as transcription activation activity, transcription repression activity, transcription release factor activity, histone modification activity, nuclease activity, nucleic acid association activity, methylase activity, or demethylase activity.

(a) Transcription Activation Activity

The second polypeptide domain can have transcription activation activity, i.e., a transactivation domain. For example, gene expression of endogenous mammalian genes, such as human genes, can be achieved by targeting a fusion protein of iCas9 and a transactivation domain to mammalian promoters via combinations of gRNAs. The transactivation domain can include a VP 16 protein, multiple VP 16 proteins, such as a VP48 domain or VP64 domain, or p65 domain of NF kappa B transcription activator activity. For example, the fusion protein may be iCas9-VP64.

(b) Transcription Repression Activity

The second polypeptide domain can have transcription repression activity. The second polypeptide domain can have a Kruppel associated box activity, such as a KRAB domain, ERF repressor domain activity, Mxil repressor domain activity, SID4X repressor domain activity, Mad-SID repressor domain activity or TATA box binding protein activity. For example, the fusion protein may be dCas9-KRAB.

(c) Transcription Release Factor Activity

The second polypeptide domain can have transcription release factor activity. The second polypeptide domain can have eukaryotic release factor 1 (ERF1) activity or eukaryotic release factor 3 (ERF3) activity.

(d) Histone Modification Activity

The second polypeptide domain can have histone modification activity. The second polypeptide domain can have histone deacetylase, histone acetyltransferase, histone demethylase, or histone methyltransferase activity. The histone acetyltransferase may be p300 or CREB-binding protein (CBP) protein, or fragments thereof. For example, the fusion protein may be dCas9-p300.

(e) Nuclease Activity

The second polypeptide domain can have nuclease activity that is different from the nuclease activity of the Cas9 protein. A nuclease, or a protein having nuclease activity, is an enzyme capable of cleaving the phosphodiester bonds between the nucleotide subunits of nucleic acids. Nucleases are usually further divided into endonucleases and exonucleases, although some of the enzymes may fall in both categories. Well known nucleases are deoxyribonuclease and ribonuclease.

(f) Nucleic Acid Association Activity

The second polypeptide domain can have nucleic acid association activity or nucleic acid binding protein-DNA-binding domain (DBD) is an independently folded protein domain that contains at least one motif that recognizes double- or single-stranded DNA. A DBD can recognize a specific DNA sequence (a recognition sequence) or have a general affinity to DNA. nucleic acid association region selected from the group consisting of helix-turn-helix region, leucine zipper region, winged helix region, winged helix-turn-helix region, helix-loop-helix region, immunoglobulin fold, B3 domain, Zinc finger, HMG-box, Wor3 domain, TAL effector DNA-binding domain.

(g) Methylase Activity

The second polypeptide domain can have methylase activity, which involves transferring a methyl group to DNA, RNA, protein, small molecule, cytosine or adenine. The second polypeptide domain may include a DNA methyltransferase.

(h) Demethylase Activity

The second polypeptide domain can have demethylase activity. The second polypeptide domain can include an enzyme that remove methyl (CH3-) groups from nucleic acids, proteins (in particular histones), and other molecules. Alternatively, the second polypeptide can covert the methyl group to hydroxymethylcytosine in a mechanism for demethylating DNA. The second polypeptide can catalyze this reaction. For example, the second polypeptide that catalyzes this reaction can be Tet1.

The gene editing vector can comprise a nucleic acid encoding any CRISPR/Cas effector protein or fusion protein (e.g., a Cas protein) as described herein. As described further below, the gene editing vector can comprise a ubiquitous or tissue-specific promoter and/or a polyadenylation signal.

The nucleic acid encoding a Cas molecule can be a synthetic nucleic acid sequence. For example, the synthetic nucleic acid sequence can be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein. Additionally or alternatively, a nucleic acid encoding a Cas molecule or Cas polypeptide may comprise a nuclear localization sequence (NLS). Nuclear localization sequences are known in the art.

2. Targeting AAV Vectors: gRNAs

The dual-vector system described herein further comprises an AAV vector providing for one or more gRNAs. As used herein "providing" means facilitating the expression or delivery of the gRNA in a cell of interest. To that end, the AAV vector may deliver the gRNA directly or may contain a DNA sequence which can be transcribed in vivo to generate the gRNA. As described above, gRNAs facilitate the direct targeting of the Cas protein and are designed to be complementary to a nucleic acid target in proximity to the PAM sequence unique to the Cas protein. The gRNAs can be designed differently depending on the Cas protein used. For example, when used in conjunction with a Cas9 protein, the gRNA can be a fusion of two noncoding RNAs: a crRNA and a tracrRNA, thus mimicking the naturally occurring crRNA:tracrRNA duplex involved in the Type II Effector system, described above. This duplex may include, for example, a 42 nucleotide crRNA and a 75 nucleotide tracrRNA. When used in conjunction with a Cas12 protein, the gRNA requires only the crRNA. However it is designed, the gRNA acts as a guide for the Cas protein to cleave the target nucleic acid. The "target region", "target sequence" or "protospacer" as used interchangeably herein refers to the region of the target gene the CRISPR/Cas-based system targets.

The targeting AAV vector used in the methods herein can comprise at least one gRNA, wherein the gRNAs target different DNA sequences. In various embodiments, the targeting AAV vector may comprise a nucleic acid that codes for the gRNAs such that they are transcribed in vivo. The target DNA sequences may be overlapping. When used in conjunction with a Cas9 protein, the target sequence or protospacer may be followed by a PAM sequence at the 3' end of the protospacer. Different Type II systems have differing PAM requirements. For example, the *Streptococcus pyogenes* Type II system uses an "NGG" sequence where "N" can be any nucleotide. Alternatively, when used in conjunction with a Cas12 protein, the target sequence or protospacer may be preceded by a PAM sequence at the 5' end of the protospacer. This PAM sequence is TTTN, where "N" can be any nucleotide.

The number of gRNA included in the targeting AAV vector can be at least 1 gRNA, at least 2 different gRNA, at least 3 different gRNA at least 4 different gRNA, at least 5 different gRNA, at least 6 different gRNA, at least 7 different gRNA, at least 8 different gRNA, at least 9 different gRNA, at least 10 different gRNAs, at least 11 different gRNAs, at least 12 different gRNAs, at least 13 different gRNAs, at least 14 different gRNAs, at least 15 different gRNAs, at least 16 different gRNAs, at least 17 different gRNAs, at least 18 different gRNAs, at least 18 different gRNAs, at least 20 different gRNAs, at least 25 different gRNAs, at least 30 different gRNAs, at least 35 different gRNAs, at least 40 different gRNAs, at least 45 different gRNAs, or at least 50 different gRNAs. The number of gRNA administered to the cell may be between at least 1 gRNA to at least 50 different gRNAs, at least 1 gRNA to at least 45 different gRNAs, at least 1 gRNA to at least 40 different gRNAs, at least 1 gRNA to at least 35 different gRNAs, at least 1 gRNA to at least 30 different gRNAs, at least 1 gRNA to at least 25 different gRNAs, at least 1 gRNA to at least 20 different gRNAs, at least 1 gRNA to at least 16 different gRNAs, at least 1 gRNA to at least 12 different gRNAs, at least 1 gRNA to at least 8 different gRNAs, at least 1 gRNA to at least 4 different gRNAs, at least 4 gRNAs to at least 50 different gRNAs, at least 4 different gRNAs to at least 45 different gRNAs, at least 4 different gRNAs to at least 40 different gRNAs, at least 4 different gRNAs to at least 35 different gRNAs, at least 4 different gRNAs to at least 30 different gRNAs, at least 4 different gRNAs to at least 25 different gRNAs, at least 4 different gRNAs to at least 20 different gRNAs, at least 4 different gRNAs to at least 16 different gRNAs, at least 4 different gRNAs to at least 12 different gRNAs, at least 4 different gRNAs to at least 8 different gRNAs, at least 8 different gRNAs to at least 50 different gRNAs, at least 8 different gRNAs to at least 45 different gRNAs, at least 8 different gRNAs to at least 40 different gRNAs, at least 8 different gRNAs to at least 35 different gRNAs, 8 different gRNAs to at least 30 different gRNAs, at least 8 different gRNAs to at least 25 different gRNAs, 8 different gRNAs to at least 20 different gRNAs, at least 8 different gRNAs to at least 16 different gRNAs, or 8 different gRNAs to at least 12 different gRNAs.

The gRNA may comprise a complementary polynucleotide sequence of the target DNA sequence followed by a PAM sequence. The gRNA may comprise a "G" at the 5' end of the complementary polynucleotide sequence. The gRNA may comprise at least a 10 base pair, at least all base pair, at least a 12 base pair, at least a 13 base pair, at least a 14 base pair, at least a 15 base pair, at least a 16 base pair, at least a 17 base pair, at least a 18 base pair, at least a 19 base pair, at least a 20 base pair, at least a 21 base pair, at least a 22 base pair, at least a 23 base pair, at least a 24 base pair, at least a 25 base pair, at least a 30 base pair, or at least a 35 base pair complementary polynucleotide sequence of the target DNA sequence followed by a PAM sequence. The PAM sequence may be "NGG", where "N" can be any nucleotide. The gRNA may target at least one of an exon, an intron, a promoter region, an enhancer region or a transcribed region of the target gene.

The gRNA may comprise a complementary polynucleotide sequence of the target DNA sequence preceded by a PAM sequence. The gRNA may comprise a "G" at the 5' end of the complementary polynucleotide sequence. The gRNA may comprise at least a 10 base pair, at least all base pair, at least a 12 base pair, at least a 13 base pair, at least a 14 base pair, at least a 15 base pair, at least a 16 base pair, at least a 17 base pair, at least a 18 base pair, at least a 19 base pair, at least a 20 base pair, at least a 21 base pair, at least a 22 base pair, at least a 23 base pair, at least a 24 base pair, at least a 25 base pair, at least a 30 base pair, or at least a 35 base pair complementary polynucleotide sequence of the target DNA sequence preceded by a PAM sequence. The PAM sequence may be "TTTN", where "N" can be any nucleotide. The gRNA may target at least one of an exon, an intron, a promoter region, an enhancer region or a transcribed region of the target gene.

3. Constructs and Plasmids

The gene editing system described herein comprises at least two different AAV vectors capable of delivering nucleic acid that expresses the two CRISPR components (i.e., the Cas protein and the gRNA) into a cell of interest. The first AAV vector (the gene editing AAV vector) comprises a nucleic acid that encodes that Cas protein. The second AAV vector (the targeting AAV vector) provides for at least one gRNA. Optionally, the gRNA(s) may be transcribed from a nucleic acid (DNA) provided in the AAV vector. The AAV vectors may be recombinant AAV vectors. They may further comprise regulatory elements for gene expression of the coding sequences of the nucleic acid. The regulatory elements may be a promoter, an enhancer, an initiation codon, a stop codon or a polyadenylation signal.

The gene editing AAV vector may be capable of expressing a fusion protein, such as a Cas-fusion protein in the cell of a mammal. The vector may comprise heterologous nucleic acid encoding the fusion protein, such as the Cas-fusion protein.

Coding sequences be optimized for stability and high levels of expression. In some instances, codons are selected to reduce secondary structure formation of the RNA such that is formed due to intramolecular bonding.

The AAV vectors may comprise heterologous nucleic acid encoding the Cas protein or the gRNA and may further comprise an initiation codon, which may be upstream of the coding sequence for the Cas protein or the gRNA and a stop codon, which may be downstream of the CRISPR/Cas system coding sequence. The initiation and termination codon may be ion frame with the Cas protein or gRNA coding sequence. The vector may also comprise a promoter that is operably linked to the Cas protein or gRNA coding sequence. The promoter operably linked to the Cas protein or gRNA system coding sequence may be a promoter from simian virus 40 (SV40), a mouse mammary tumor virus (MMTV) promoter, a Moloney virus promoter, an avian leucosis virus (ALV) promoter, a cytomegalovirus (CMV) promoter such as the CMV immediate early promoter, Epstein Barr virus (EBV) promoter, or a Rous sarcoma virus (RSV). The promoter may also be a promoter from a human gene such human ubiquitin C (hUbC), human actin, human myosin, human hemoglobin, human muscle creatine, or human metalothionein. The promoter may also be a tissue specific promoter, such as a muscle or skin specific promoter, natural or synthetic. Examples of such promoters are described in US Patent Application No. US2004175727, incorporated herein by reference.

The AAV vectors may also comprise a polyadenylation signal which may be downstream of the coding sequence for the Cas protein or the gRNA. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 vector (Invitrogen, San Diego, California).

The AAV vectors may also comprise an enhancer upstream of the coding sequence for the Cas protein or the gRNA. The enhancer may be necessary for DNA expression. The enhancer may be human actin, human myosin, human hemoglobin, human muscle creatine, or a viral enhancer such as one from CMV, HA, RSV, or EBV. Polynucleotide function enhancers are described in U.S. Pat. Nos. 5,593,972, 5,962,428 and WO/94/016737, the contents of which are fully incorporated by reference. The vector may also comprise a mammalian origin of replication in order to maintain that the vector extrachromasomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein (GFP) and/or a selectable marker such as hygromycin ("Hygro").'

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments, the vector comprises the nucleic acid sequence encoding the Cas protein or Cas fusion protein and the nucleic acid sequence encoding the at least one gRNA.

Preferably, the genetic constructs comprise AAV vectors. The AAV vector may be AAV8, the sequence of which is described in U.S. Pat. Nos. 7,790,449 and 7,282,199, AAV9 [U.S. Pat. No. 7,906,111; US 2011-0236353-A1], and/or hu37 [see, e.g., U.S. Pat. No. 7,906,111; US 2011-0236353-A1], AAV 1, AAV2, AAV3, AAV4, AAV5, AAV6, AAV6.2, AAV7, AAV8, [U.S. Pat. Nos. 7,790,449; 7,282,199] and others. See, e.g., WO 2003/042397; WO 2005/033321, WO 2006/110689; U.S. Pat. Nos. 7,790,449; 7,282,199; 7,588,772B2 for sequences of these and other suitable AAV, as well as for methods for generating AAV vectors. Still other AAV may be selected, optionally taking into consideration tissue preferences of the selected AAV capsid. A recombinant AAV vector (AAV viral particle) may comprise, packaged within an AAV capsid, a nucleic acid molecule containing a 5' AAV ITR, the expression cassettes described herein and a 3' AAV ITR. As described herein, an expression cassette may contain regulatory elements for an open reading frame(s) within each expression cassette and the nucleic acid molecule may optionally contain additional regulatory elements.

Methods for generating and isolating AAV viral vectors suitable for delivery to a subject are known in the art. See e.g., U.S. Pat. Nos. 7,790,449, 7,282,199, WO 2003/042397, WO20015/033321, WO2006/110689 and U.S. Pat. No. 7,588,772, hereby incorporated by reference. In one system, a producer cell line is transiently transfected with a construct that encodes the transgene flanked by ITRs and a construct(s) that encodes rep and cap. In a second system, a packaging cell line that stably supplies rep and cap is transfected (transiently or stably) with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4, or herpesvirus UL5, UL8, UL52, and UL29 and herpesvirus polymerase) are also supplied in trans by the system. In these newer systems the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and re/cap genes are introduced into insect cells by infection with baculovirus-based vectors. For reviews on production systems, see generally, e.g., Zhang et al., 2009, "Adenovirus-adeno-associated virus hybrid for large-sale recombinant adeno-associated virus production" Human Gene Therapy 20:922-929, the contents of which is incorporated herein by reference. Methods of making and using these and other AAV production systems are also described in the following U.S. patents, the contents of which is incorporated herein by reference in its entirety: U.S. Pat. Nos. 5,139,941; 5,741,683; 6,057, 152; 6,204,059; 6,268,213; 6,491,907; 6,660,514; 6,951,753; 7,094,604; 7,172,893; 7,201,898; 7,229,823; and 7,439,065.

4. Pharmaceutical Compositions

The two AAV vectors in the dual-vector system described herein may be prepared in one or more pharmaceutical compositions. The pharmaceutical composition may be prepared and delivered in accordance with the preferred ratios of the gene editing vector: targeting vector described herein. Therefore, the pharmaceutical compositions may be delivered at a dose of from about $0.5 \times 10^{14}$ vector genome (vg) copies per kilogram body weight (vg/kg) to about $5 \times 10^{14}$ vg/kg of the AAV vector comprising the Cas gene (i.e., the gene editing AAV vector) and from about $1 \times 10^{14}$ vg/kg to about $5 \times 10^{15}$ vg/kg of the AAV vector providing the gRNA(s) (i.e., the targeting AAV vector).

In various embodiments, the gene editing vector and the targeting AAV vector may be prepared separately. In some embodiments, the gene editing AAV vector may be prepared as a solution having a concentration of from about $5.2 \times 10^{10}$ vg/µl to about $9.9 \times 10^{10}$ vg/µl. In some embodiments, the targeting AAV vector solution may be prepared as a solution having a concentration from about $1.0 \times 10^{10}$ vg/µl to about $1.2 \times 10^{11}$ vg/µl. The separate solutions may be mixed prior to administration, according to the doses described above, or may be administered separately.

In various embodiments, the ratio of the targeting AAV vector (gRNA AAV vector) to the gene editing AAV vector (Cas AAV vector) in the pharmaceutical composition may be greater than or equal to 2:1. In various embodiments, the ratio of the targeting AAV vector to the gene editing AAV vector may be from about 2:1 to about 10:1. In other embodiments, the ratio of the targeting AAV vector to the gene editing AAV vector may be about 2:1, about 3:1, about 4:1, about 5:1, about 6:1, about 7:1, about 8:1, about 9:1 or about 10:1. For example, the ratio of the targeting AAV vector to the gene editing vector can be about 3:1.

The compositions described herein are formulated according to the mode of administration used. In cases where pharmaceutical compositions are injectable pharmaceutical compositions, they are sterile, pyrogen free, and particulate free. An isotonic formulation is preferably used. Generally, additives for isotonicity may include sodium chloride, dextrose, mannitol, sorbitol, and lactose. In some cases, isotonic solutions such as phosphate buffered saline are preferred. Stabilizers include gelatin and albumin. In some embodiments, a vasoconstriction agent is added to the formulation.

The compositions may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the composition for genome editing in skeletal muscle or cardiac muscle at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA vector encoding the composition may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

Having described the invention in detail, it will be apparent that modifications and variations are possible without departing from the scope of the invention defined in the appended claims.

EXAMPLES

The following non-limiting examples are provided to further illustrate the present invention.
Summary of CRISPR-Treated MDX Mice and the Examples The following examples describe three long-term systemic CRISPR studies that were performed in the mdx mouse model of Duchenne muscular dystrophy (DMD) described in McGreevy et al., incorporated herein by reference ("Animal models of Duchenne muscular dystrophy: from basic mechanisms to gene therapy" *Disease Models and Mechanisms.* 2016 March; 8(3): 195-213). Two AAV vectors were co-delivered intravenously. One AAV vector expressed Cas9 and was named the Cas9 vector. The other AAV vector expressed two gRNAs targeting introns 22 and 23. This second vector was named the gRNA vector. Both vectors were packaged in AAV serotype-9 (AAV-9). Table 2 below shows the sample size, sex, age, body weight and vector dose at the time of tail vein injection. The first study, described in Example 1, was named the 2:1 study because the ratio of the Cas9 vector to the gRNA vector was 2:1. In the remaining two studies (Examples 2 and 3), the ratio of the Cas9 vector to the gRNA vector was 1:3. These two studies were named the male 1:3 study and the female 1:3 study based on the sex of the experimental mice.

Different batches of the same vector were combined, aliquoted, and stored in a −80° C. freezer. Freshly thawed aliquots were used for mouse injection. The Cas9 and gRNA vectors were mixed thoroughly at the indicated quantity before injection. For systemic injection, AAV was delivered via the tail vein (see Table 2 and Examples 1-3 below). For local injection, AAV was delivered directly to the tibialis anterior muscle (Example 5, below).

AAV Titration method: The AAV titer was determined by using SYBR green quantitative PCR. For the Cas9 AAV vector, we used a primer pair targeting bGHpA (forward, 5'-CGACTGTGCCTTCTAGTTGCC-3', SEQ ID NO: 1; reverse, 5'-GACACCTACTCAGACAATGCGATG-3', SEQ ID NO: 2). For the gRNA AAV vector, we used a primer pair targeting SV40 pA (forward, 5'-AGCAATAGCATCACAAATTTCACAA-3', SEQ ID NO: 3; reverse, 5'-CCAGACATGATAAGATACATTGATGAGTT-3', SEQ ID NO: 4). The following thermocycler program was used for amplification using 7900HT Fast-Real-Time PCR System (Applied Biosystems). Samples were denatured at 95° C. for 2 minutes. This initial denaturation was followed by 40 cycles at 95° C. for 15 seconds and 60° C. for 1 minute. Each sample was replicated 6-8 times for quantification. Final viral titer was calculated against a 6-point plasmid standard series representing $1 \times 10^6$ vg/µl to $1 \times 10^{11}$ vg/µl at log 10 increments for each vector (FIGS. 1B, 1C, 1E, 1F, and 1G).

Figure 1B:
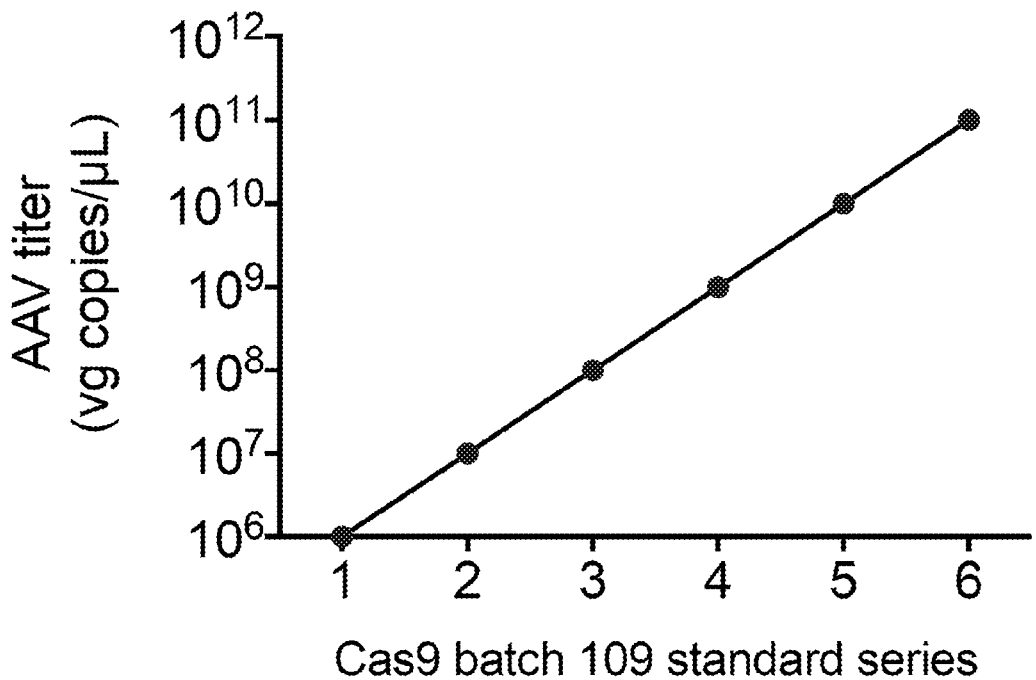
FIG. 1B shows a standard curve for one of two Cas9 AAV vector batches prepared (batch 109)
Figure 1C:
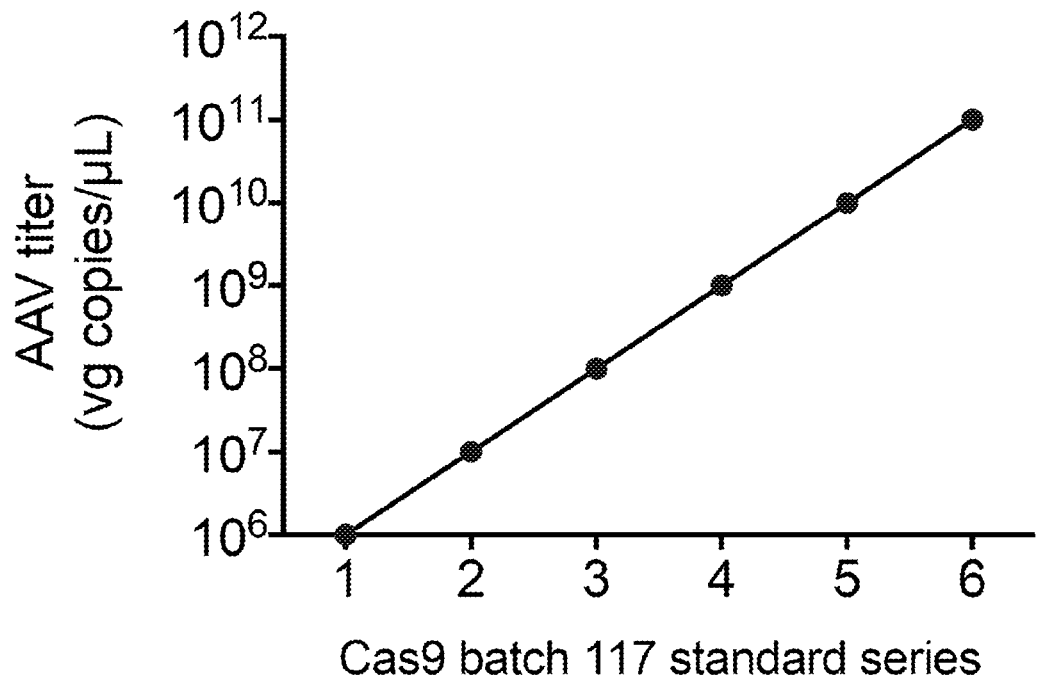
FIG. 1C shows a standard curve for one of two Cas9 AAV vector batches prepared (batch 117).
Figure 1D:
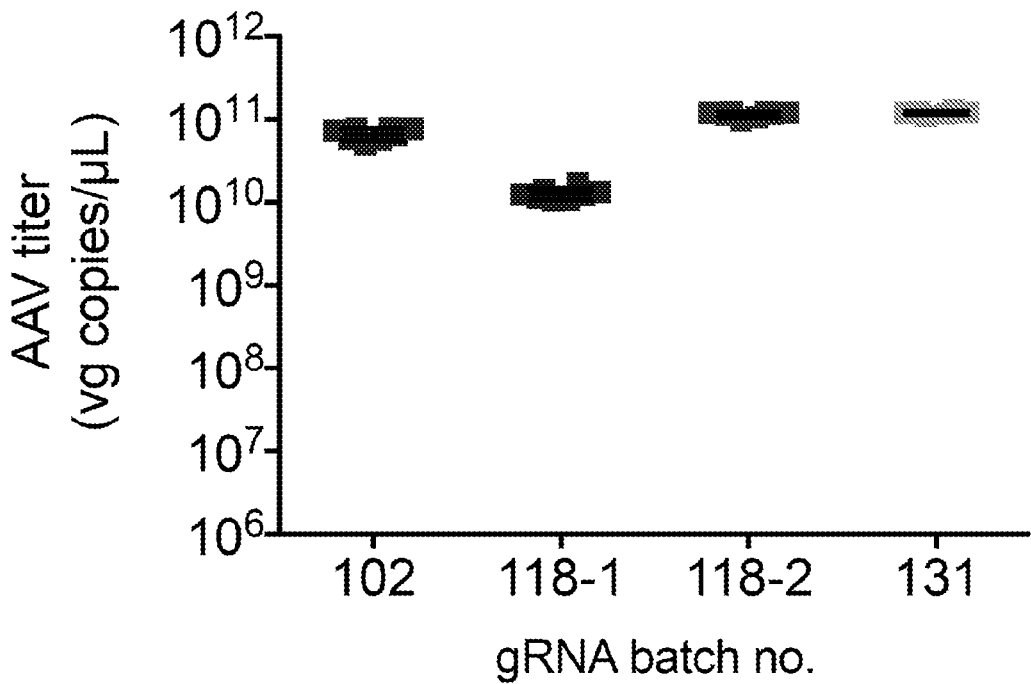
FIG. 1D depicts a scatter plot with individual AAV vector titer values (vg copies/µg) generated from different samples taken from four gRNA batches prepared.
Figure 1E:
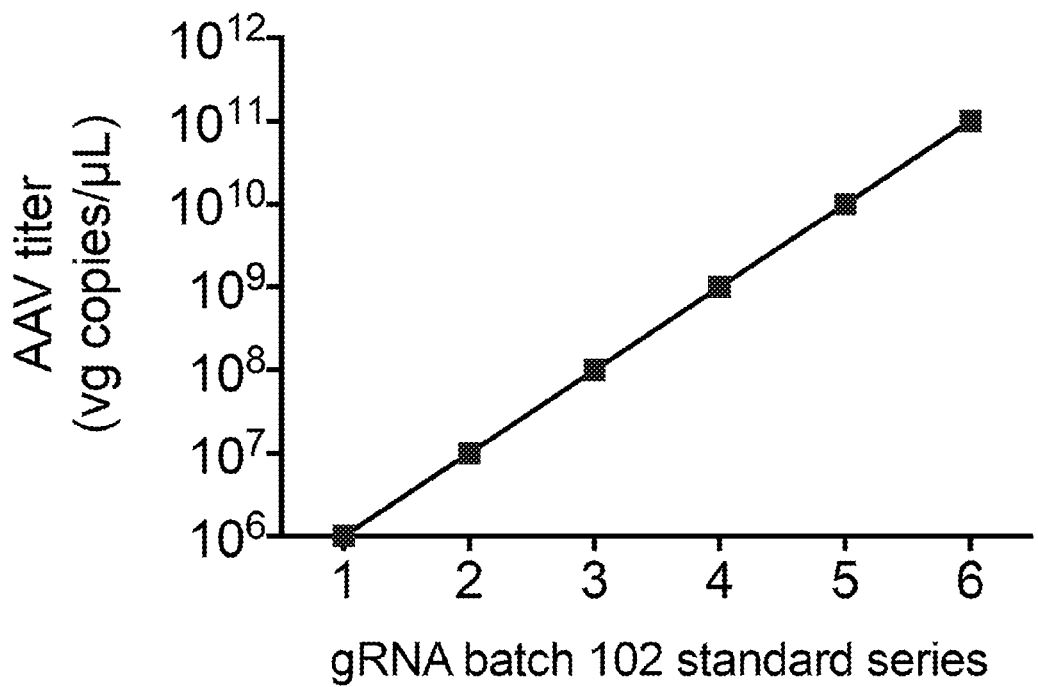
FIG. 1E shows a standard curve for one of four gRNA batches prepared (batch 102)
Figure 1F:
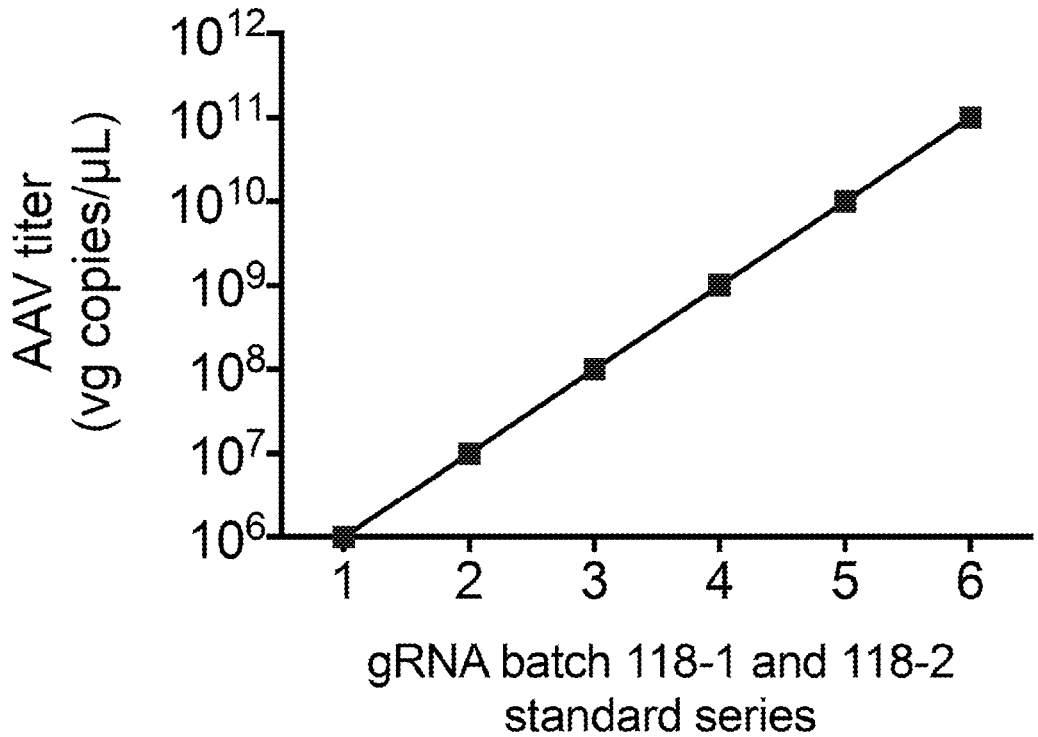
FIG. 1F shows a standard curve for two of four gRNA batches prepared (batches 118-1 and 118-2). These batches were prepared in the same PCR reaction.
Figure 1G:
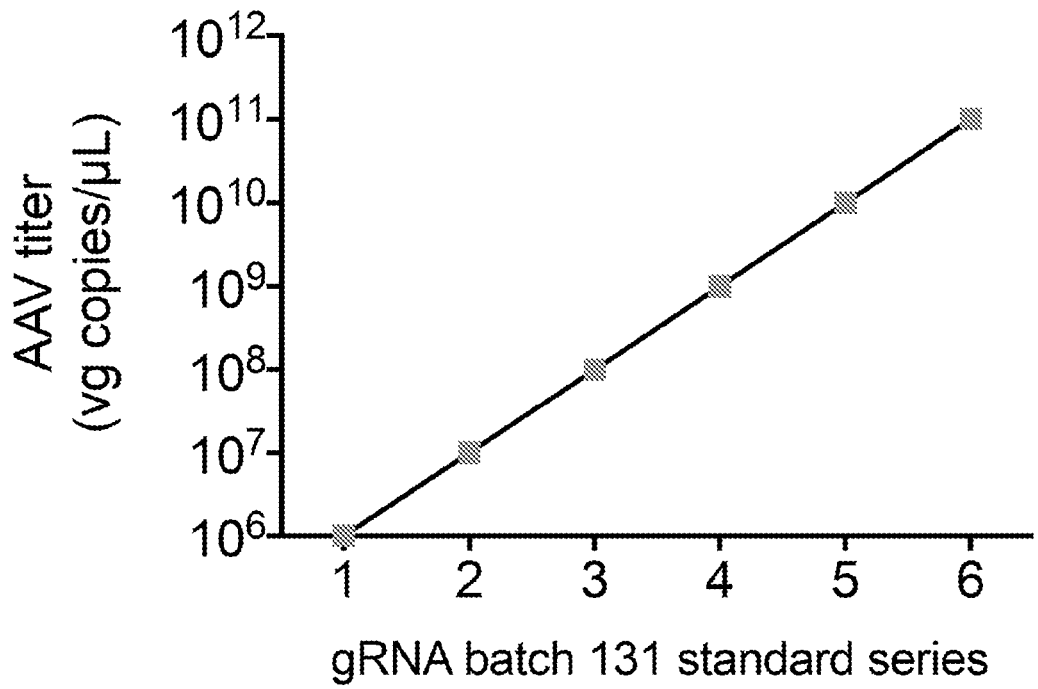
FIG. 1G shows a standard curve for one of four gRNA batches prepared (batch 131).

FIG. 1A-FIG. 1C shows the titration results for the SaCas9 vector and FIG. 1D-FIG. 1G show the titration results for the gRNA vector. Table 3, below indicates the number of qPCR reactions and the batch titer determined by averaging across the qPCR reactions performed in each batch. FIG. 1A and FIG. 1G graphically depict individual titer values for each of the reactions performed for each batch.

TABLE 2

| Example No. | Study | N | Sex | Age at injection (m) | Body weight at injection (g) | AAV vector (vg/mouse) | | AAV vector (vg/kg) | |
|---|---|---|---|---|---|---|---|---|---|
| | | | | | | Cas9 | gRNA | Cas9 | gRNA |
| 1 | 2:1 | 5 | M | 1.54 ± 0.02 | 22.58 ± 0.43 | 7.0E+12 | 3.63E+12 | 3.19E+14 | 1.61E+14 |
| 2 | Male 3:1 | 6 | M | 1.56 ± 0.07 | 21.54 ± 0.55 | 1.00E+13 | 3.00E+13 | 4.61E+14 | 1.381E+15 |
| 3 | Female 3:1 | 8 | F | 1.48 ± 0.05 | 16.14 ± 0.68 | 1.00E+13 | 3.00E+13 | 6.07E+14 | 1.82E+15 |

Materials and Methods

Study design. Our objective was to study long-term therapeutic benefits of AAV CRISPR therapy in a mouse DMD model. The sample size was determined based on previous experience. We did not use exclusion, randomization, or blinding approaches to assign animals to experimental group. Cardiac functional data from untreated normal and mdx mice also included those from our ongoing natural history study. All the data were included in the analysis. The primary endpoint was dystrophin expression. The secondary endpoints included vector genome copy number, Cas9 expression, on/off-target evaluation, and muscle and heart function. For each experiment, sample size reflected the number of independent biological replicates and is provided in related figures and tables.

Mice. Experimental mice were generated in house in a barrier facility using breeders purchased from the Jackson Laboratory. All mice were maintained in a specific pathogen-free animal care facility on a 12-hour-light (25 lux)/12-hour-dark cycle with access to food and water ad libitum.

AAV production and administration: The Cas9 and gRNA cis-plasmids have been published previously (2). AAV-9 vectors were generated by the transient transfection method and purified using CsCl ultracentrifugation, as was reported previously (30). A total of two independent batches of the SaCas9 vector and four independent batches of the gRNA vector were made for the studies. Each batch was independently titrated by PCR (see below, FIG. 1A-FIG. 1G).

TABLE 3

| Batch Name | Vector | # qPCR reactions | Batch titer |
|---|---|---|---|
| 109 | Cas9 | 9 | $8.23 \times 10^{10}$ vg/µl |
| 117 | Cas9 | 8 | $6.02 \times 10^{10}$ vg/µl |
| 102 | gRNA | 8 | $6.63 \times 10^{10}$ vg/µl |
| 118-1* | gRNA | 8 | $1.28 \times 10^{10}$ vg/µl |
| 118-2* | gRNA | 8 | $1.15 \times 10^{11}$ vg/µl |
| 131 | GRNA | 6 | $1.20 \times 10^{11}$ vg/µl |

*performed on same qPCR plate and share same standard curve

Morphological studies: Tissues were harvested at the indicated time point in liquid nitrogen-cooled 2-methylbutane in the Tissue-Plus optimal cutting temperature compound (Scigen Scientific). General histology and fibrosis were examined by H&E and Masson trichrome staining, respectively. Dystrophin was detected with a rabbit polyclonal antibody against the C-terminal domain (catalog RB 9024, 1:200; ThermoFisher Scientific). Slides were viewed using a Nikon E800 fluorescence microscope. Photomicrographs were taken with a Leica DFC7000 camera.

Western Blot: Proteins from heart and skeletal muscle were extracted according to our published protocol (31). Dystrophin was detected with a rabbit polyclonal antibody against the C-terminal domain (catalog RB 9024, 1:500, Thermo Fisher Scientific). Cas9 was detected with a rat monoclonal antibody against the HA tag (catalog 1-867-423, 1:500, Roche). Vinculin was used as a loading control and was detected with a rabbit polyclonal antibody (catalog ab155120, 1:2000, Abcam). Signal was detected using Clarity Western ECL substrate (Bio-Rad) and visualized using the Li-COR Odyssey imaging system. In experiments shown in FIG. 38A and FIG. 38B infrared fluorescence dye conjugated secondary antibodies were used (LI-COR Biotechnology). Densitometry quantification was performed using the Li-COR Image Studio version 5.0.21 software (www-.licor.com). The relative intensity of the protein was normalized to the corresponding vinculin band in the same blot and further normalized to the WT control.

Vector genome copy number quantification: Genomic DNA was extracted from OCT-embedded tissues. DNA concentration was determined using the Qubit dsDNA high-sensitivity assay kit (Thermo Fisher Scientific). The vector genome copy number was quantified by TaqMan PCR using the TaqMan Universal PCR master mix (Thermo Fisher Scientific) and custom-designed primers and probes (Table 4, below). The threshold cycle value of each reaction was converted to the vector genome copy number by measuring against the copy number standard curve of the known amount of the cis-plasmid.

cDNA was generated using the Superscript IV Kit (Thermo Fisher Scientific) and quantified using the Qubit ssDNA assay kit (Thermo Fisher Scientific). The dystrophin transcript was quantified by digital droplet PCR in the QX200 ddPCR system (Bio-Rad) using ddPCR supermix (Bio-Rad). Primers and probes for the junctions of exon 22-23, 22-24, and 24-25 are described in FIG. 2 and Table 3, above.

Figure 2:
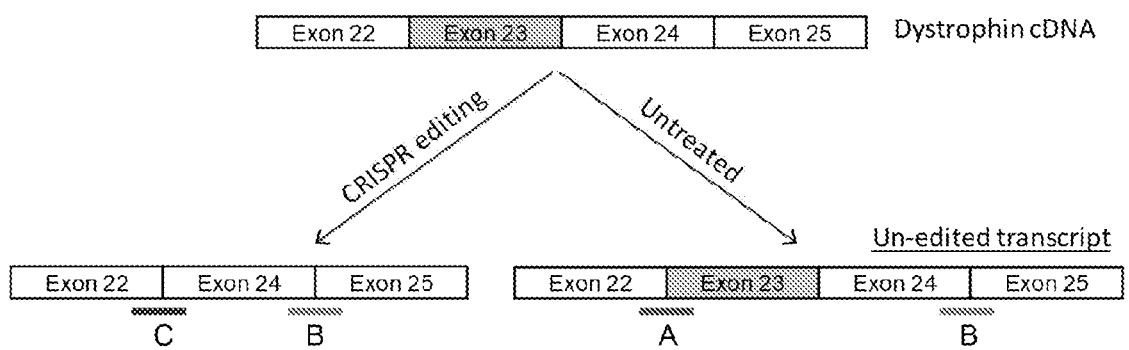
FIG. 2 depicts a schematic outline of the strategy used in quantitative reverse transcription PCR for quantifying editing in the dystrophin cDNA via CRISPR-Cas9 techniques.

FIG. 2 depicts a schematic outline of the strategy used in quantitative reverse transcription PCR for studying dystrophin cDNA. The mdx mouse has a nonsense mutation in exon 23 of the dystrophin gene. In CRISPR therapy, the mutated exon 23 and its surrounding intronic sequences are removed from the mutated gene. The resulting transcript does not contain exon 23. TaqMan PCR experiments were designed to amplify the junctions of exons 22-23 (product A in the figure) and exons 22-24 (product C in the figure) to detect the unedited and edited transcript, respectively. The exons 24-25 junction (product B in the figure) was used as the internal control for all (both edited and unedited) dystrophin transcripts. In untreated mdx mice, it was expected that product B would equal product A. CRISPR treated mdx mice have both edited and unedited transcripts so in those animals product B should equal the sum of product A and product C. The percentage of the edited dystrophin transcript is calculated using the formula: (product C)/(product B). The percentage of the unedited dystrophin transcript is calculated using the formula: (product A)/(product B). The data were reported as the transcript copy per ng of cDNA used in the reaction.

Analysis of on- and off-target gene editing: On- and off-target cutting was analyzed using DNA extracted from flash frozen livers according to a previously published

TABLE 4

| Target | Foward Primer (SEQ ID NO) | Reverse Primer (SEQ ID NO) | TaqMan Probe (SEQ ID NO) |
| --- | --- | --- | --- |
| SaCAS9 | CGCACAGAAGATGATCAATGAGATG (SEQ ID NO: 5) | TTCGGATAATCTCTTCAATGCGTTCA (SEQ ID NO: 6) | TTGGTCTGCCGGTTTC (SEQ ID NO: 7) |
| gRNA | GAGCGCACCATCTTCTTCAAG (SEQ ID NO: 8) | TGTCGCCCTCGAACTTCAC (SEQ ID NO: 9) | ACGACGGCAACTACA (SEQ ID NO: 10) |
| Exon 22-23 | CTGAATATGAAATAATGGAGGAGAGACTCG (SEQ ID NO: 11) | AGTTGAAGCCATTTTGTTGCTCTTTC (SEQ ID NO: 12) | CAGAGCCTGTAATTTC (SEQ ID NO: 13) |
| Exon 22-24 | AGGAGAGACTCGGGAAATTACAGAA (SEQ ID NO: 14) | GGCAGGCCATTCCTCTTTCA (SEQ ID NO: 15) | CAGCCATCCATTTCTG (SEQ ID NO: 16) |
| Exon 24-25 | GGGATGCTGAAATCCTGAAAAAACA (SEQ ID NO: 17) | TTCTGCCCACCTTCATTAACACTATT (SEQ ID NO: 18) | TCAAACAATGCAGACTTTT (SEQ ID NO: 19) |

Dystrophin transcript quantification: RNA was extracted from tissues preserved in RNA later (Thermo Fisher Scientific) using the RNeasy Fibrous Tissue kit (Qiagen). The protocol (2). Primers used for deep sequencing are listed in Table 5 below. Analysis was performed with CRISPResso using a 5-bp window from the expected DSB (32).

TABLE 5

| Primer | Sequence | SEQ ID NO: |
| --- | --- | --- |
| 1 | TCGTCGGCAGCGTCAGATGTGTATAAGAGACAG tttctgtctaaatataatatgccctgt | 20 |
| 2 | GTCTCGTGGGCTCGGAGATGTGTATAAGAGACAG gcagagcctcaaaattaaatagaag | 21 |
| 3 | TCGTCGGCAGCGTCAGATGTGTATAAGAGACAG gagctcatcctctttcatgct | 22 |
| 4 | GTCTCGTGGGCTCGGAGATGTGTATAAGAGACAG gaaggaggaacaggcaggag | 23 |
| 5 | TCGTCGGCAGCGTCAGATGTGTATAAGAGACAG aaagttgttagagcctgctcatt | 24 |

TABLE 5-continued

| Primer | Sequence | SEQ ID NO: |
|---|---|---|
| 6 | GTCTCGTGGGCTCGGAGATGTGTATAAGAGACAG tttagtagacggaagaaagctca | 25 |
| 7 | TCGTCGGCAGCGTCAGATGTGTATAAGAGACAG tggatatcctcctgggaatg | 26 |
| 8 | GTCTCGTGGGCTCGGAGATGTGTATAAGAGACAG gcctcaactggaaactgagc | 27 |
| 9 | AATGATACGGCGACCACCGAGATCTACACTCGTCGGCAGCGTC | 28 |
| 10 | CAAGCAGAAGACGGCATACGAGAT NNNNNN GTCTCGTGGGCTCGG | 29 |

UPPERCASE, specific for Illumina sequencing
Lowercase, genome specific sequence
NNNNNN, barcodes used in the sequencing Skeletal muscle function assay: EDL muscle function was evaluated ex vivo using our published protocols (27, 28). Muscle force was evaluated with a 305B dual-mode servomotor transducer using the Dynamic Muscle Control software (Aurora Scientific). Data were analyzed using the Dynamic Muscle Analysis (DMA) software (Aurora Scientific). The specific muscle force was calculated by dividing the absolute muscle force with the muscle cross-sectional area (CSA). Muscle CSA was calculated according to the following equation: CSA=(muscle mass)/(muscle density× length ratio×optimal muscle length). Muscle density is 1.06 g/cm3 (33). The length ratio is 0.44 for the EDL muscle (34, 35).

ECG and left ventricular hemodynamic assay: A 12-lead ECG assay was performed using a system from AD Instruments as previously published (36, 37). The ECG parameters were analyzed using ECG analysis module in Lab Chart software. The Q wave amplitude was determined using the lead I tracing. Other parameters were analyzed using the lead II tracing. The QTc interval was determined by correcting the QT interval with the heart rate as described by Mitchell et al. (38). The cardiomyopathy index was calculated by dividing the QT interval by the PQ segment (39). Left ventricular hemodynamics was evaluated with a closed chest approach using the Millar ultraminiature pressure-volume catheter (29, 37). Data were analyzed with the PVAN software (Millar Instruments). Detailed protocols are available at the Parent Project Muscular Dystrophy standard operating protocol web site (40).

Statistics: Data are presented as mean±SEM. The sample size mentioned refers to the number of animals. For biochemical and molecular assays, 2-3 measurements were conducted in each assay for each animal. The average from these measurements was reported as the data for each animal. One-way ANOVA or two-way ANOVA with Tukey's multiple comparison was performed for statistical analysis for more than 2 group comparisons. Unpaired t test (2 tailed) or Mann-Whitney test was used for 2 group comparisons. The statistical method used for each analysis is indicated in the figure legends. All statistical analyses were performed using GraphPad PRISM software version 7.0. $P<0.05$ was considered statistically significant.

Study approval: All animal experiments were approved by the University of Missouri animal care and use committee.

Figure 3A:
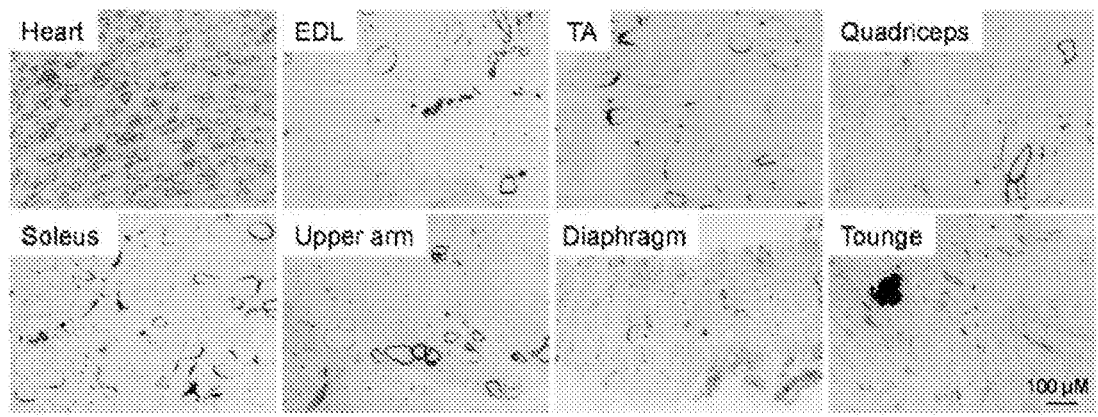
FIG. 3A depicts representative muscle and heart dystrophin immunostaining photomicrographs from a 8 month old male mdx mouse that had received intravenous injection of the Cas9 vector ($7.2\times10^{12}$ vg/mouse) and the gRNA vector ($3.6\times10^{12}$ vg/mouse) at 6 weeks.
Figure 3B:
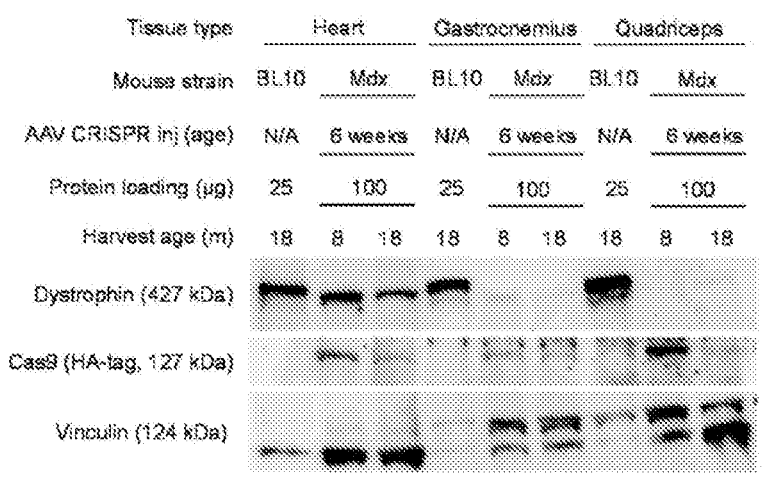
FIG. 3B is a representative dystrophin and Cas9 western blot from the heart, gastrocnemius and quadriceps from a male mdx mouse harvested at 8 months of age and a male mdx mouse harvested at 18 months of age, each mouse having received intravenous injection of the Cas9 vector ($7.2\times10^{12}$ vg/mouse) and the gRNA vector ($3.6\times10^{12}$ vg/mouse) at 6 weeks. Tissue from an 18 month old BL10 mouse was used as a wild-type control. Vinculin served as the loading control. N/A, no AAV injection.

Example 1: Long-Term Systemic AAV CRISPR Therapy with a Cas9:gRNA Vector Ratio of 2:1 in Mdx Mice Effective DMD treatment requires persistent dystrophin restoration and functional improvements in both skeletal and cardiac muscles. To determine whether systemic AAV CRISPR therapy could lead to long-lasting protection for DMD, Cas9 and gRNA vectors were co-injected into six 6-week old male mice at the dose of $7.2 \times 10^{12}$ and $3.6 \times 1012$ vg/mouse ($3.2 \times 10^{14}$ and $1.6 \times 10^{14}$ vg/kg), respectively. The AAV.Cas9 vector and the AAV.gRNA vector were published before (Nelson et al Science 351:403-7, 2016). One mouse was harvested at 8 months of age to evaluate dystrophin restoration. By immunostaining and Western blot, robust dystrophin expression was detected in the heart but not in skeletal muscle (FIGS. 3A and 3B). The remaining mice were harvested at 18 months of age. Age/sex-matched normal BL10 (wild type, WT) mice and untreated mdx mice were used as controls. Samples were immunostained for dystrophin and subjected to western blotting to measure protein levels. Data for the 18 month old mice are shown in FIGS. 4B, 4C, 4D and 4E.

Figure 4A:
FIG. 4A. Schematic overview of a study investigating long-term systemic AAV CRISPR therapy with a Cas9: gRNA vector ratio of 2:1 in mdx mice.
Figure 4B:
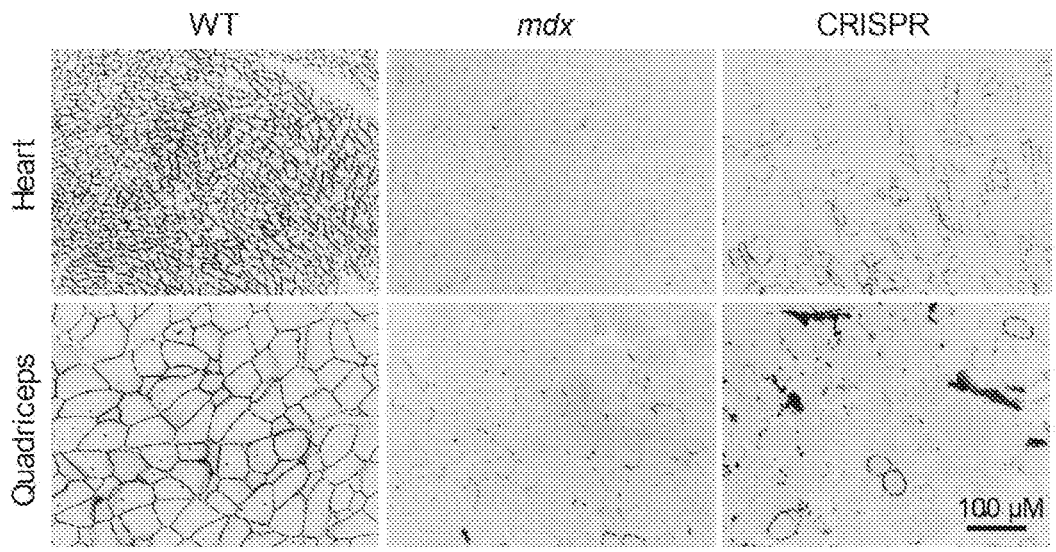
FIG. 4B. Representative dystrophin immunostaining photomicrographs from the heart and quadriceps of treated and untreated animals.
Figure 4C:
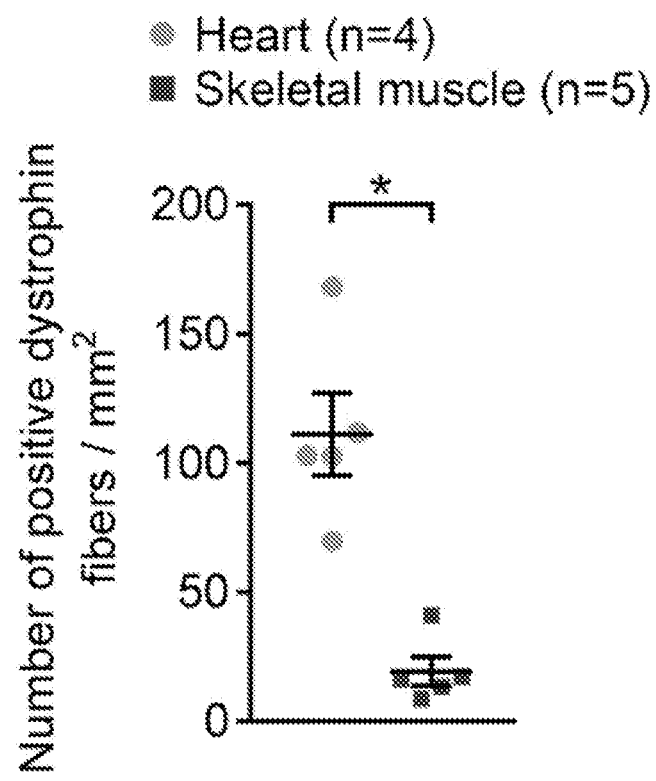
FIG. 4C. Quantitation of the number of fibers positive for dystrophin in the heart and skeletal muscle of mdx mice treated with a 2:1 vector ratio of Cas9 to gRNA.
Figure 4D:
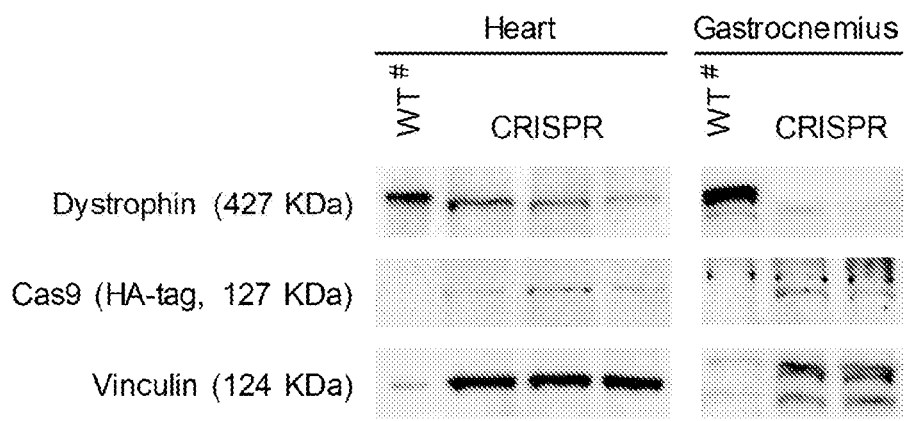
FIG. 4D. Representative dystrophin and Cas9 western blots from the heart and gastrocnemius of treated and untreated animals Pound sign (#), loading is different in this lane.
Figure 4E:
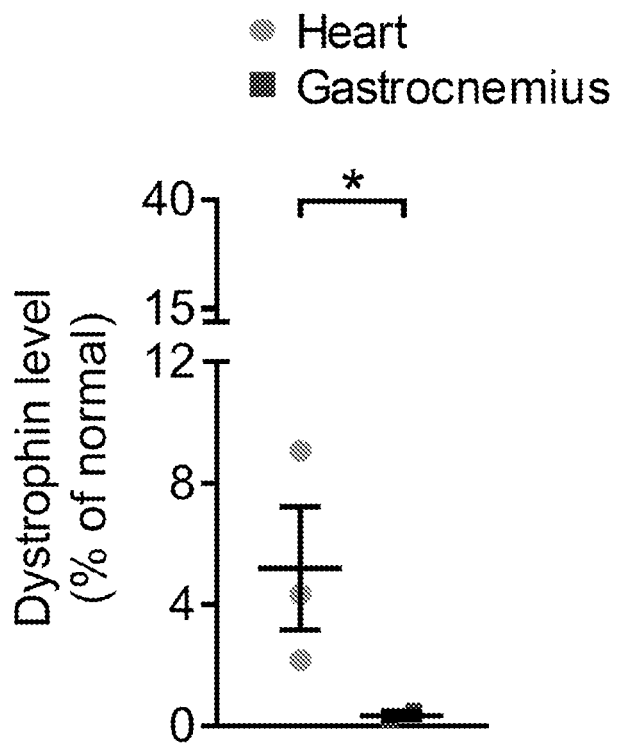
FIG. 4E. LICOR quantification of dystrophin western blot. Asterisk, statistically significant ($p<0.05$).

FIG. 4B shows representative dystrophin immunostaining photomicrographs from the heart and quadriceps. Abundant dystrophin positive myocytes were detected in the heart but not quadriceps (skeletal muscle) in CRISPR treated mice (FIG. 4C). FIG. 4D shows a representative dystrophin and Cas9 western blots from the heart and quadriceps. Vinculin western was included as the loading control. Cardiac dystrophin reached approximately 5% of the WT level, but barely any dystrophin were detected in the skeletal muscle. FIG. 4E shows LICOR quantification of the dystrophin western blot. Asterisk, statistically significant ($p<0.05$). Pound sign (#), loading is different in this lane.

Figure 5A:
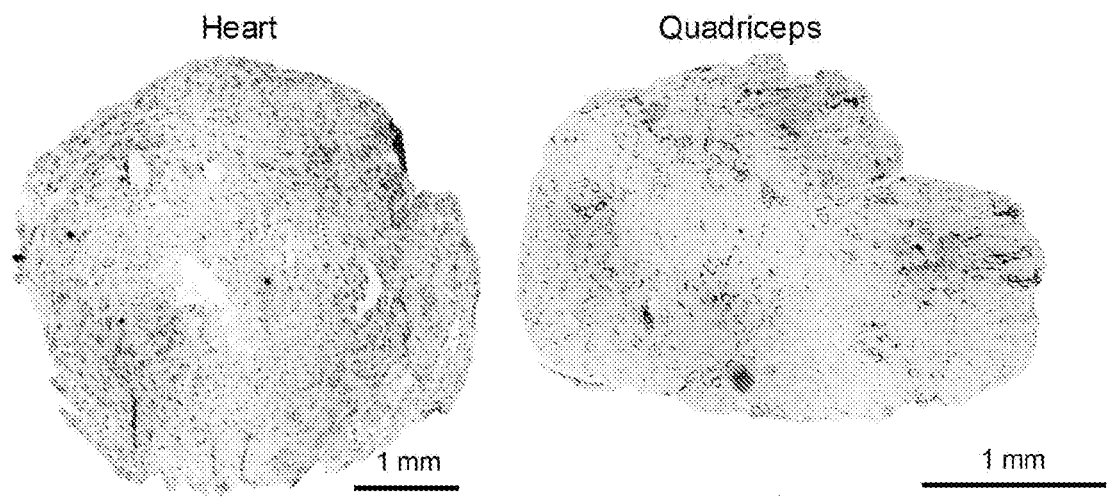
FIG. 5A. Representative dystrophin immunostaining photomicrographs from the heart and various skeletal muscles of a CRISPR treated mouse (2:1 Cas9 to gRNA vector ratio). Full-view image of the heart and quadriceps (skeletal muscle).
Figure 5B:
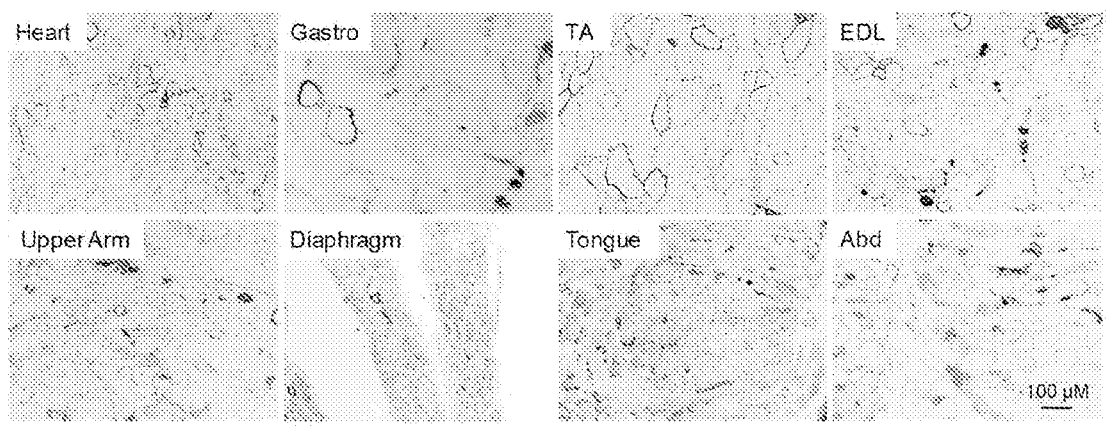
FIG. 5B: Representative dystrophin immunostaining photomicrographs from the heart and various skeletal muscles of a CRISPR treated mouse (2:1 Cas9 to gRNA vector ratio). High-power images from the heart, gastrocnemius, tibialis anterior (TA), extensor digitorum longus (EDL), upper arm muscle, diaphragm, tongue and abdominal muscle (Abd).

Levels of dystrophin throughout the body of another CRISPR treated 18 mo. old mouse were examined using immunostaining and representative images are shown in FIG. 5. Similar to the results in FIG. 4, abundant dystrophin positive cardiomyocytes were detected in the heart (FIG. 5A) and while varied numbers of dystrophin positive myofibers were seen in different skeletal muscles (FIG. 5B), in general, only low levels of dystrophin were observed in skeletal muscles.

Figure 6:
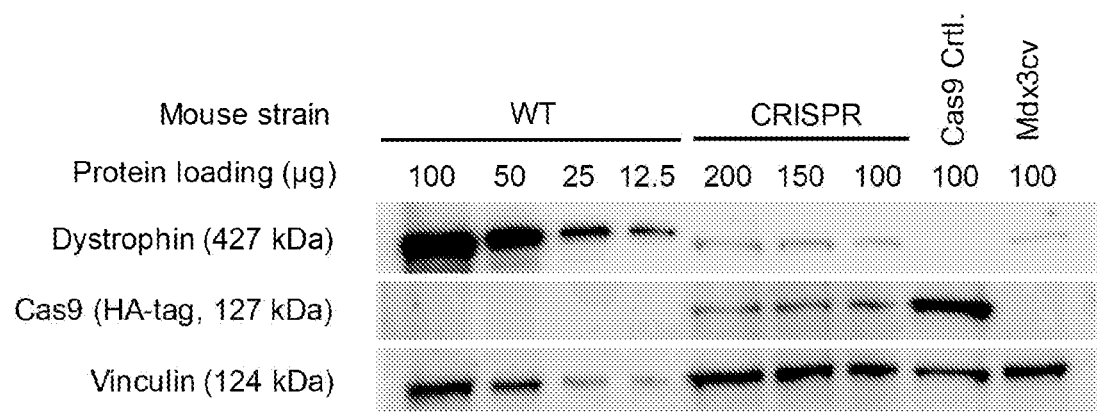
FIG. 6. Representative dystrophin western blot from the heart of an 18-m-old BL10 mouse, the heart of an 18-m-old mdx mouse that received CRISPR therapy (Cas9:gRNA=2: 1) at 6 weeks of age, the tibialis anterior muscle of a 3-m-old mdx mouse that received local Cas9 vector (but not gRNA vector) injection at 6 weeks of age (Cas9 control), and the heart of an 18-m-old mdx3cv mouse. Vinculin is the loading control.

FIG. 6 shows a representative western blot showing levels of dystrophin, Cas9 and vinculin (loading control) in (from left to right), the heart of an 18 month old BL10 (WT) mouse (not exposed to CRISPR), the heart of an 18-m-old mdx mouse that received CRISPR therapy (Cas9:gRNA=2:1) at 6 weeks of age, the tibialis anterior muscle of a 3-m-old mdx mouse that received local Cas9 vector (but not gRNA vector) injection at 6 weeks of age (Cas9 control), and the heart of an 18-m-old mdx3cv mouse. Mdx3cv mouse heart expresses a near full-length dystrophin at ~3.3% of the wild type level (Wasala et al Journal of Molecular and Cellular Cardiology 102:45-52, 2017).

Figure 7:
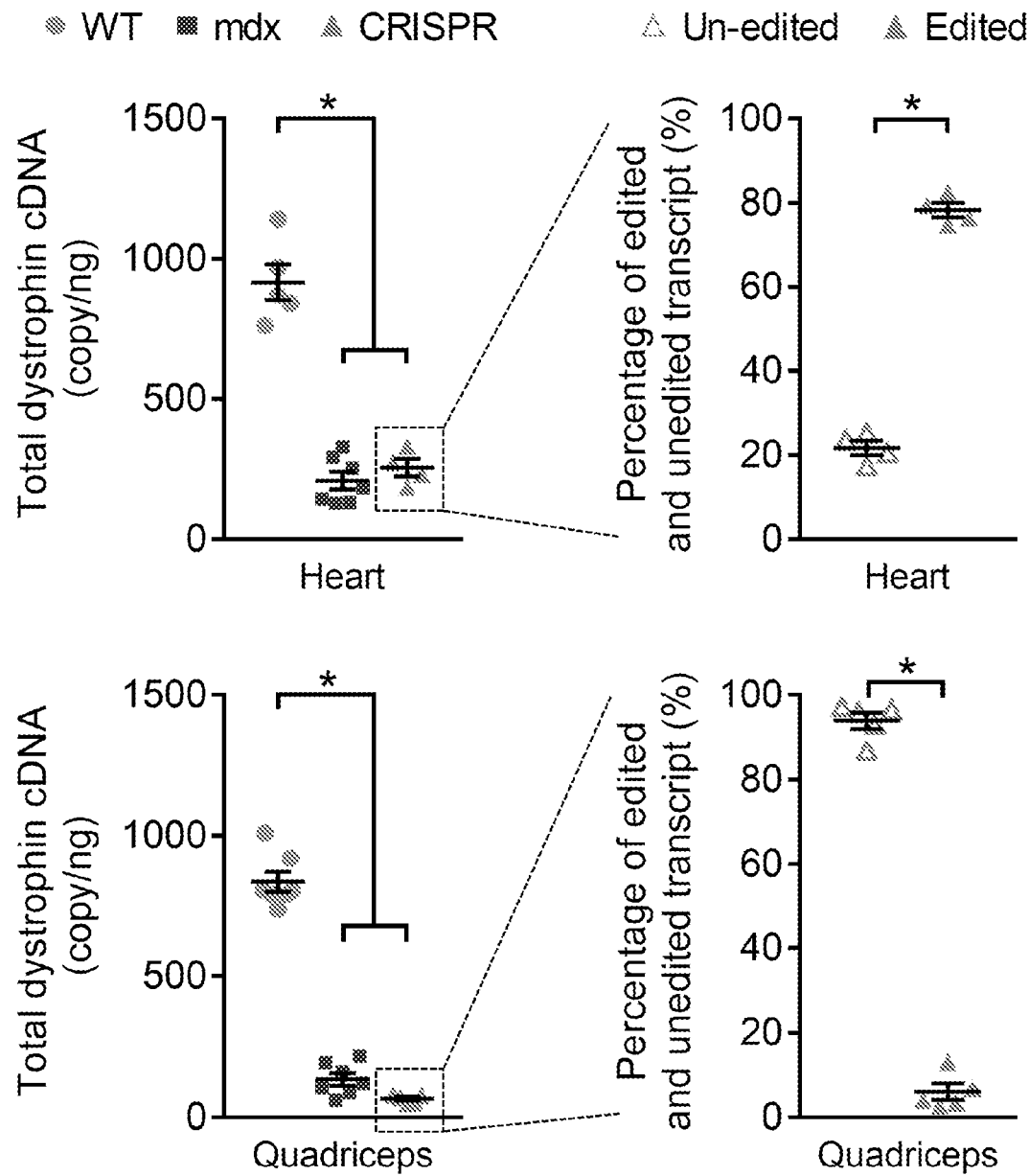
FIG. 7: Quantification of the dystrophin transcript in the heart (top panels) and quadriceps (bottom panels) by droplet digital PCR. Left panels depict total dystrophin transcript levels (product B) per ng of cDNA. Right panels depict the percentage of unedited (product A)/(product B) and edited (product C)/(product B) dystrophin transcripts in CRISPR treated mdx mice (see FIG. 2). Asterisk, statistically significant ($p<0.05$).

The level of gene editing that occurred in animals treated with CRISPR was quantified by calculating the percentage of unedited transcript relative to the percentage of edited transcript in the heart and quadriceps of each animal. Edited and unedited transcripts were quantified using droplet digital PCR (FIG. 2). FIG. 7 show total levels of dystrophin cDNA in the heart (top panels) and quadriceps (bottom panels) of WT animals (circles), mdx untreated animals (squares) and CRISPR treated mdx animals (triangles). The percentage of edited relative to un-edited transcripts are shown in the panels on the right. Left panels depict total dystrophin transcript levels (product B) per ng of cDNA. Right panels depict the percentage of unedited (product A)/(product B) and edited (product C)/(product B) dystrophin transcripts in CRISPR treated mdx mice. Consistent with immunostaining and western blot results, most of the transcripts in the heart of CRISPR treated mdx mice were edited while most of the transcripts in the quadriceps of CRISPR treated mdx mice were unedited. Asterisk, statistically significant ($p<0.05$). It should be pointed out that the total dystrophin transcript in mdx mice was significantly lower than that in wild type mice. This is due to nonsense-mediated decay of the mutated dystrophin transcript in mdx mice (Kerr, 2001) and (Miller, 2014).

Figure 8A:
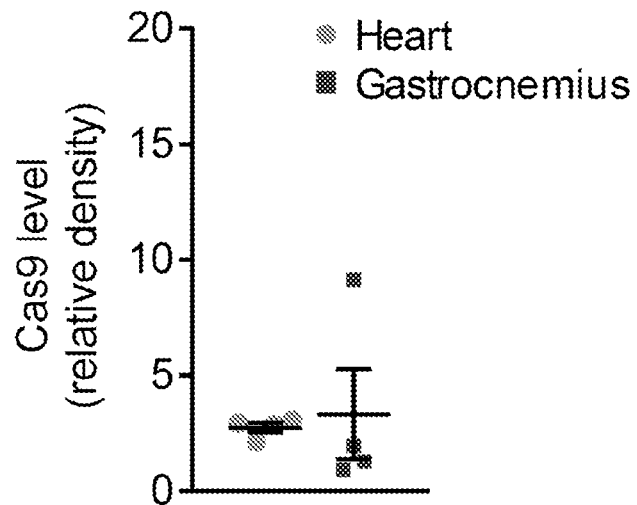
FIG. 8A shows a quantitation of a Cas9 protein western blot in the heart and gastrocnemius of CRISPR treated mdx mice in the 2:1 study.
Figure 8B:
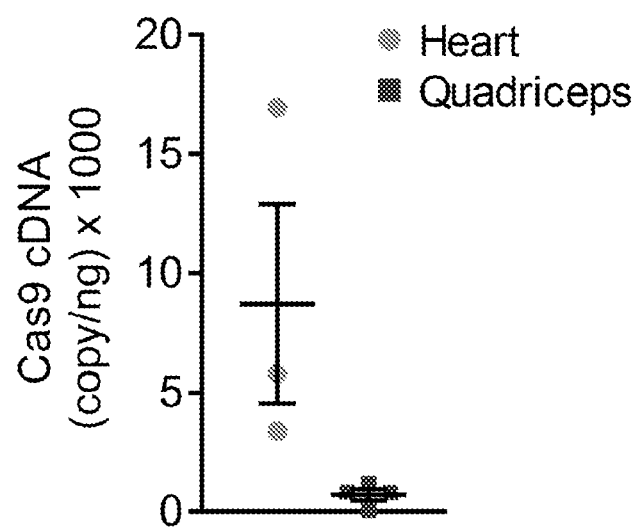
FIG. 8B shows a quantification of the Cas9 transcript via digital droplet PCR in the heart and quadriceps of CRISPR treated mdx mice in the 2:1 study.

To ensure that Cas9 was expressed equally across tissue types, a droplet digital PCR quantification of the Cas9 transcript was performed. The results showing the relative density of Cas9 in the heart vs. the gastrocnemius and the total amount of Cas9 cDNA in the heart vs. the quadriceps are shown in FIG. 8A and FIG. 8B respectively. No significant difference was noted for Cas9 expression between the heart and quadriceps.

Figure 9A:
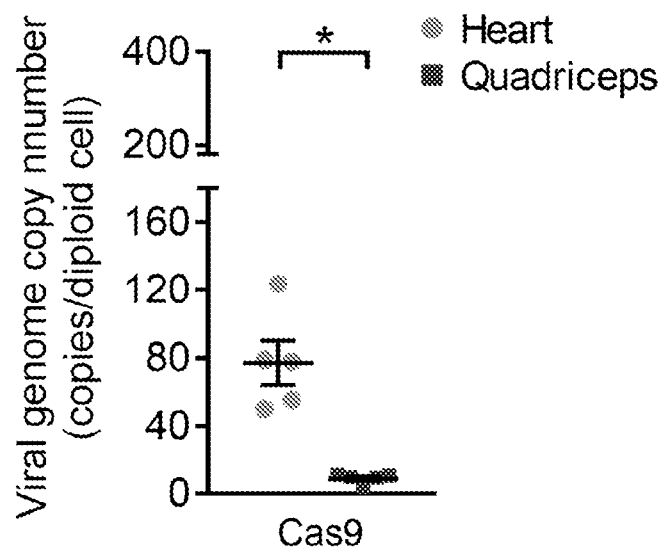
FIG. 9A depicts the quantitative evaluation of the Cas9 genome copy number by TaqMan PCR in the heart and quadriceps of treated mice in the 2:1 study. Asterisk, statistically significant ($p<0.05$).
Figure 9B:
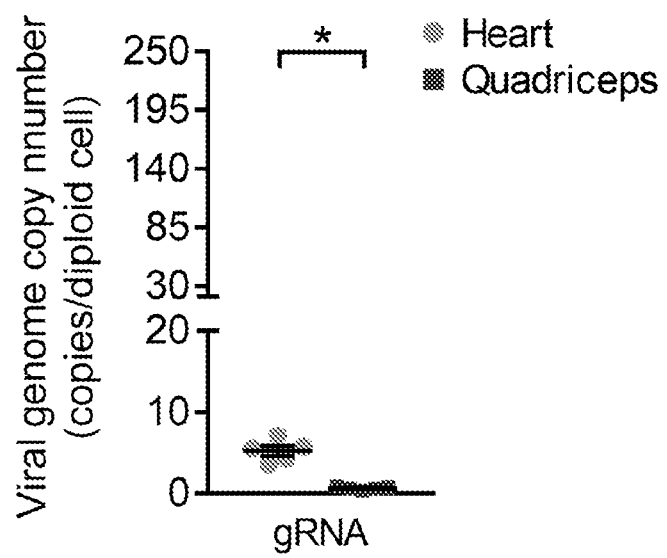
FIG. 9B depicts the quantitative evaluation of the gRNA vector genome copy number by TaqMan PCR in the heart and quadriceps of treated mice in the 2:1 study. Asterisk, statistically significant ($p<0.05$).
Figure 10:
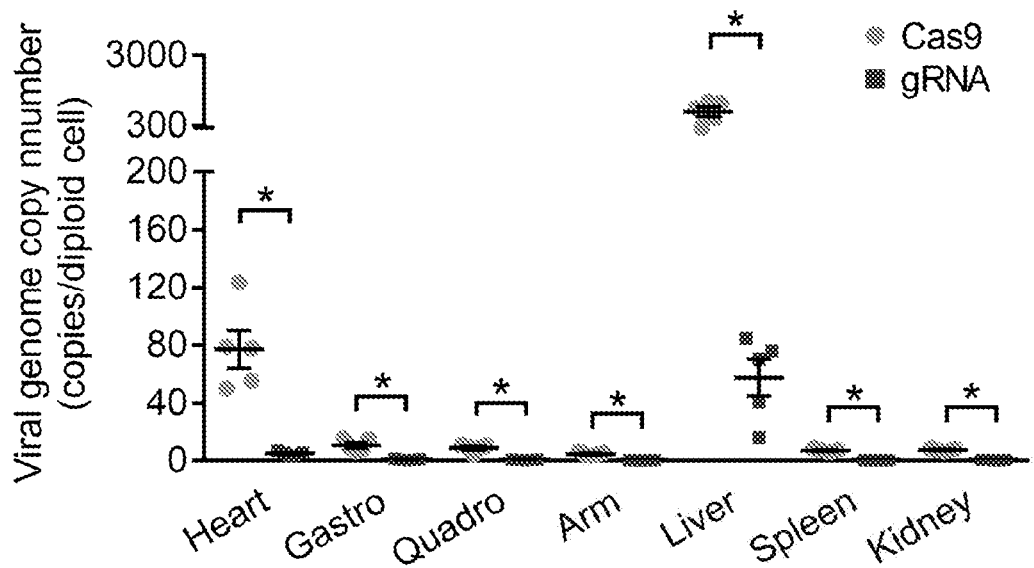
FIG. 10 is a plot depicting the viral genome copy numbers for Cas9 and gRNA in different tissues in the 2:1 study. Asterisk, statistically significant ($p<0.05$).
Figure 11:
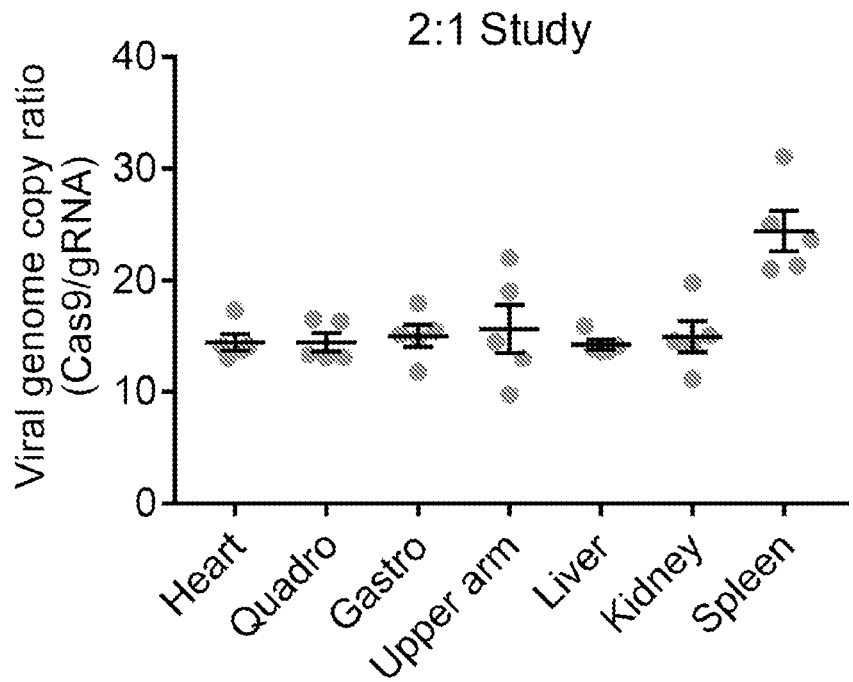
FIG. 11 depicts viral genome copy number ratios (Cas9/ gRNA) in the 2:1 study.

The AAV genome copy number of both the Cas9 vector and the gRNA vector were quantitatively evaluated by Taqman PCR. The results are shown in FIG. 9A-9B. FIG. 9A shows the viral copy number of the Cas9 vector in the heart vs. the quadriceps and FIG. 9B shows the viral copy number of the gRNA vector in the heart vs. the quadriceps. For both vectors, the viral genome copy in the heart was significantly higher than that in the quadriceps. Despite the fact that the Cas9 vector genome copy number in that heart was significantly higher than that of the quadriceps, two tissues showed similar levels of Cas9 expression at the RNA level and protein level (see FIGS. 8A and 8B). Since the potency of the CMV promoter varies in different types of tissues and cells (Qin et al PLOS One 5:e10611, 2010), it is very likely that the CMV promoter was stronger in the quadriceps than it was in the heart in the context of our study. Asterisk, statistically significant ($p<0.05$). FIG. 10 shows results from the same experiment using TaqMan PCR to quantify vector copy numbers. Viral copy number of Cas9 to gRNA was determined across different tissues (including the heart, gastrocnemius, quadriceps, arm muscle, liver, spleen and kidney). In all the tissues examined, the genome copy number of the Cas9 vector was significantly higher than that of the gRNA vector. Asterisk, statistically significant ($p<0.05$). The Cas9 vector-to-gRNA vector genome copy ratio reached approximately 12-14 in muscles and internal organs (FIG. 11). This was approximately 6 to 7 fold higher than the expectation based on the vector dose at the time of AAV injection (Table 2).

Figure 12:
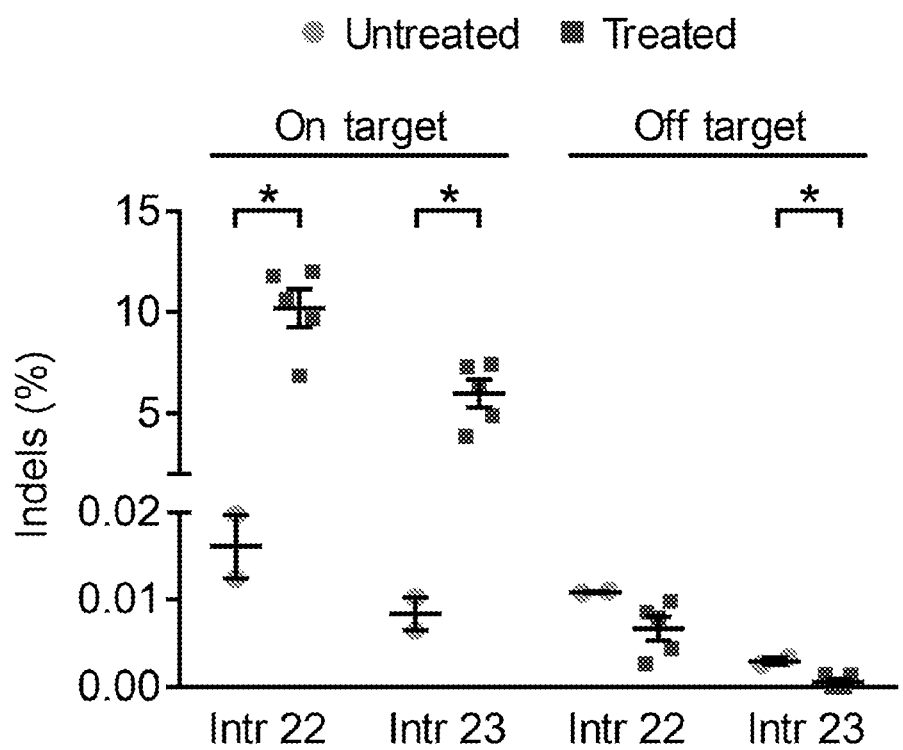
FIG. 12 is a scatterplot quantifying indels detected by deep sequencing in on-target and off-target locations in treated and untreated animals in the 2:1 study. Asterisk, statistically significant ($p<0.05$).

Deep sequencing of the target sites and predicted off-target sites was performed in untreated and CRISPR treated mdx mice. The results are shown in FIG. 12 and reveal that significant on-target editing was observed for both gRNAs only in CRISPR treated mdx mice. Off target editing was not detected with either gRNA. Asterisk, statistically significant ($p<0.05$).

Figure 13:
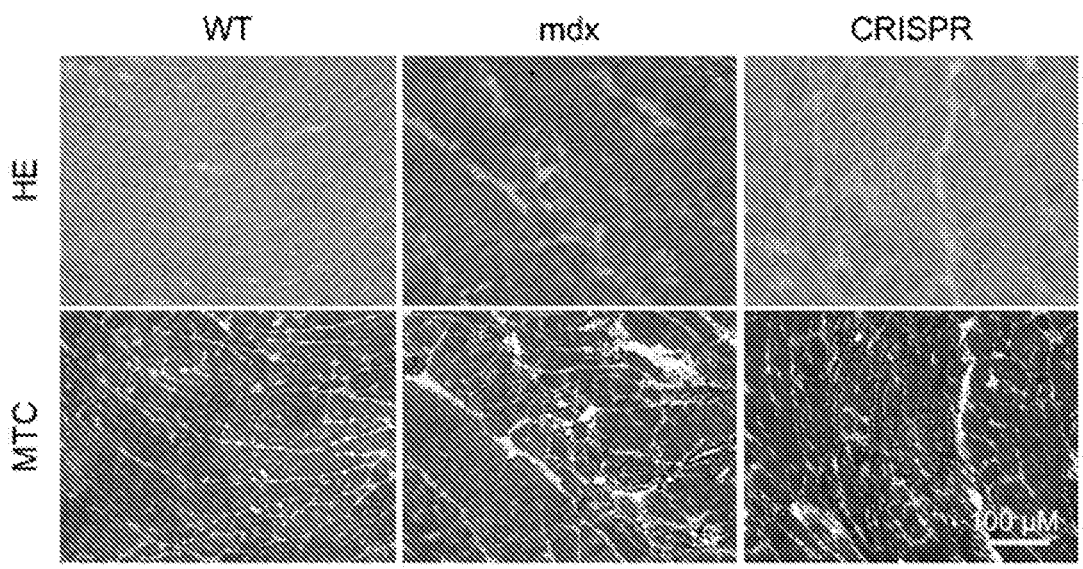
FIG. 13 depicts representative hematoxylin and eosin (HE) and Masson trichrome (MTC) stains of heart muscle obtained from treated and untreated animals in the 2:1 study.
Figure 14A:
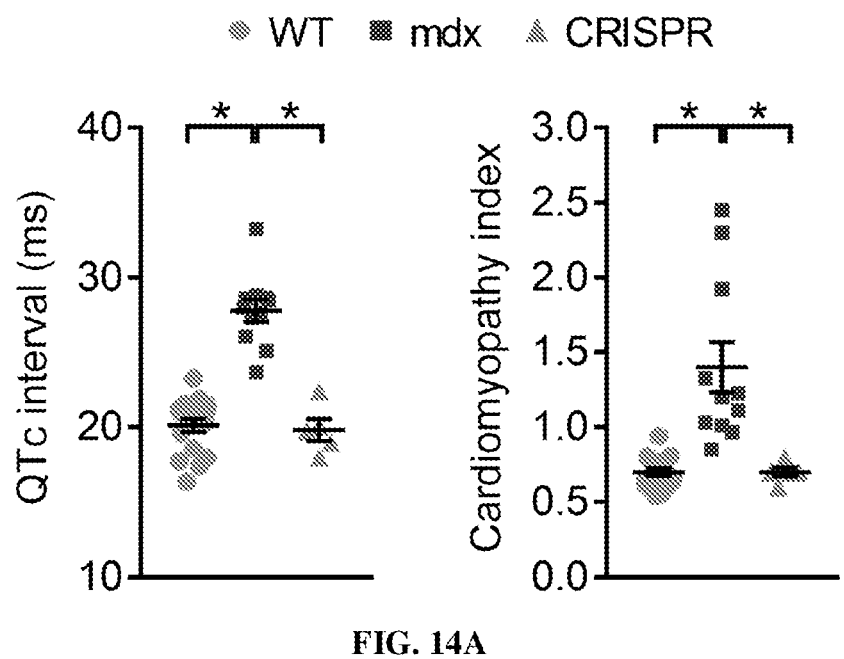
FIG. 14A depicts a quantitative evaluation of Mitchell corrected QT (QTc) interval and cardiomyopathy index in treated and untreated mice in the 2:1 study. Asterisk, statistically significant ($p<0.05$).
Figure 14B:
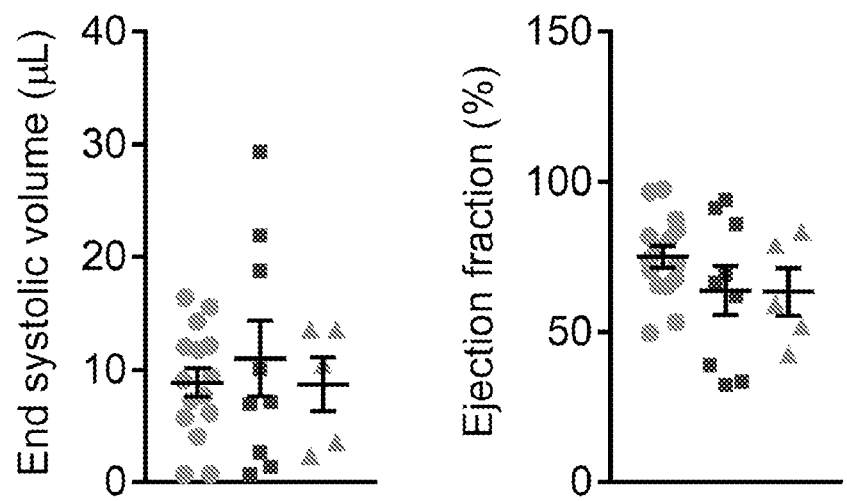
FIG. 14B depicts a quantitative evaluation of end systolic volume and ejection fraction in treated and untreated mice in the 2:1 study.
Figure 15:
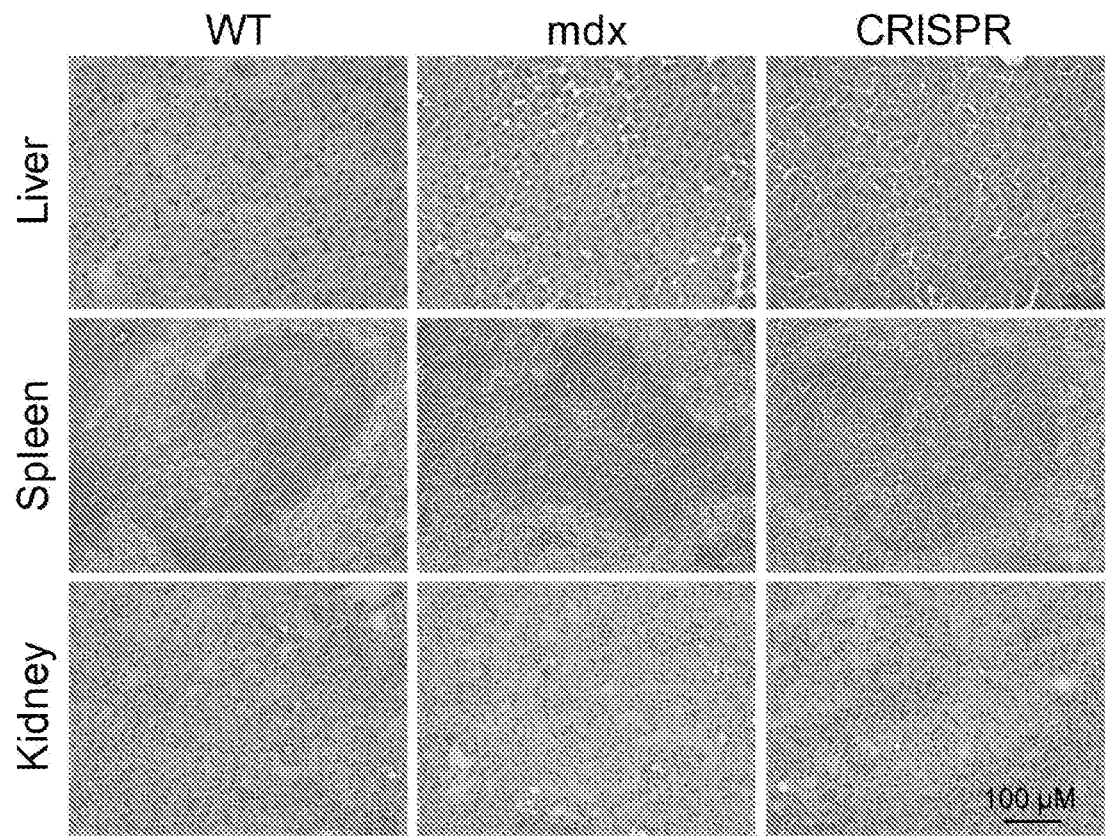
FIG. 15 depicts representative histology images from the liver, spleen and kidney in the 2:1 study.

Heart histology in wildtype (WT), untreated (mdx) and treated (CRISPR) animals was evaluated using hematoxylin and eosin (HE) and Masson trichrome (MTC) staining. The results are shown in FIG. 13. Similar pathology and fibrosis were detected in the hearts of untreated and CRISPR-treated mdx mice. Therefore, cardiac histology was not improved in the 2:1 study. Heart function was measured using Mitchell corrected QT (QTc) interval and cardiomyopathy index (FIG. 14A). End systolic volume and ejection fraction were also measured (FIG. 14B). CRISPR therapy significantly improved the QTc interval and cardiomyopathy index but not the end systolic volume and ejection fraction. Asterisk, statistically significant ($p<0.05$). Therefore, heart function was not improved by this 2:1 study. As a control, the histology of the liver, spleen and kidney were also performed. No obvious abnormalities were detected among wildtype, mdx and CRISPR treated mdx mice (FIG. 15).

The anatomic properties of the mice in this study were also measured. Table 6, below depicts the body weight (BW), heart weight (HW), tibialis muscle weight (TW) and ventricle weight (VW) of the mice in the study.

TABLE 6

| | WT | mdx | CRISPR |
|---|---|---|---|
| n | 15 | 18 | 5 |
| Age (m) | 18.77 ± 0.35 | 18.85 ± 0.32 | 18.90 ± 0.05 |
| BW (g) | 13.33 ± 0.63 | 31.58 ± 0.95 | 23.74 ± 0.42# |
| HW (mg) | 136.26 ± 2.45 | 132.68 ± 3.78 | 122.62 ± 8.71 |
| VW (mg) | 129.09 ± 2.46 | 122.67 ± 3.03 | 116.60 ± 8.40 |
| TW (mg) | 42.03 ± 1.05 | 52.84 ± 2.92* | 44.45 ± 2.59 |
| HW/BW (mg/g) | 4.11 ± 0.11 | 4.30 ± 0.12 | 5.15 ± 0.29# |
| TW/BW (mg/g) | 1.26 ± 0.03 | 1.61 ± 0.14 | 1.87 ± 0.08 |
| TW/TW (mg/g) | 3.28 ± 0.12 | 2.68 ± 0.17* | 2.77 ± 0.16 |
| VW/BW (mg/g) | 3.89 ± 0.11 | 3.98 ± 0.12 | 4.90 ± 0.28# |
| VW/TW (mg/g) | 3.10 ± 0.11 | 2.47 ± 0.15* | 2.63 ± 0.16 |

*Significantly different from WT
, Significantly different from WT and mdx

Table 7 shows a breakdown of the quantitative evaluation of the ECG parameters in the 2:1 study. It shows the heart rate, PR interval, QRS duration and Q amplitude. The QRS duration of wild type mice was significantly lower than that of mdx mice irrespective of CRISPR therapy. Compared to wild type mice, untreated mdx mice had significantly higher heart rate and shorter PR interval. The absolute value of the Q amplitude in 2:1 CRISPR-treated mdx mice was significantly increased compared to that of wild type mice.

TABLE 7

| Strain | N | Age | Heart rate (bpm) | PR interval (ms) | QRS duration (ms) | Q amplitude (µV) |
|---|---|---|---|---|---|---|
| WT | 18 | 19.26 ± 0.44 | 572.93 ± 8.96 | 40.18 ± 0.65 | 8.09 ± 0.19# | −32.06 ± 4.68 |
| Mdx | 11 | 19.34 ± 0.71 | 617.86 ± 14.33* | 34.97 ± 1.14* | 9.71 ± 0.58 | −60.95 ± 35.89 |
| CRISPR | 5 | 18.78 ± 0.04 | 584.44 ± 10.28 | 38.17 ± 1.05 | 10.33 ± 0.34 | −143.15 ± 31.90* |

*Significantly different from WT
Significantly different from mdx and CRISPR.

Table 8 shows the results of a quantitative evaluation of the heart hemodynamics by the closed-chest cardiac cassette assay in the 2:1 study. No improvement was detected in CRISPR-treated mdx mice. Unexpectedly, the left ventricular diastolic time constant (Tau) was significantly prolonged in treated mice.

TABLE 8

| N | WT 15 | Mdx 9 | CRISPR 5 |
|---|---|---|---|
| Age | 19.72 ± 0.57 | 19.68 ± 0.92 | 18.94 ± 0.02 |
| End diastolic volume (µL) | 30.02 ± 1.78 # | 20.78 ± 2.72 | 20.26 ± 2.37 |
| Max pressure (mmHg) | 103.62 ± 2.08# | 88.00 ± 3.95 | 87.07 ± 7.65 |
| Stroke volume (µL) | 23.47 ± 1.41# | 12.83 ± 0.95 | 12.73 ± 1.27 |
| Cardiac output (mL/min) | 14585.05 ± 885.44# | 7646.23 ± 542.72 | 7480.39 ± 595.40 |
| dP/dt max (KmmHg/sec) | 13163.20 ± 446.52# | 9940.56 ± 990.41 | 9438.80 ± 483.43 |
| dP/dt min (KmmHg/sec) | −12551.40 ± 677.10# | −8507.67 ± 666.57 | −8450.60 ± 568.90 |
| Tau (ms) | 6.30 ± 0.32 | 7.47 ± 0.55 | 9.55 ± 1.45* |

*Significantly different from WT
Significantly different from mdx and CRISPR

Figure 16A:
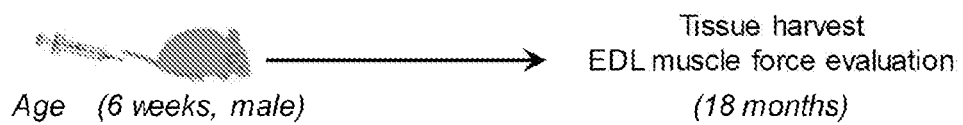
FIG. 16A depicts a schematic overview of a study investigating long-term systemic AAV CRISPR therapy with a Cas9:gRNA vector ratio of 1:3 in male mdx mice.

Example 2: Long-Term Systemic AAV CRISPR Therapy with a Cas9:gRNA Vector Ratio of 1:3 in Male Mdx Mice In this example, a long term AAV CRISPR therapy was performed in male mdx mice using a ratio of 1:3 Cas9:gRNA vectors. FIG. 16A shows a schematic overview of the study. Six 6-week-old male mdx mice were co-injected with the Cas9 vector and gRNA vector at the dose of $1\times10^{13}$ and $3\times10^{13}$ vg/mouse ($4.6\times10^{14}$ and $13.8\times10^{14}$ vg/kg), respectively. Dystrophin expression, AAV transduction and disease rescue was evaluated at 18 months of the age. Age/sex-matched normal BL10 (wild type, WT) mice and untreated mdx mice were used as controls.

Figure 16B:
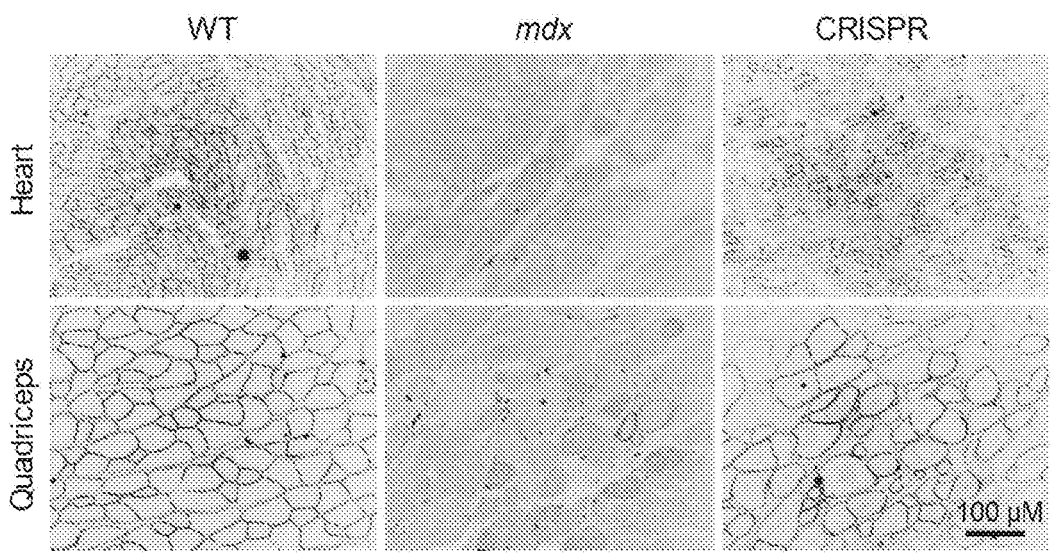
FIG. 16B shows representative dystrophin immunostaining photomicrographs from the heart and quadriceps of untreated and treated mice in the 1:3 male mdx mice study.
Figure 16C:
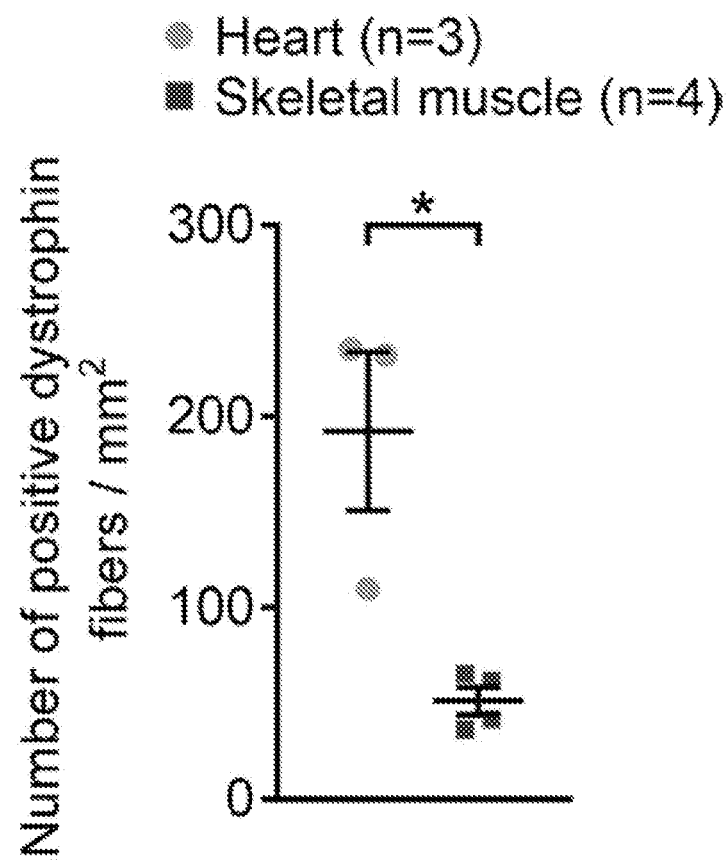
FIG. 16C shows the number of dystrophin positive fibers detected in heart and skeletal muscle (quadriceps) in treated and untreated mice in the 1:3 male mdx mice study.
Figure 16D:
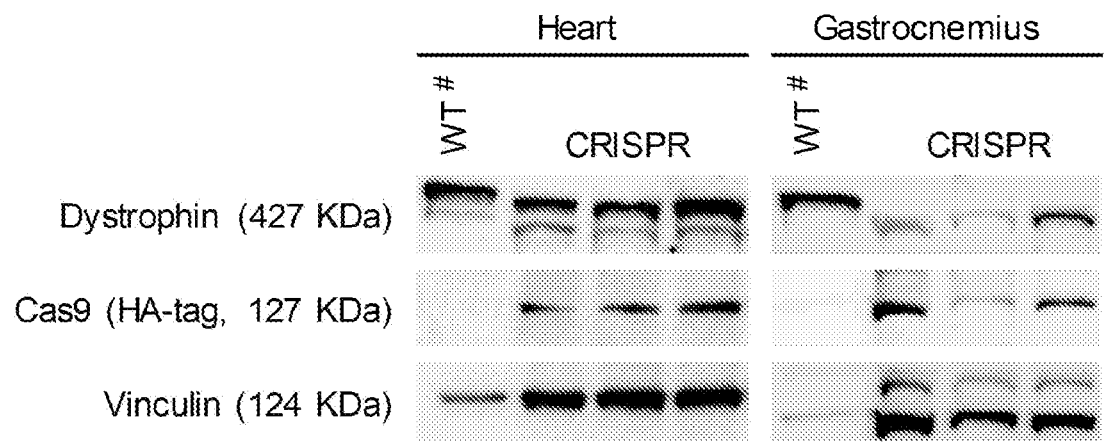
FIG. 16D shows representative dystrophin and Cas9 western blots from the heart and gastrocnemius of untreated and treated mice in the 1:3 male mdx mice study. Vinculin western was included as the loading control. Pound sign (#), loading is different in this lane.
Figure 16E:
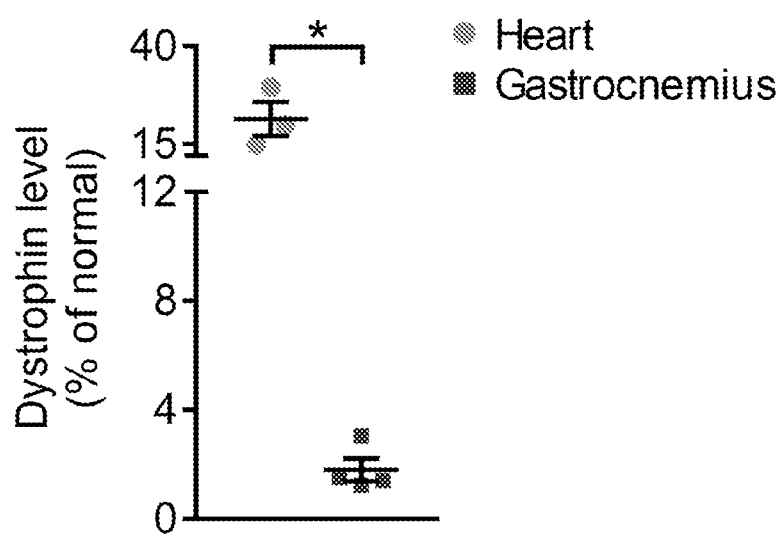
FIG. 16E shows the LICOR quantification of dystrophin western blot in the 1:3 male mx mice study. Asterisk (*), statistically significant (p<0.05).

FIG. 16B shows representative dystrophin immunostaining photomicrographs from the heart and quadriceps. Abundant dystrophin positive myocytes were detected in both heart and quadriceps (skeletal muscle) in CRISPR treated mice (FIG. 16C). FIG. 16D shows representative dystrophin and Cas9 western blots from the heart and gastrocnemius. Vinculin western was included as the loading control. The western blots showed that dystrophin reached approximately 20% in the heart and approximately 2% in skeletal muscles. Dystrophin expression was readily detected in both heart and quadriceps in CRISPR treated mice. FIG. 16E shows the LICOR quantification of dystrophin western blot. Asterisk (*), statistically significant ($p<0.05$). Pound sign (#), loading is different in this lane.

Figure 17A:
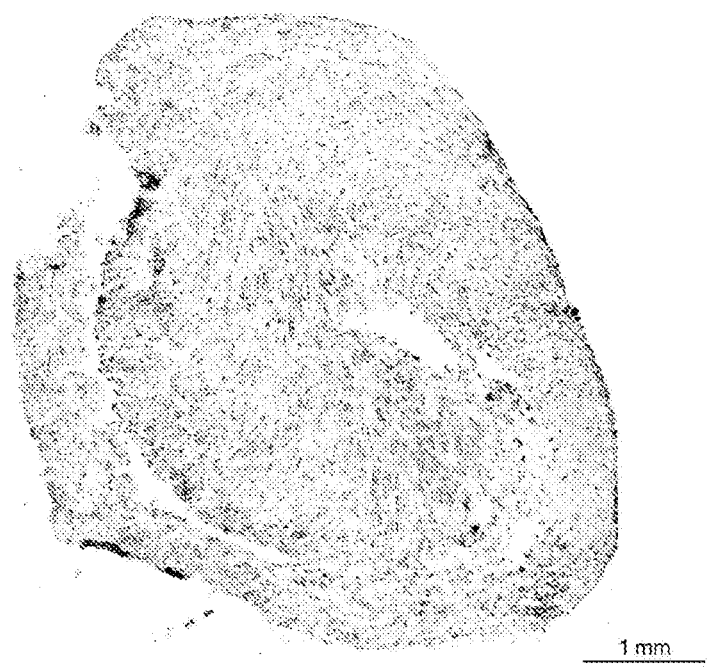
FIG. 17A shows a representative full-view dystrophin immunostaining photomicrographs from the heart of a mouse treated with the 1:3 Cas9:gRNA CRISPR ratio.
Figure 17B:
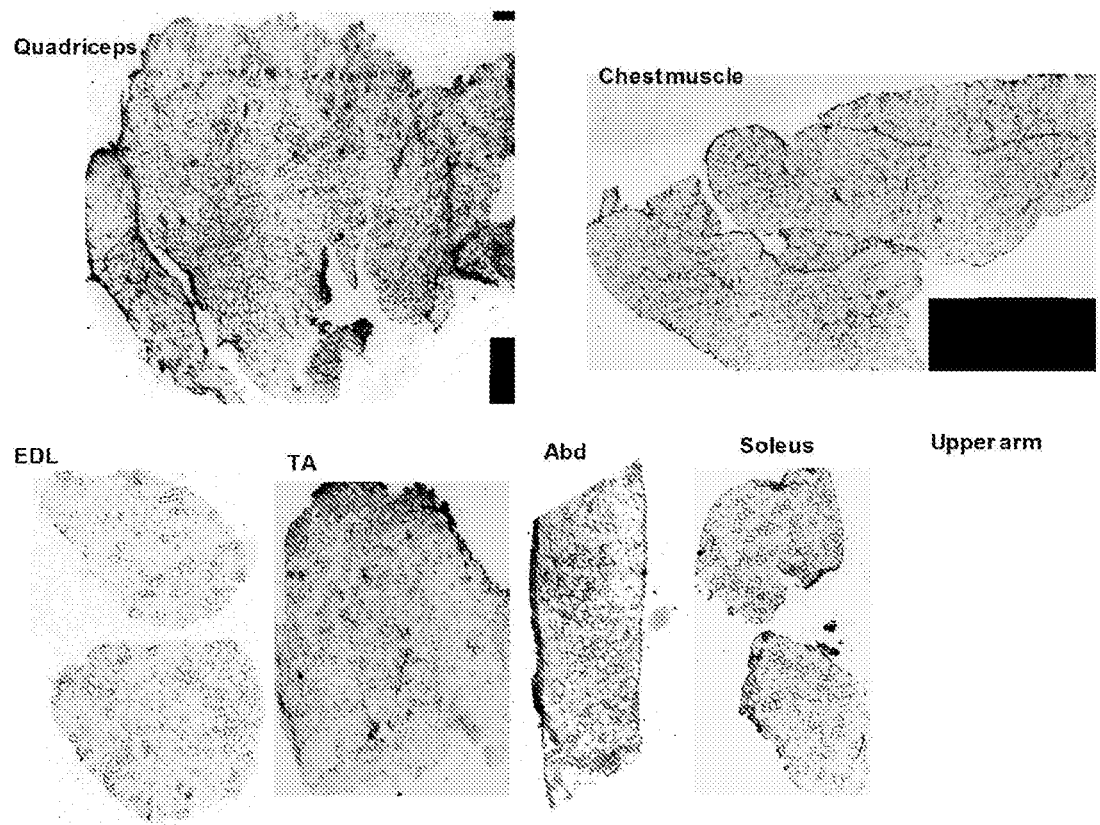
FIG. 17B shows representative full-view dystrophin immunostaining photomicrographs from quadriceps (Quadro), chest muscle, extensor digitorum longus (EDL), tibialis anterior (TA), abdominal muscle, soleus, upper arm muscle and tongue taken from a treated mouse in the male 1:3 study.

Similar to Example 1, the level of dystrophin expression was measured throughout the body of treated and untreated animals. FIG. 17A shows representative full-view dystrophin immunostaining photomicrographs from the heart of a CRISPR treated animal while FIG. 17B shows representative full-view dystrophin immunostaining photomicrographs from quadriceps (Quadro), chest muscle, extensor digitorum longus (EDL), tibialis anterior (TA), abdominal muscle, soleus, upper arm muscle and tongue of the same animal. Robust expression of dystrophin is visible throughout the musculature.

Figure 18:
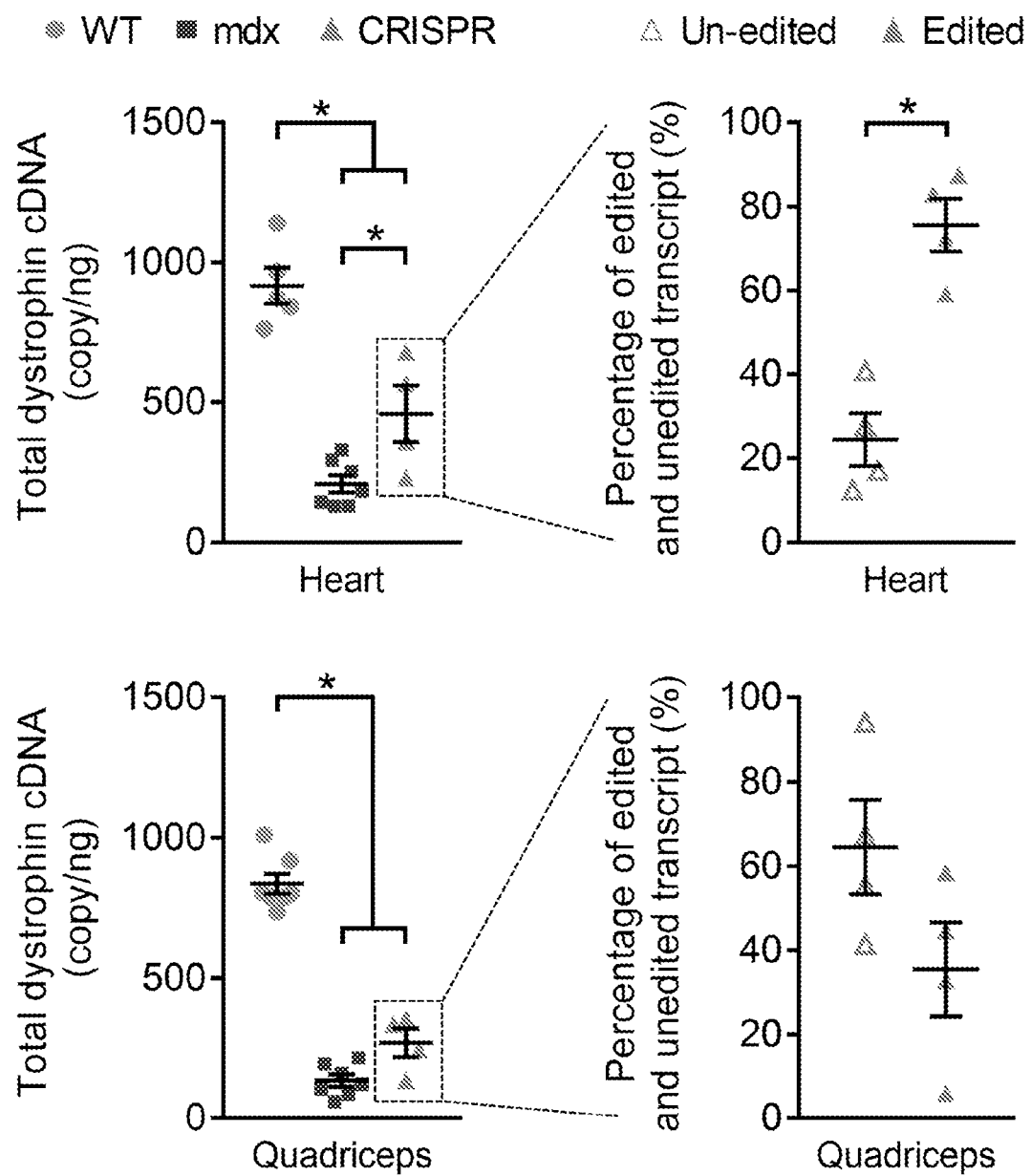
FIG. 18 shows the quantification of the dystrophin transcript in the heart (top panels) and quadriceps (bottom panels) by droplet digital PCR in the male 1:3 study. Left panels depict total dystrophin transcript levels per ng of cDNA. Right panels depict the percentage of unedited and edited dystrophin transcripts in CRISPR treated mdx mice. Asterisk, statistically significant (p<0.05).
Figure 19A:
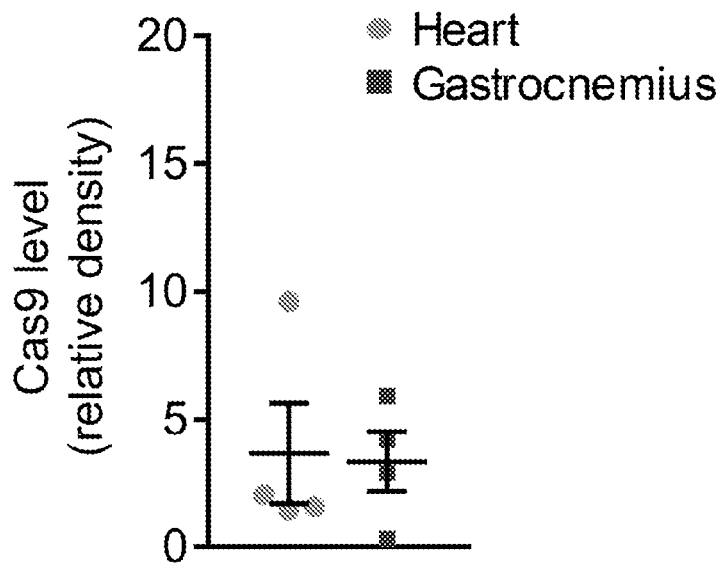
FIG. 19A shows the quantitative evaluation of Cas9 expression in the male 1:3 study by protein western blot.
Figure 19B:
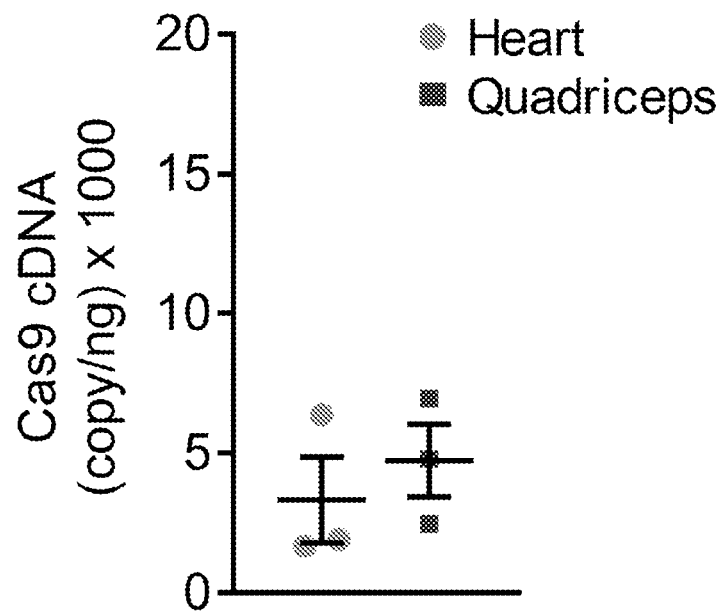
FIG. 19B shows the quantitative evaluation of Cas9 expression in the male 1:3 study by digital droplet PCR quantification of the Cas9 transcript.

Quantification of the dystrophin transcript in the heart and quadriceps of WT, treated (CRISPR) and untreated (mdx) animals was performed by droplet digital PCR. FIG. 18, left panels, depict total dystrophin transcript levels per ng of cDNA in the heart. Right panels depict the percentage of unedited and edited dystrophin transcripts in CRISPR treated mdx mice. Consistent with western blot results, in the heart of CRISPR treated mdx mice (top panels), the level of total dystrophin transcripts was significantly higher than that of mdx mice but lower than that of wild type mice. Further, the percentage of edited transcripts was significantly higher than that of unedited transcripts. Specifically, 80% of those transcripts were corrected by CRISPR editing. In contrast to Example 1, approximately 30% of the dystrophin transcripts were edited in skeletal muscles (FIG. 16, bottom panels). Asterisk, statistically significant ($p<0.05$). As a control, levels of Cas9 protein in the heart and in the gastrocnemius were found to be equivalent by western blot (FIG. 19A). Also, similar levels of Cas9 expression were determined by digital droplet PCR quantification of the Cas9 transcript in the heart and quadriceps (FIG. 19B).

Figure 20A:
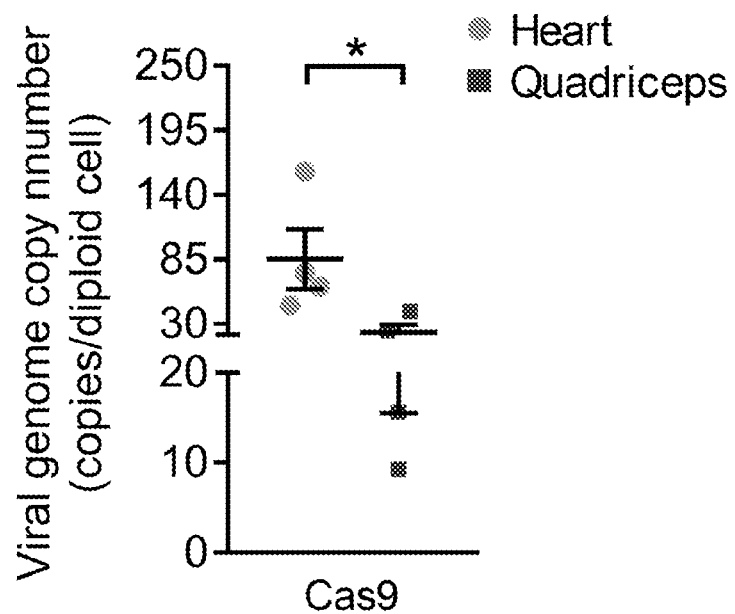
FIG. 20A shows the quantitative evaluation of the Cas9 vector genome copy number by TaqMan PCR in the male 1:3 study. Asterisk, statistically significant (p<0.05).
Figure 20B:
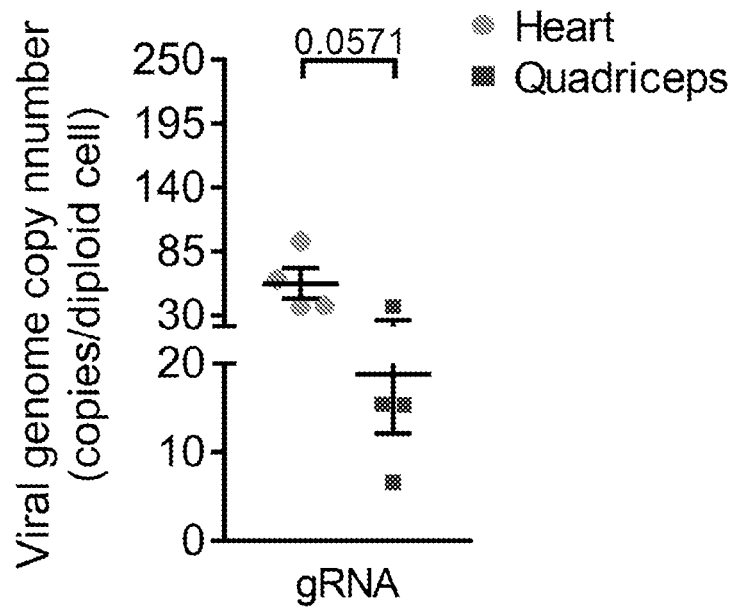
FIG. 20B shows the quantitative evaluation of the gRNA vector genome copy number by TaqMan PCR in the male 1:3 study.
Figure 21:
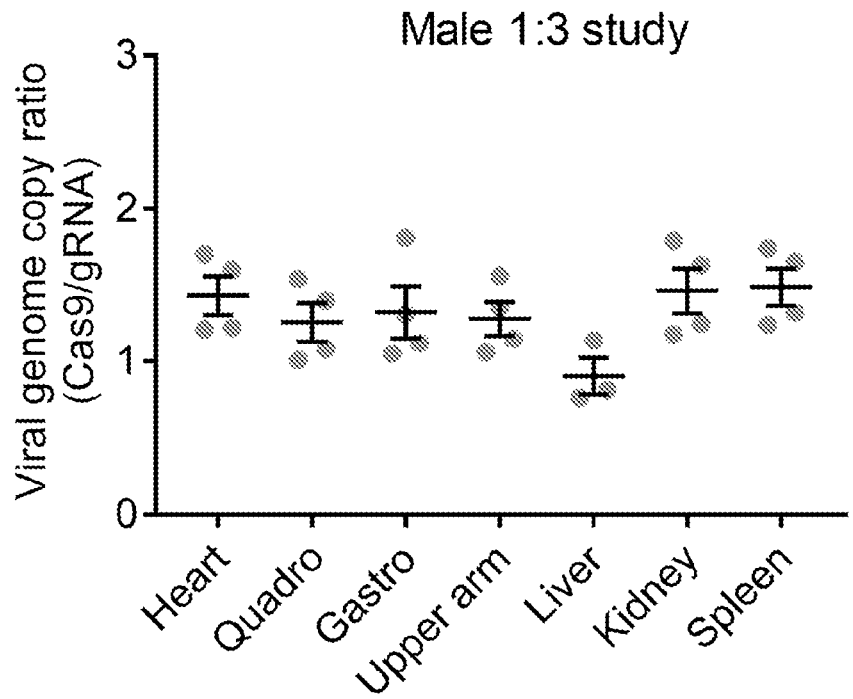
FIG. 21 depicts viral genome copy number ratios (Cas9/gRNA) in the male 3:1 study

A quantitative evaluation of the AAV genome copy number by TaqMan PCR was then performed. FIG. 20A depicts the quantification of the Cas9 vector genome copy number and FIG. 20B depicts the quantification of the gRNA vector genome copy number in the heart and quadriceps. For the Cas9 vector, the viral genome copy in the heart was significantly higher than that in the quadriceps. For the gRNA vector, the viral genome copy in the heart was higher than that in the quadriceps (p=0.057). Despite the fact that the Cas9 vector genome copy number in that heart was significantly higher than that of the quadriceps, two tissues showed similar levels of Cas9 expression at the RNA level and protein level (see FIGS. 19A and 19B). Since the potency of the CMV promoter varies in different types of tissues and cells (Qin et al PLOS One 5:e10611, 2010), it is very likely that the CMV promoter was stronger in the quadriceps than it was in the heart in the context of our study. Asterisk, statistically significant (p<0.05). Encouragingly, the Cas9 vector-to-gRNA vector genome copy number ratio was close to 1 in every tissue examined (FIG. 21).

Figure 22:
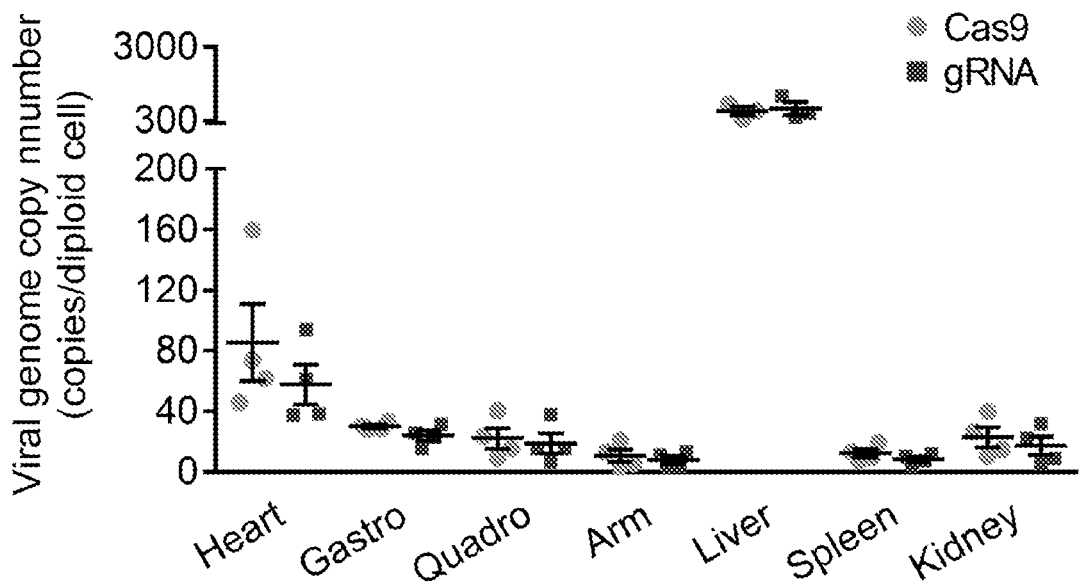
FIG. 22 is a scatter plot depicting viral genome copy number of Cas9 and gRNA across different tissues in the male 1:3 study.

To confirm the findings above, the quantitative evaluation of the AAV genome copy number using TaqMan PCR was extended to DNA extracted from the heart, gastrocnemius, quadriceps, arm muscle, liver, spleen and kidney. As shown in FIG. 22, similar levels of the Cas9 vector and the gRNA vector genome copy numbers were detected in all the tissues examined.

Figure 23:
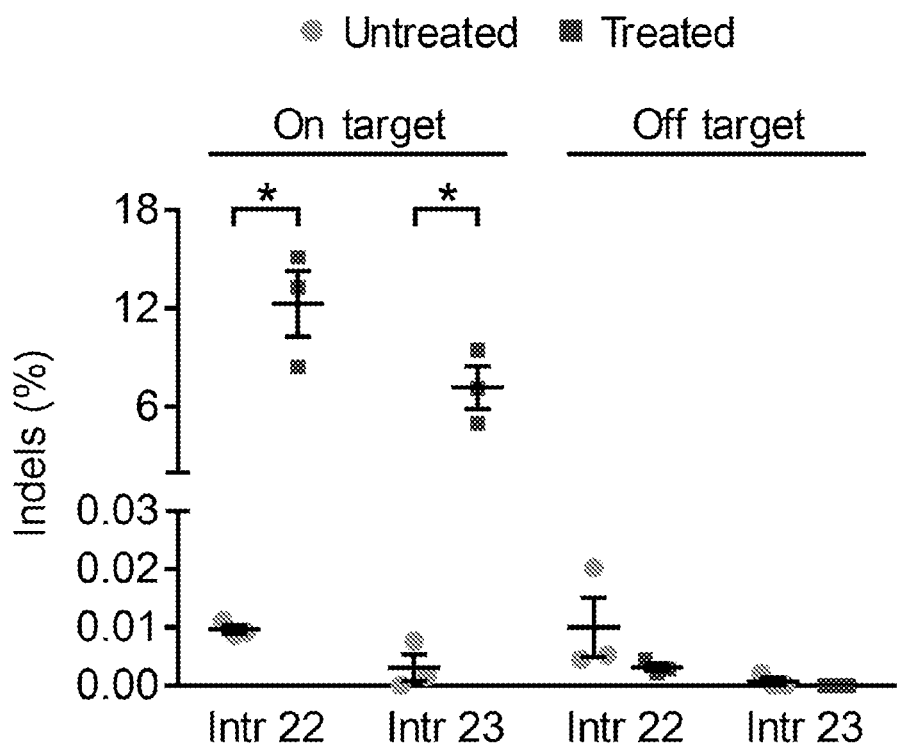
FIG. 23 is a scatter plot quantifying indels identified by deep sequencing in on-target and off-target sites in untreated and CRISPR treated mdx mice (male 1:3 study). Asterisk, statistically significant (p<0.05).

To quantify insertions/deletions (indels) in CRISPR treated mdx mice, deep sequencing was performed at both on target and predicted off-target sites was performed in both untreated and CRISPR treated mdx mice. The results are shown in FIG. 23. Significant on-target editing was observed for both gRNAs only in CRISPR treated mdx mice. Off-target editing was not detected with either gRNA. Asterisk, statistically significant (p<0.05).

Figure 24A:
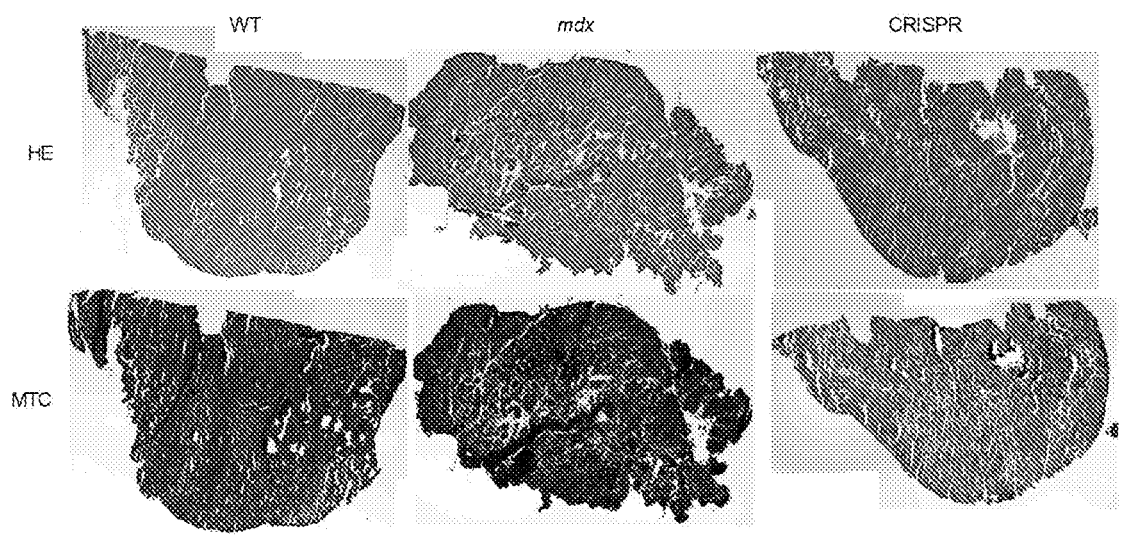
FIG. 24A depicts representative full-view photomicrographs of skeletal muscle taken from mice in the male 1:3 study stained with by hematoxylin and eosin (HE) and Masson trichrome (MTC).
Figure 24B:
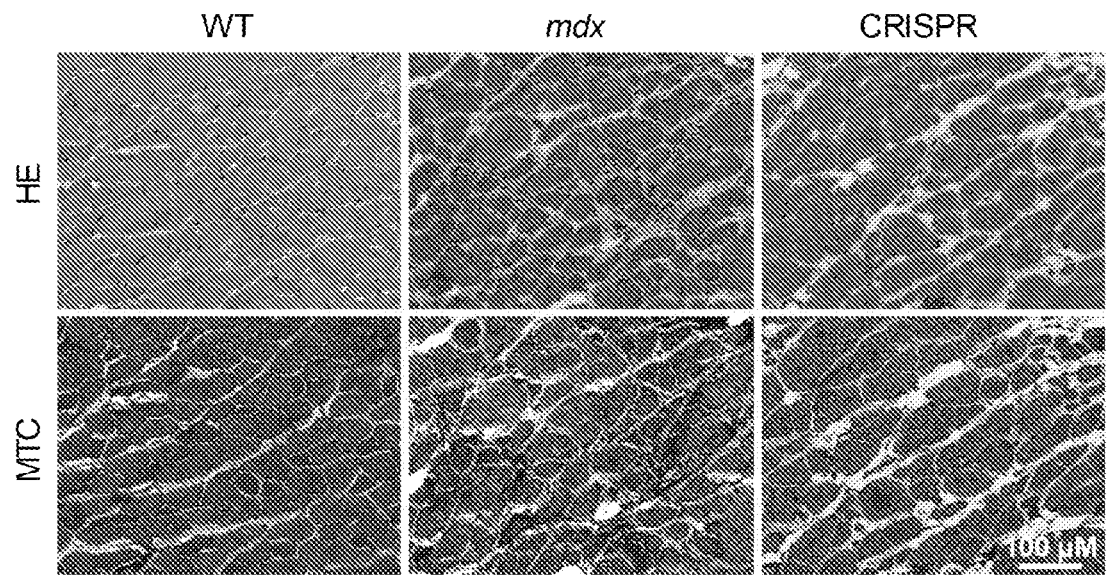
FIG. 24B depicts representative high magnification view photomicrographs of skeletal muscle taken from mice in the male 1:3 study stained with by hematoxylin and eosin (HE) and Masson trichrome (MTC).
Figure 24C:
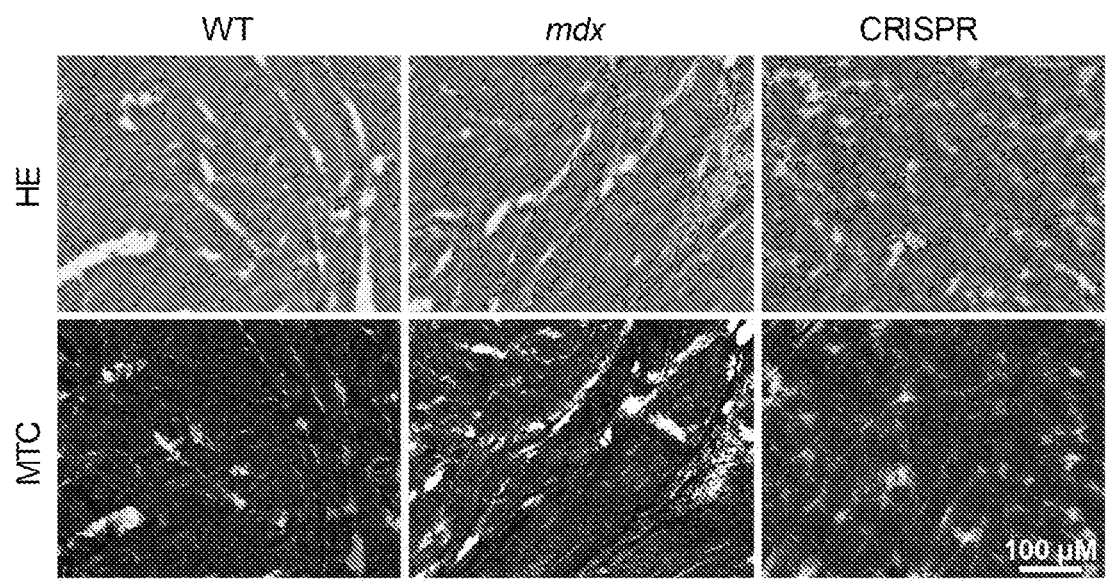
FIG. 24C depicts representative heart histology images by hematoxylin and eosin (HE) and Masson trichrome (MTC) staining in the male 1:3 study.
Figure 25:
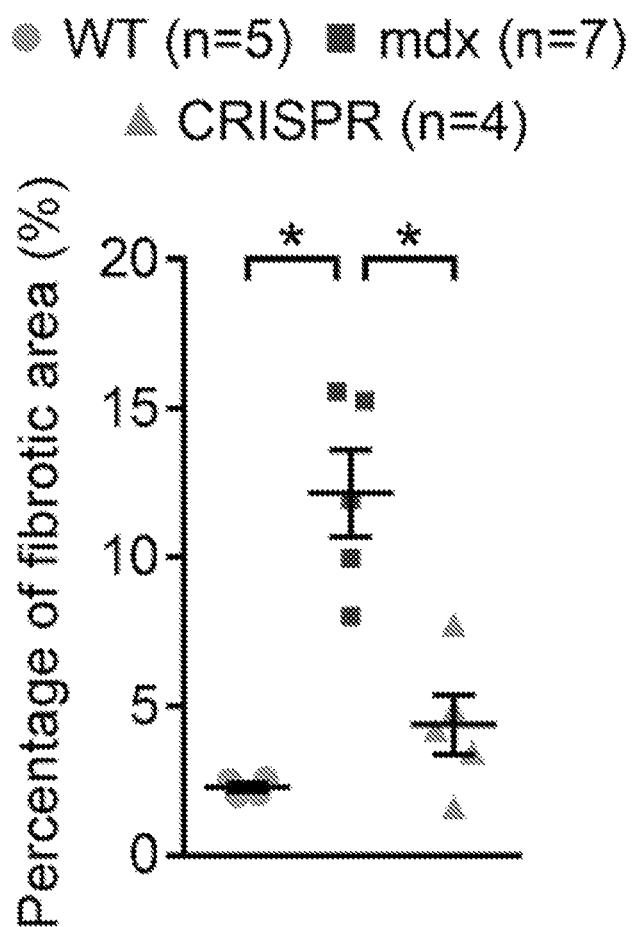
FIG. 25 depicts the percentage of fibrotic area in skeletal muscle taken from mice in the male 1:3 study.

The effect of CRISPR editing on skeletal muscle fibrosis and heart muscle fibrosis was assessed by evaluating skeletal and myocardial muscle histology by hematoxylin and eosin (HE) staining and Masson trichome (MTC). FIG. 24A shows representative full-view photomicrographs of stained skeletal muscle tissue from wildtype, mdx untreated, and CRISPR mdx animals. FIG. 24B show representative high magnification view photomicrographs of the same tissue. FIG. 24C shows representative high magnification view photomicrographs of stained myocardial muscle in these animals. As shown in these figures, CRISPR treatment greatly attenuated both skeletal muscle fibrosis and myocardial muscle fibrosis (quantified for skeletal muscle in FIG. 25).

Table 9 below shows the anatomic properties of the extensor digitorum longus (EDL) muscle in this study. The muscle weight, optimal muscle length (Lo) and muscle cross-sectional area (CSA) of the untreated mdx mice were significantly higher than those of wild type and CRISPR treated mdx mice. Pathologic muscle hypertrophy in mdx mice was mitigated.

TABLE 9

| Strain | N | EDL weight | Lo | CSA |
|---|---|---|---|---|
| WT | 7 | 12.62 ± 0.29 | 13.16 ± 0.05 | 2.06 ± 0.05 |
| mdx | 12 | 16.13 ± 0.64 # | 13.99 ± 0.11 # | 2.48 ± 0.09 # |
| CRISPR | 6 | 12.14 ± 0.85 | 13.40 ± 0.15 | 1.95 ± 0.14 |

Significantly different from BL10 and CRISPR

Figure 26A:
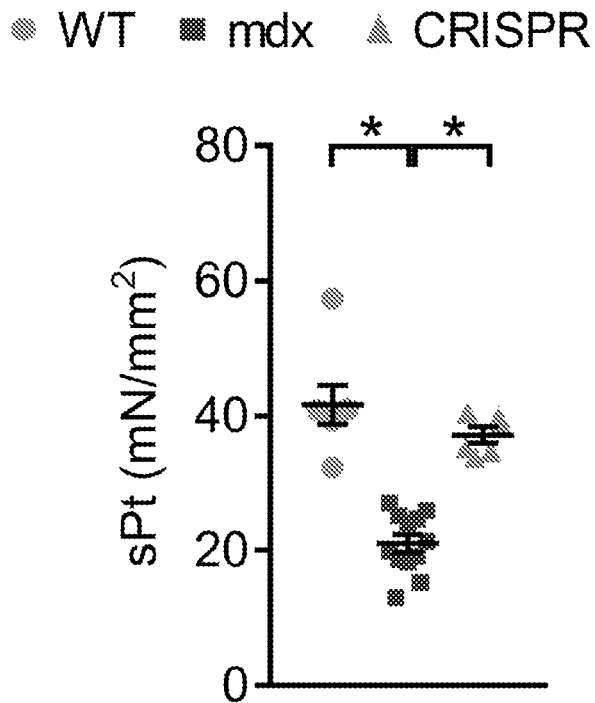
FIG. 26A shows results of the evaluation of skeletal muscle function in the male 1:3 study by ex vivo measurement of the specific twitch force in the extensor digitorum longus (EDL).
Figure 26B:
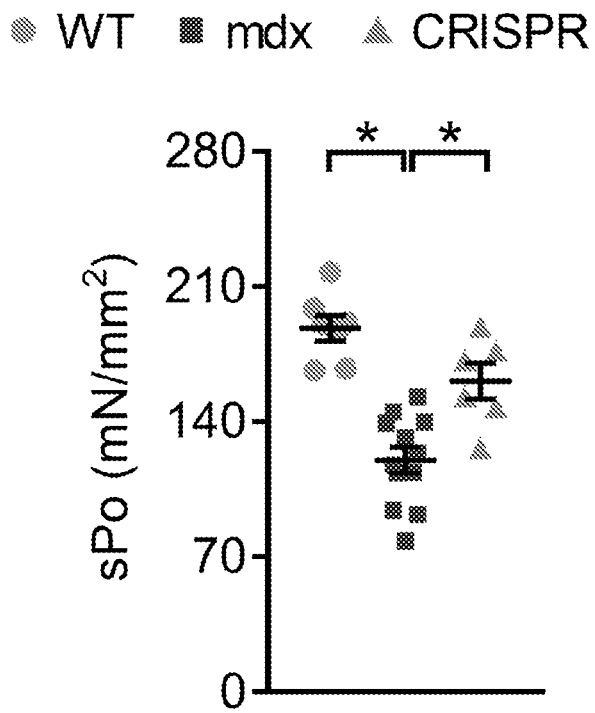
FIG. 26B shows results of the evaluation of skeletal muscle function in the male 1:3 study by ex vivo measurement of the specific tetanic force in the extensor digitorum longus (EDL).
Figure 26C:
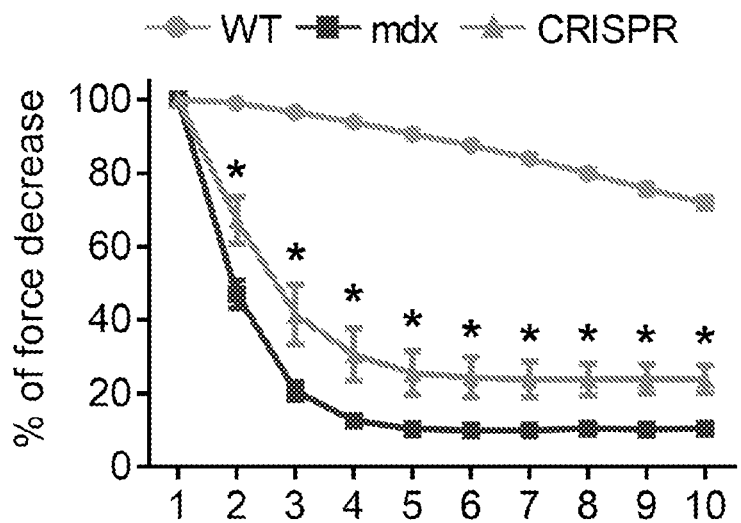
FIG. 26C shows the eccentric contraction profile of skeletal muscle from mice in the male 1:3 study. Asterisk, statistically significant (p<0.05).

To determine the physical effects of CRISPR modification on treated animals, skeletal muscle function was evaluated by ex vivo measurement of the muscle force in the extensor digitorum longus (EDL). The specific twitch force and specific tetanic force are shown in FIG. 26A and FIG. 26B, respectively, for wildtype (circles), mdx untreated (squares) and CRISPR treated (triangles) animals. FIG. 26C shows the eccentric contraction profile for all three animal sets (aster-isk: statistically significant (p<0.05)). Compared to untreated mdx mice, CRISPR therapy significantly improved specific muscle force and enhanced resistance to eccentric contraction-induced force drop.

Figure 27A:
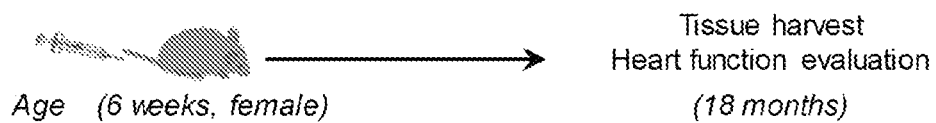
FIG. 27A depicts a schematic overview of a study investigating a long-term systemic AAV CRISPR therapy with a Cas9:gRNA vector ratio of 1:3 in female mdx mice.

Example 3. Long-Term Systemic AAV CRISPR Therapy with a Cas9:gRNA Vector Ratio of 1:3 in Female Mdx Mice In this example, a long-term systemic AAV CRISPR therapy was performed with a Cas9:gRNA vector ratio of 1:3 in female mdx mice. FIG. 27A shows a schematic overview of the study. Eight 6-week-old female mdx mice were co-injected with the Cas9 vector and gRNA vector at the dose of $1 \times 10^{13}$ and $3 \times 10^{13}$ vg/mouse ($6.1 \times 10^{14}$ and $18.2 \times 10^{14}$ vg/kg), respectively. Dystrophin expression, AAV transduction and disease rescue was evaluated at 18 months of the age. Age/sex-matched normal BL10 (wild type, WT) mice and untreated mdx mice were used as controls.

Figure 27B:
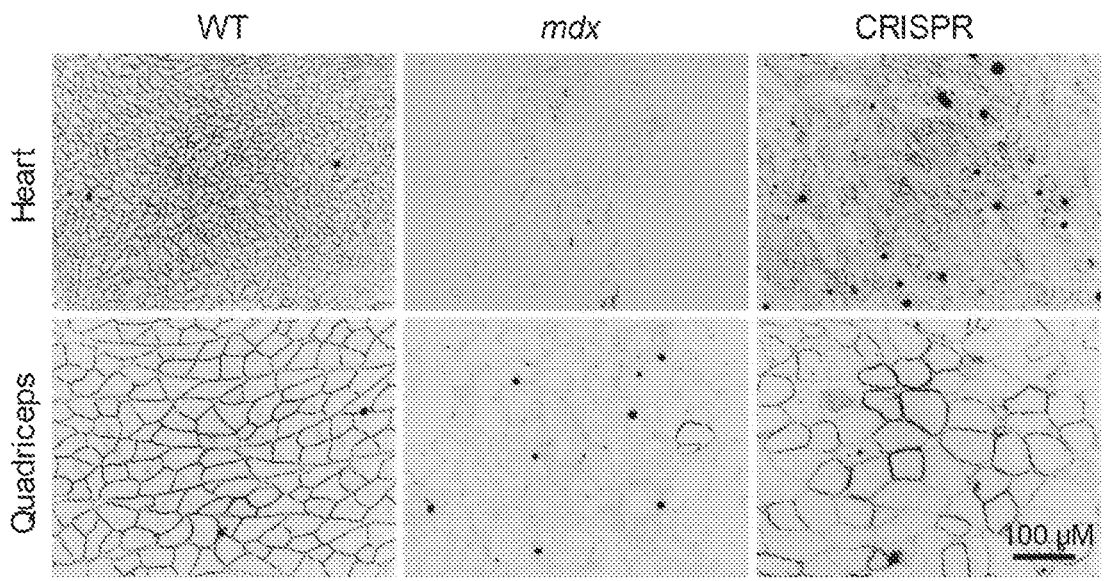
FIG. 27B shows representative dystrophin immunostaining photomicrographs from the heart and quadriceps of mice in the 1:3 female study.
Figure 27C:
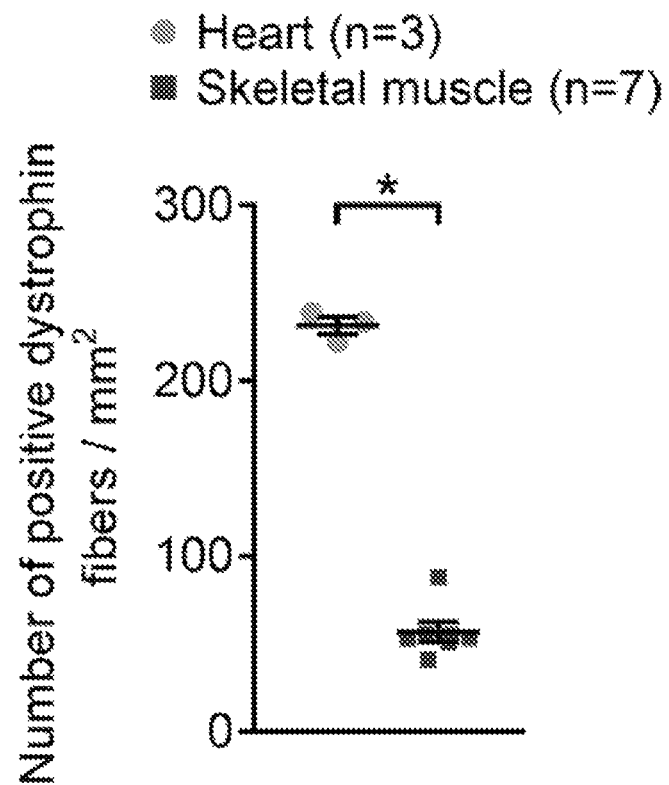
FIG. 27C is a quantification of dystrophin-positive myofibers in immunostained photomicrographs of the heart and skeletal muscle (quadriceps) of mice in the 1:3 female study.
Figure 27D:
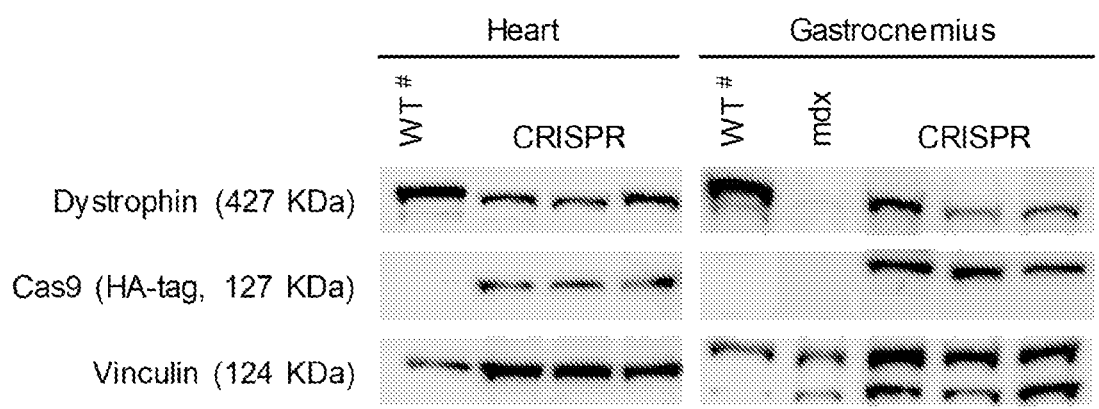
FIG. 27D shows representative dystrophin and Cas9 western blots from the heart and gastrocnemius taken from WT, mdx and treated mdx mice in the 1:3 female study. Vinculin western was included as the loading control. Pound sign (#), loading is different in this lane.
Figure 27E:
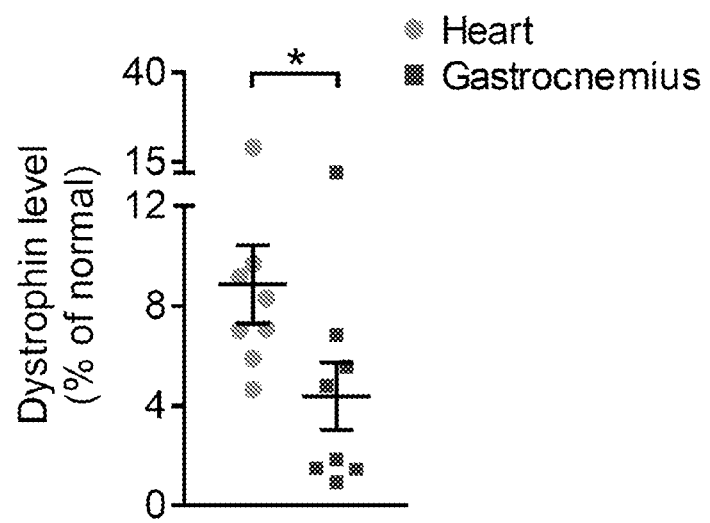
FIG. 27E shows the LICOR quantification of dystrophin western blots of the heart and gastrocnemius from mice in the 1:3 female study. Asterisk (*), statistically significant (p<0.05).

FIG. 27B shows representative dystrophin immunostaining photomicrographs from the heart and quadriceps. Abundant dystrophin positive myocytes were detected in both heart and quadriceps in CRISPR treated mice (FIG. 27C). FIG. 27D shows representative dystrophin and Cas9 western blots from the heart and gastrocnemius. Vinculin western was included as the loading control. Quantification of dystrophin western blot showed approximately 9% expression in the heart and approximately 4% expression in skeletal muscle. These values were significantly greater than those observed in Example 1 (FIGS. 4D and 4E) Dystrophin expression was readily detected in both heart and quadriceps in CRISPR treated mice. FIG. 27E shows LICOR quantification of dystrophin western blot. In panels B-D, an asterisk (*) is used to denote a statistically significant (p<0.05) association and a pound sign (#) indicates that loading was different in this lane (for western blots).

Figure 28A:
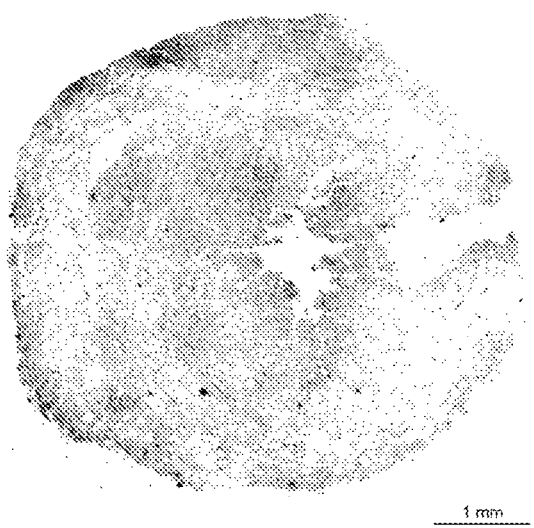
FIG. 28A shows a representative full-view dystrophin immunostaining photomicrographs from the heart of a treated mouse in the female 1:3 study.
Figure 28B:
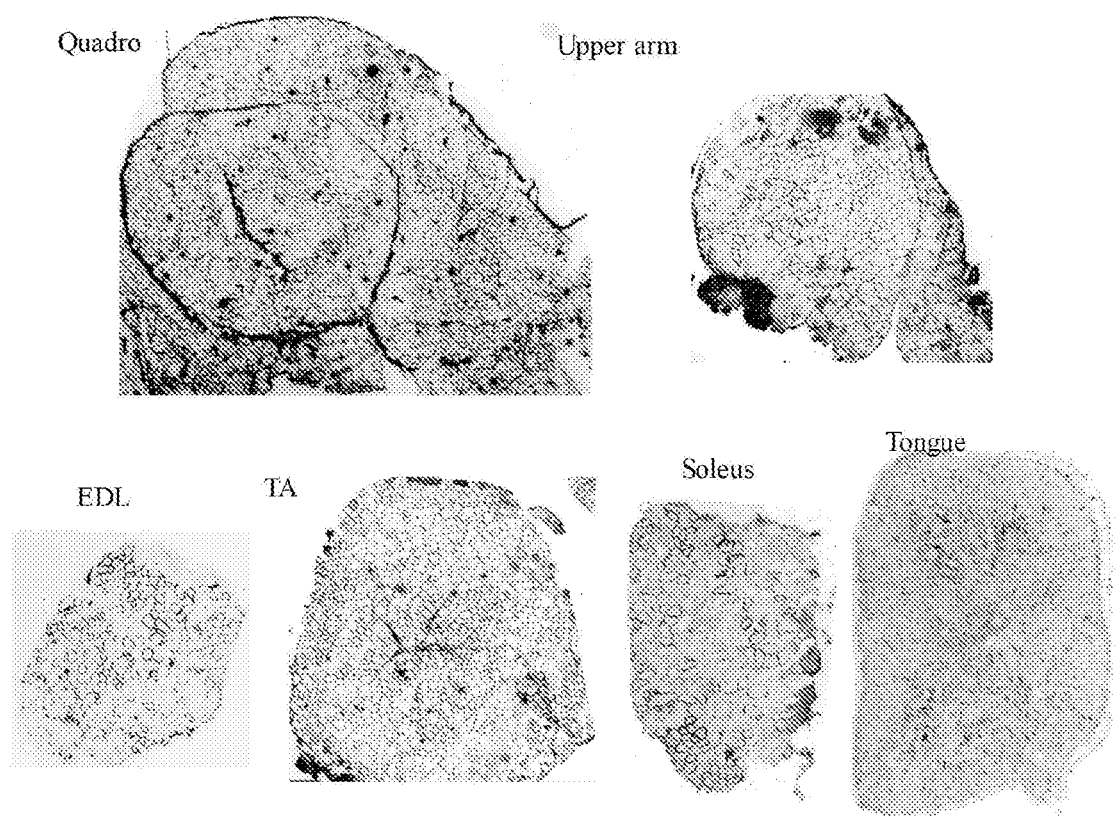
FIG. 28B shows representative full-view dystrophin immunostaining photomicrographs from quadriceps (Quadro), tibialis anterior (TA), extensor digitorum longus (EDL), soleus, upper arm muscle and tongue of a treated mouse in the female 1:3 study.

Similar to Examples 1 and 2 above, levels of bodywide dystrophin restoration was evaluated by immunostaining tissue taken from the heart (FIG. 28A), or from the quadriceps, tibialis anterior (TA), extensor digitorum longus (EDL), soleus, upper arm muscle and tongue (FIG. 28B) of CRISPR treated animals. CRISPR treated animals showed robust expression of dystrophin in all tissues examined.

Figure 29:
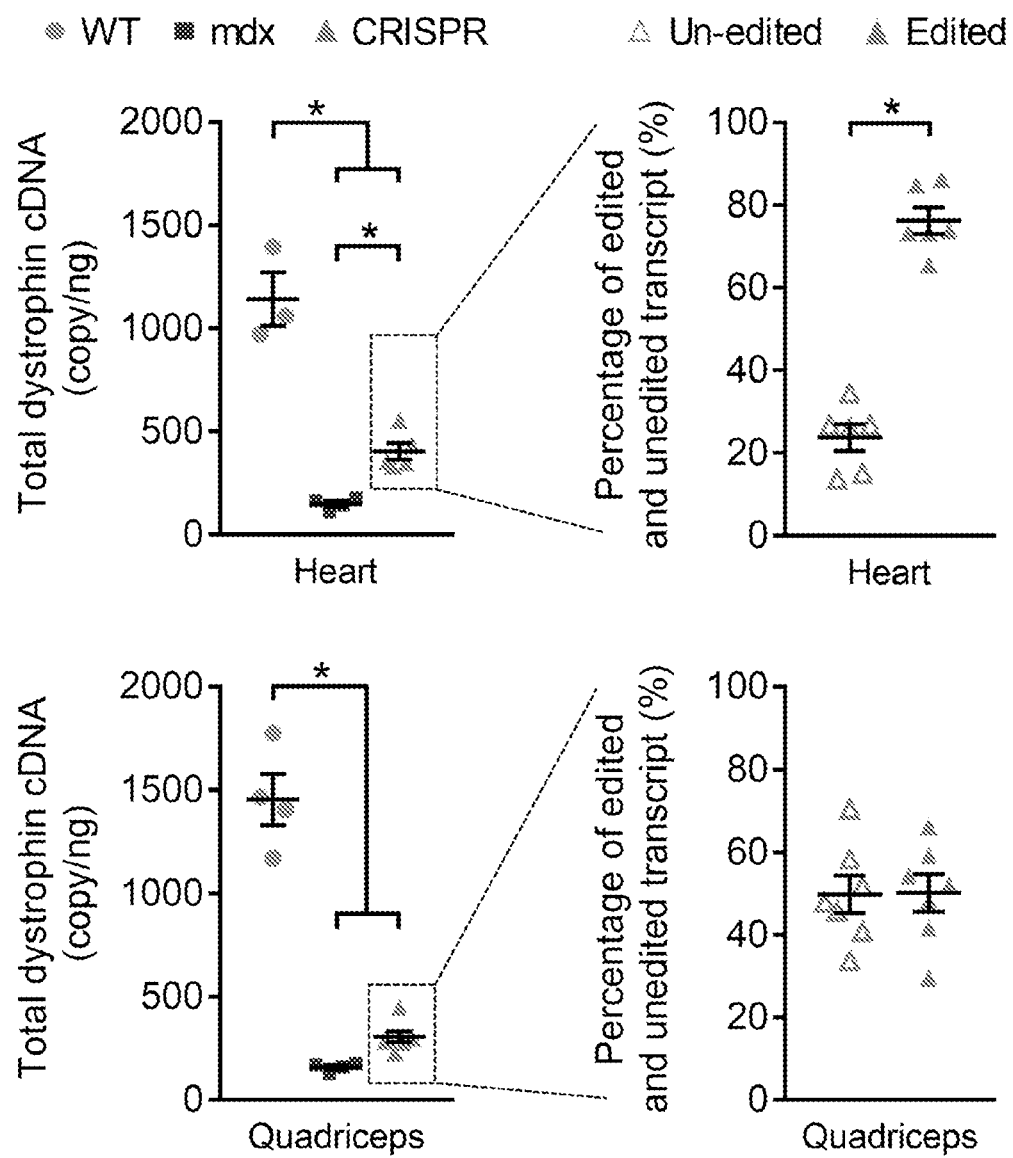
FIG. 29 shows the quantification of the dystrophin transcript in the heart (top panels) and quadriceps (bottom panels) by droplet digital PCR in the female 1:3 study. Left panels depict total dystrophin transcript levels per ng of cDNA. Right panels depict the percentage of unedited and edited dystrophin transcripts in CRISPR treated mdx mice. Asterisk, statistically significant (p<0.05).

FIG. 29 shows the quantification of the dystrophin transcript in the heart (top panels) and quadriceps (bottom panels) by droplet digital PCR. Left panels depict total dystrophin transcript levels per ng of cDNA. Right panels depict the percentage of unedited and edited dystrophin transcripts in CRISPR treated mdx mice. In the heart of CRISPR treated mdx mice, the level of total dystrophin transcripts was significantly higher than that of mdx mice but lower than that of wild type mice. Furthermore, the percentage of edited transcripts was significantly higher than that of unedited transcripts (approximately 80% total edited). In the quadriceps of CRISPR treated mdx mice, the level of total dystrophin transcripts was higher than that of mdx mice but the difference did not reach statistical significance. Edited transcripts accounted for about half of the total dystrophin transcripts but did not reach statistical significance. Asterisk, statistically significant (p<0.05).

Figure 30A:
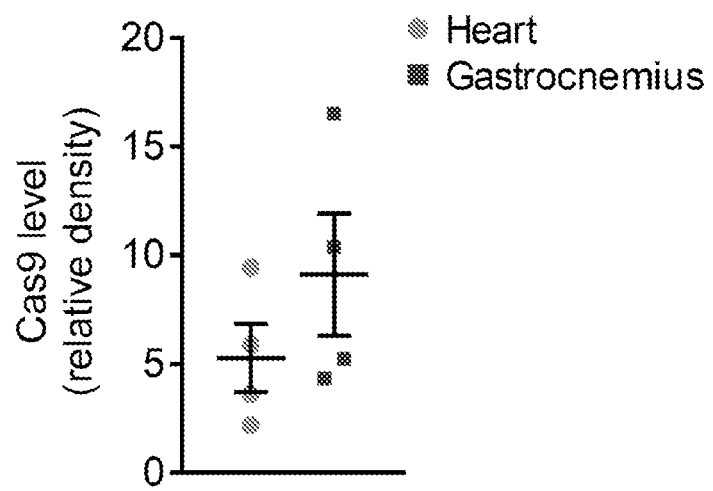
FIG. 30A depicts levels of Cas9 expression in the female 1:3 study via western blot measurement for the Cas9 protein.
Figure 30B:
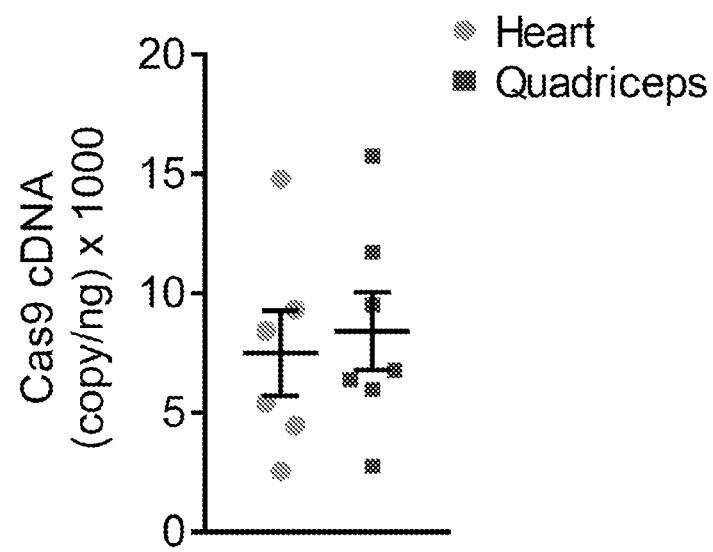
FIG. 30B depicts levels of Cas9 expression in the female 1:3 study digital droplet PCR measurements of the Cas9 transcript.

FIG. 30A and FIG. 30B show the quantitative evaluation of Cas9 in the heart, gastrocnemius and quadriceps in this study. FIG. 30A shows similar levels of Cas9 protein as measured by western blot in the heart and gastrocnemius and FIG. 30B shows similar levels of Cas9 transcript as measured by digital droplet PCR in the heart and quadriceps. Thus, similar levels of Cas9 was achieved across tissue types in this study.

Figure 31A:
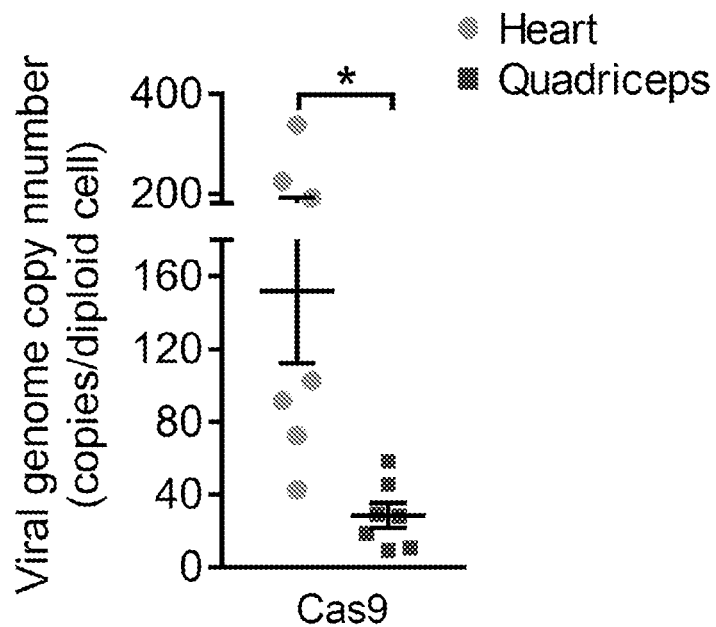
FIG. 31A quantifies the Cas9 vector genome copy number by TaqMan PCR in the female 1:3 study. Asterisk, statistically significant (p<0.05).
Figure 31B:
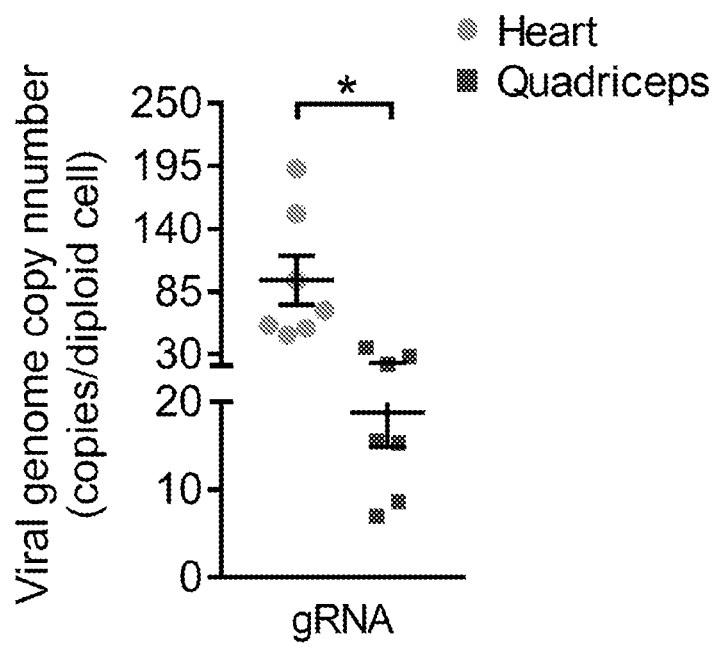
FIG. 31B quantifies the gRNA vector genome copy number by TaqMan PCR in the female 1:3 study. Asterisk, statistically significant (p<0.05).
Figure 32:
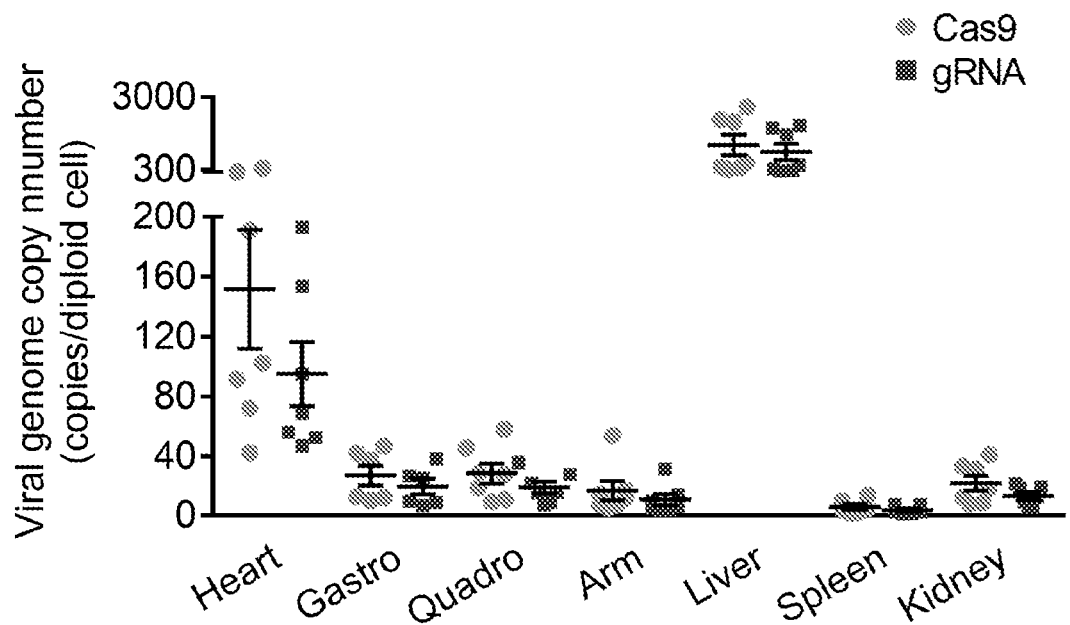
FIG. 32 is a scatter plot comparing the Cas9 and gRNA vector genome copy number in different tissues in the female 1:3 study.
Figure 33:
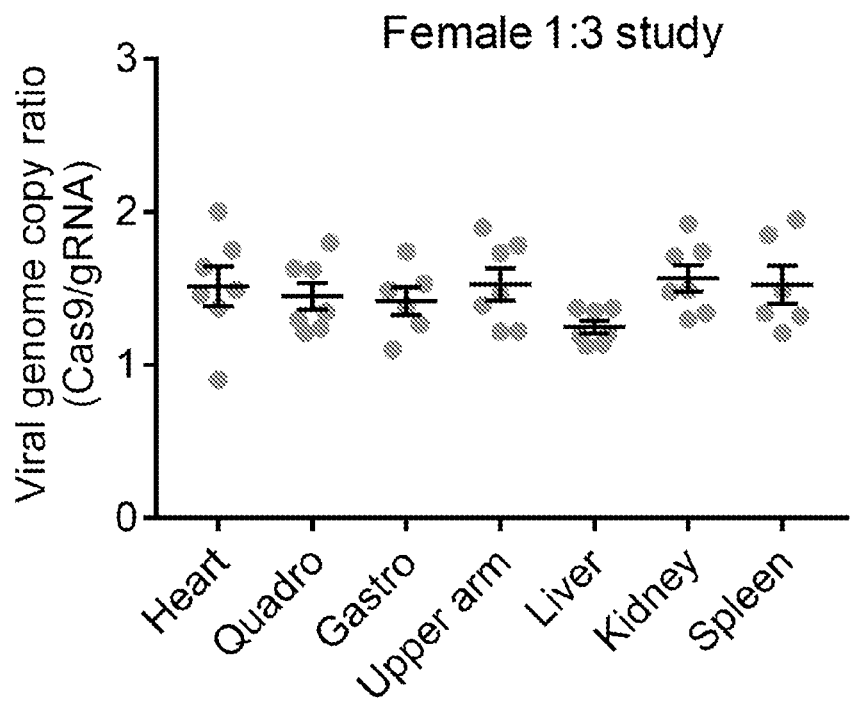
FIG. 33 depicts viral genome copy number ratios (Cas9/gRNA) in the female 3:1 study.

AAV genome copy numbers were then quantitatively evaluated using TaqMan PCR for both the Cas9 vector and the gRNA vector in various tissues taken from treated animals. Results are shown in FIG. 31A (for Cas9 vector in heart and quadriceps), FIG. 31B (for gRNA vector in heart and quadriceps) and FIG. 32 (Cas9 and gRNA copy numbers across the heart, gastrocnemius, quadriceps, arm muscle, liver, spleen and kidney). For both Cas9 and gRNA vectors, the viral genome copy in the heart was significantly higher than that in the quadriceps (FIGS. 31A and 31B). Despite the fact that the Cas9 vector genome copy number in that heart was significantly higher than that of the quadriceps, the two tissues showed similar levels of Cas9 expression at the RNA level and protein level (see FIG. 30A-30B). Since the potency of the CMV promoter varies in different types of tissues and cells (Qin et al PLOS One 5:e10611, 2010), it is very likely that the CMV promoter was stronger in the quadriceps than it was in the heart in the context of our study. Asterisk, statistically significant ($p < 0.05$). Similar levels of the Cas9 vector and the gRNA vector genome copy numbers were detected in all other tissues examined (FIG. 32). Further, the ratio of the Cas9 vector to gRNA vector was close to 1 in all tissues examined (FIG. 33).

Figure 34:
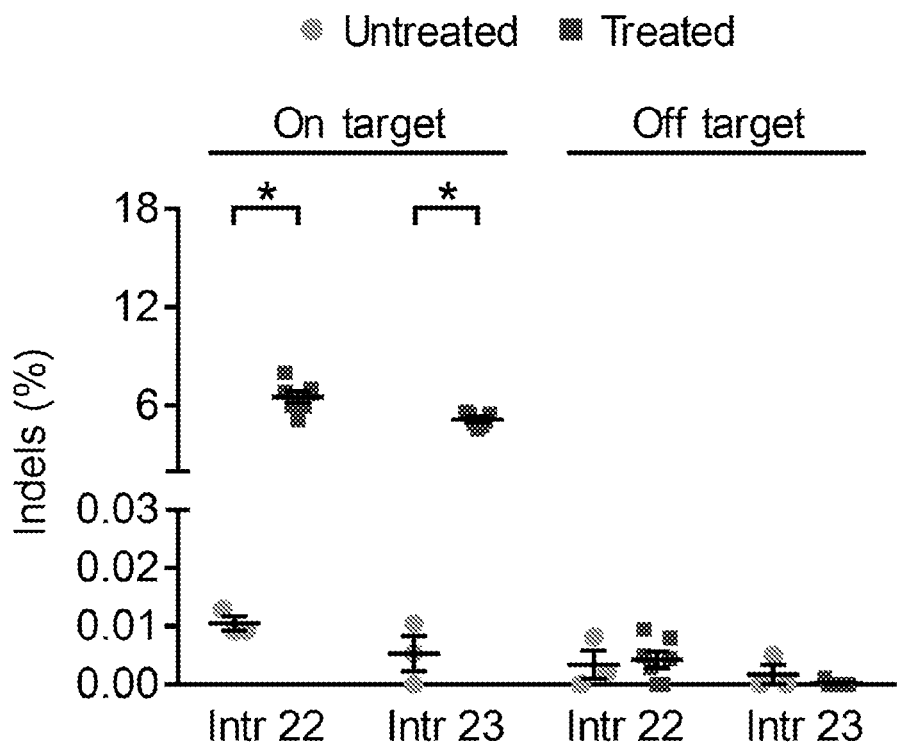
FIG. 34 depicts indels at on-target and off-target sites in untreated and treated CRISPR mdx mice, quantified by deep sequencing in the female 1:3 study. Asterisk, statistically significant (p<0.05).

To quantify insertions/deletions (indels) in CRISPR treated mdx mice, deep sequencing was performed at both on target and predicted off-target sites was performed in both untreated and CRISPR treated mdx mice. As shown in FIG. 34, significant on-target editing was observed for both gRNAs only in CRISPR treated mdx mice. Off-target editing was not detected with either gRNA. Asterisk, statistically significant ($p < 0.05$).

Table10, below, depicts anatomic properties (e.g., BW, body weight; HW, heart weight; TW, tibialis muscle weight; VW, ventricle weight) for the mice in this study.

TABLE 10

| N | WT 20 | mdx 20 | CRISPR 8 |
|---|---|---|---|
| Age (m) | 18.2 ± 0.44 | 18.74 ± 0.45 | 18.53 ± 0.07 |
| BW (g) | 30.2 ± 0.91 † | 22.36 ± 0.39 | 22.43 ± 0.88 |

TABLE 10-continued

| N | WT 20 | mdx 20 | CRISPR 8 |
|---|---|---|---|
| HW (mg) | 115.8 ± 1.99 † | 108 ± 1.76 | 99.20 ± 3.99 |
| VW (mg) | 109.9 ± 1.88 † | 102 ± 1.62 | 95.23 ± 3.60 |
| TL (mm) | 18.64 ± 0.08 | 18.6 ± 0.05 | 18.54 ± 0.13 |
| TW (mg) | 38.51 ± 0.70 | 42.78 ± 2.18 | 46.89 ± 0.56* |
| HW/BW (mg/g) | 3.88 ± 0.10 † | 4.8 ± 0.07 | 4.44 ± 0.15 |
| HW/TL (mg/mm) | 6.3 ± 0.13 † | 5.73 ± 0.08 | 5.35 ± 0.20 |
| HW/TW (mg/g) | 3.1 ± 0.06 † | 2.61 ± 0.15 | 2.12 ± 0.098 # |
| VW/BW (mg/g) | 3.69 ± 0.10 † | 4.54 ± 0.07 | 4.27 ± 0.14 |
| VW/TL (mg/mm) | 5.99 ± 0.12 † | 5.44 ± 0.08 | 5.13 ± 0.18 |
| VW/TW (mg/g) | 2.86 ± 0.05 † | 2.4 ± 0.12 | 2.04 ± 0.09 |

Figure 35A:
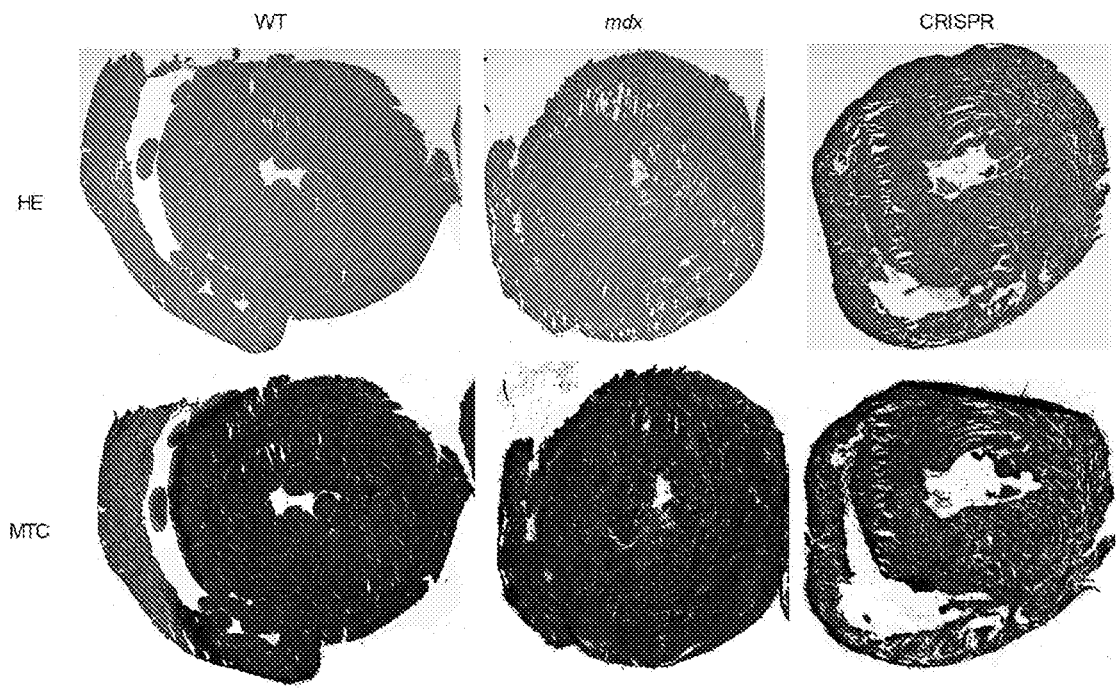
FIG. 35A shows representative high-magnification photomicrographs showing heart histology by hematoxylin and eosin (HE) and Masson trichome (MTC) staining from each study group in the female 1:3 study
Figure 35B:
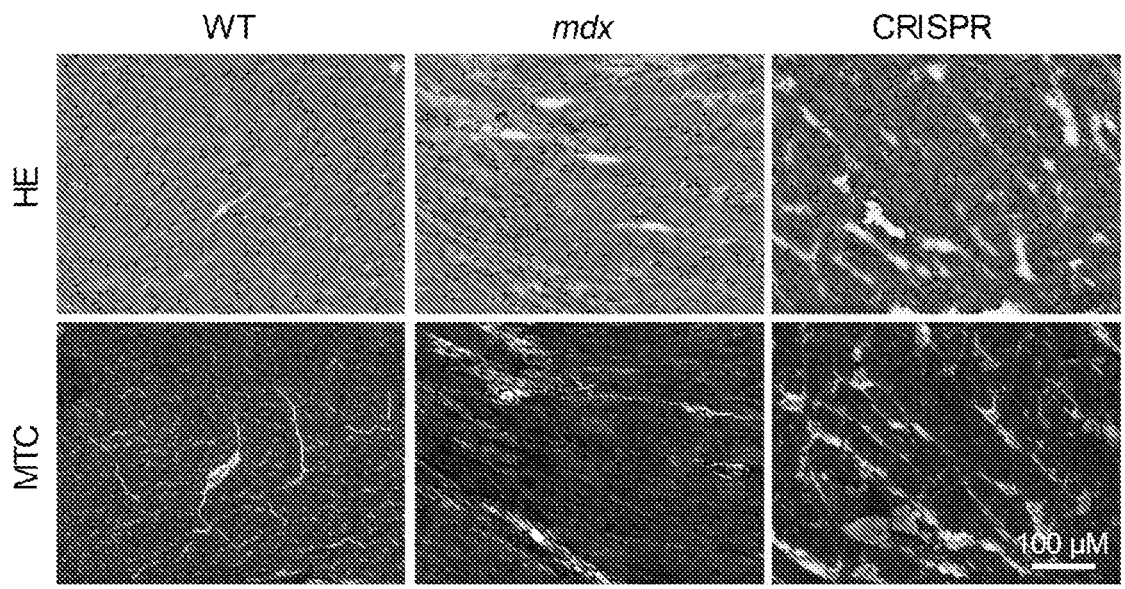
FIG. 35B shows representative full-view photomicrographs showing heart histology by hematoxylin and eosin (HE) and Masson trichome (MTC) staining from each study group in the female 1:3 study.
Figure 35C:
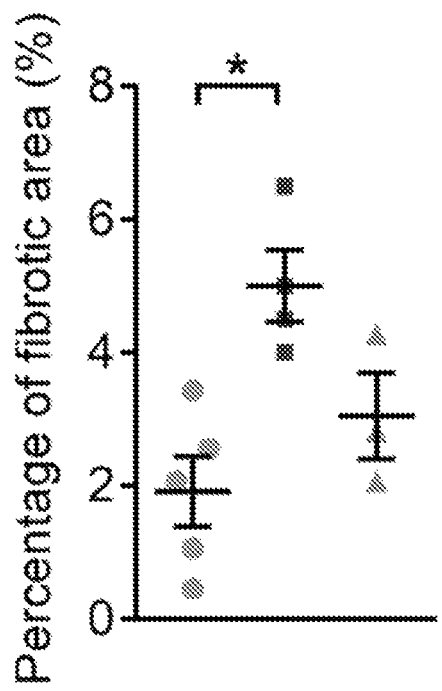
FIG. 35C is a quantification of fibrosis in the heart of animals in the female 1:3 study.

*Significantly different from WT
†, Significantly different from mdx and CRISPR
, Significantly different from mdx The histology and function of the heart was evaluated in each study group. Heart histology was evaluated by hematoxylin and eosin (HE) and Masson trichrome (MTC) staining in each group. FIG. 35A shows representative high-magnification photomicrographs and FIG. 35B shows representative full-view photomicrographs of each study group. Myocardial fibrosis was greatly reduced in CRISPR treated mice (FIG. 35C).

Figure 36A:
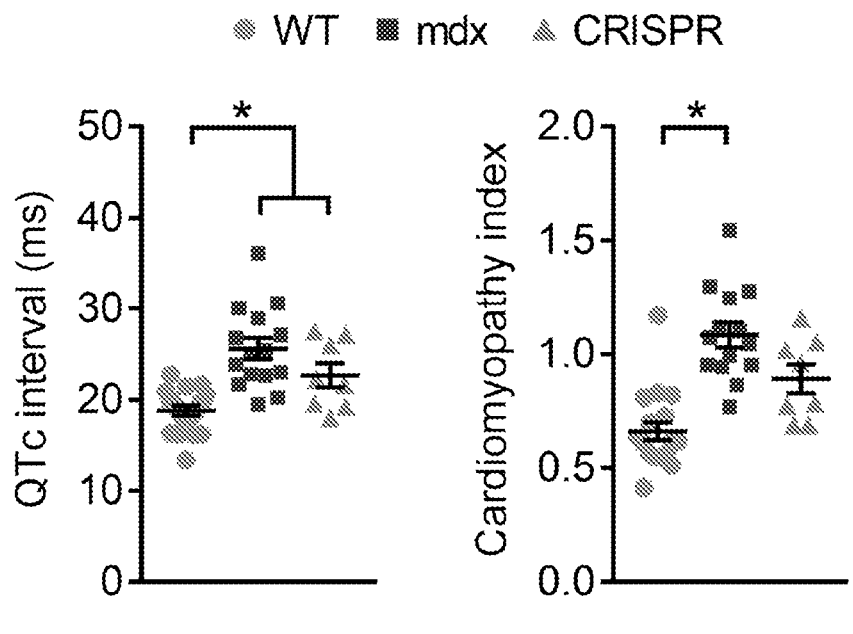
FIG. 36A shows a quantitative evaluation of Mitchell corrected QT (QTc) interval and cardiomyopathy index in the female 1:3 study. Asterisk, statistically significant (p<0.05).
Figure 36B:
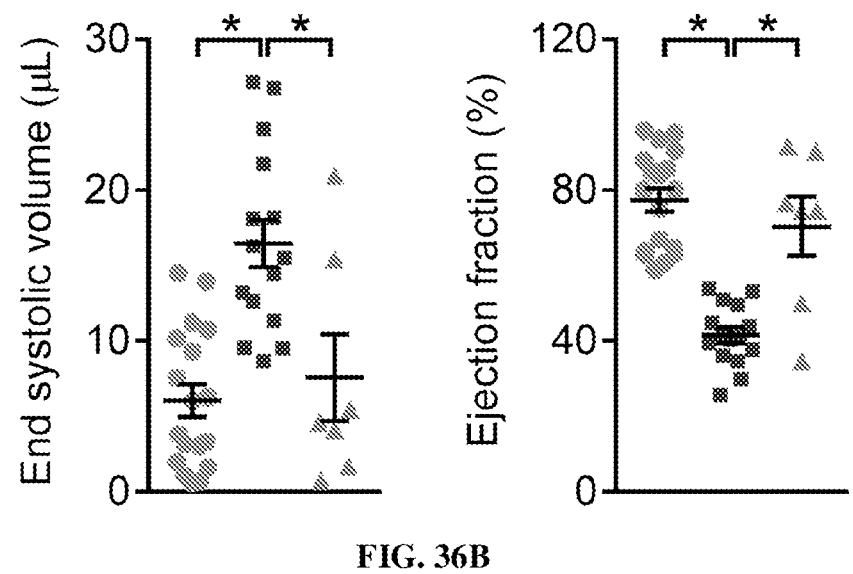
FIG. 36B shows a quantitative evaluation of the end systolic volume and ejection fraction in the female 1:3 study. Asterisk, statistically significant (p<0.05).

To evaluate heart function, a quantitative evaluation of selected ECG and hemodynamic parameters was performed on the study groups. FIG. 36A shows Mitchell corrected QT (QTc) interval and cardiomyopathy index. FIG. 36B shows end systolic volume and ejection fraction. The QTc interval and cardiomyopathy index were improved in CRISPR treated mice but the difference did not reach statistical significance. However, CRISPR therapy significantly improved the end systolic volume and ejection fraction. Asterisk, statistically significant ($p < 0.05$). Additional results are shown below for ECG evaluation of heart rate, PR interval, QRS duration and Q amplitude (Table 11) and for quantitative evaluation of heart hemodynamics by the closed chest cardiac cassette assay (Table 12). Although not statistically significant, improvements were seen in all indicated ECG and hemodynamic parameters in CRISPR treated mdx mice.

TABLE 11

| Strain | N | Age | Heart Rate | PR Interval | QRS Duration | Q amplitude (μV) |
|---|---|---|---|---|---|---|
| WT | 18 | 18.36 ± 0.55 | 557.74 ± 16.22 | 40.96 ± 0.80 | 8.68 ± 0.23 | −29.27 ± 5.58 |
| mdx | 15 | 18.87 ± 0.48 | 615.00 ± 14.78* | 33.73 ± 0.80* | 10.17 ± 0.34* | −96.15 ± 18.18* |
| CRISPR | 8 | 18.28 ± 0.04 | 586.45 ± 9.05 | 36.85 ± 1.13 | 9.54 ± 0.59 | −47.25 ± 14.55 |

*Significantly different from WT

TABLE 12

| N | WT 18 | Mdx 15 | CRISPR 7 |
|---|---|---|---|
| Age | 17.99 ± 0.41 | 18.82 ± 0.49 | 18.29 ± 0.04 |
| End diastolic vol. (μL) | 20.90 ± 1.72 | 23.27 ± 1.90 | 19.91 ± 2.90 |
| Max pressure (mmHg) | 101.73 ± 1.44 # | 86.47 ± 5.00 | 91.50 ± 2.57 |
| Stroke Volume (μL) | 16.96 ± 1.12 | 10.17 ± 0.61* | 12.95 ± 1.12 |

TABLE 12-continued

| N | WT 18 | Mdx 15 | CRISPR 7 |
|---|---|---|---|
| Cardiac output (mL/min) | 10218.58 ± 651.91 | 6002.17 ± 327.11* | 7462.68 ± 725.59 |
| dP/dt max (KmmHg/sec) | 13571.17 ± 541.32 | 10402.07 ± 958.94* | 11047.29 ± 1036.77 |
| dP/dt min (KmmHg/sec) | | −9414.93 ± 821.74* | −11363.86 ± 894.92 |
| Tau (ms) | 7.48 ± 0.55 | 8.42 ± 0.36 | 6.87 ± 0.47 |

*Significantly different from WT
, Significantly different from mdx and CRISPR

Figure 37A:
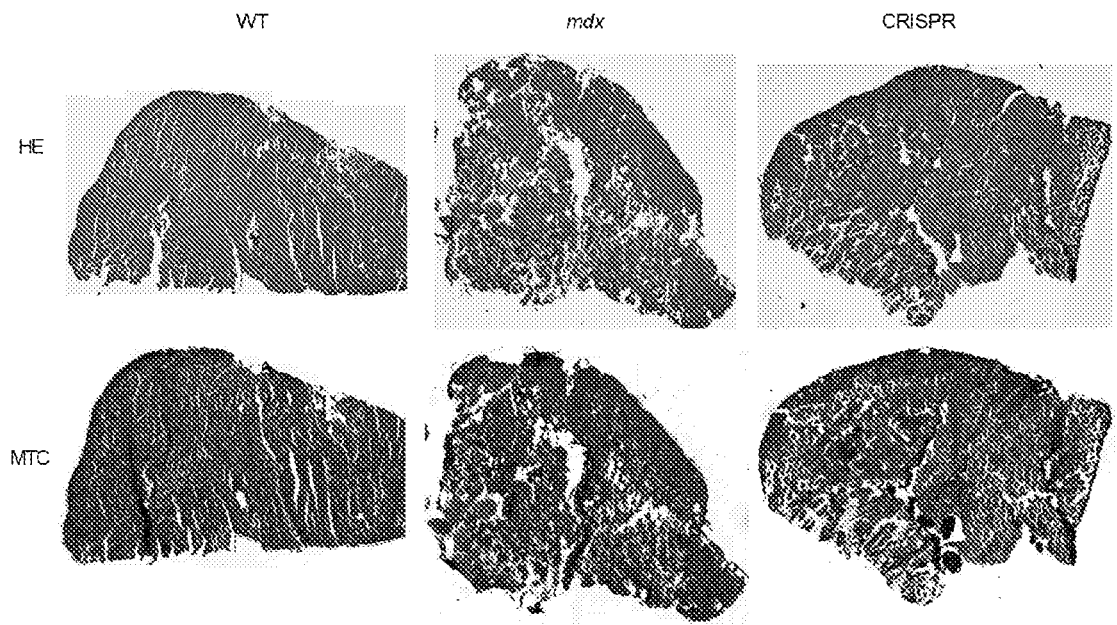
FIG. 37A depicts representative full-view photomicrographs of skeletal muscle histology by hematoxylin and eosin (HE) and Masson trichrome (MTC) staining in the female 1:3 study.
Figure 37B:
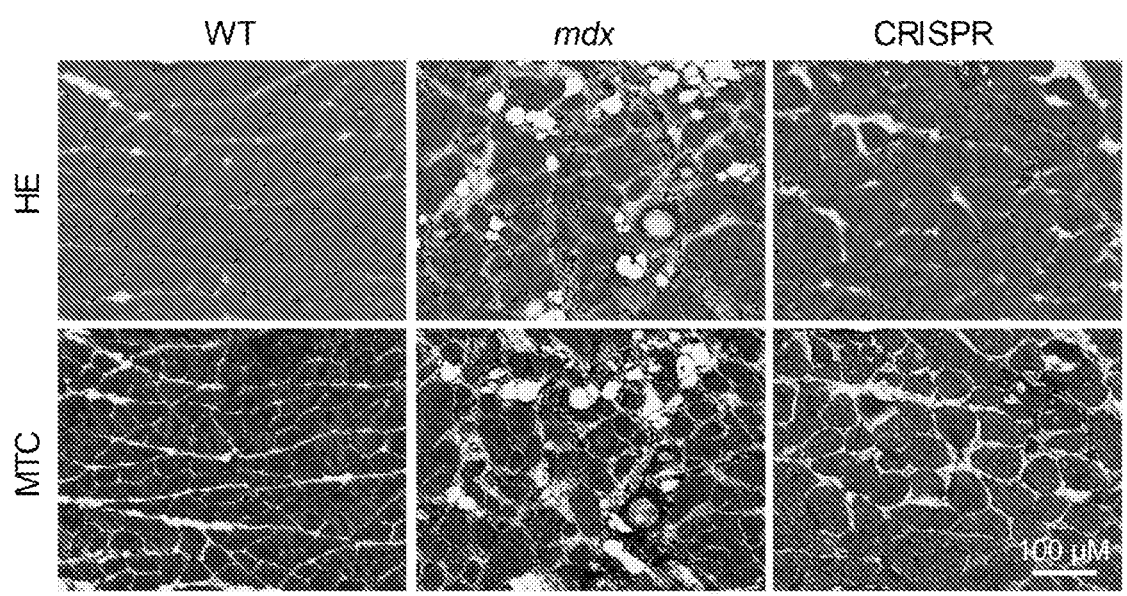
FIG. 37B depicts representative high magnification view photomicrographs of skeletal muscle histology by hematoxylin and eosin (HE) and Masson trichrome (MTC) staining in the female 1:3 study.

Skeletal muscle histology was also measured in the study groups using hematoxylin and eosin (HE) and Masson trichrome (MTC) staining. FIG. 37A shows representative full-view photomicrographs and FIG. 37B shows representative high magnification view photomicrographs of tissue taken from the study groups. CRISPR treatment greatly attenuated muscle fibrosis.

Example 4: Comparison Between 3 Studies

Figure 38A:
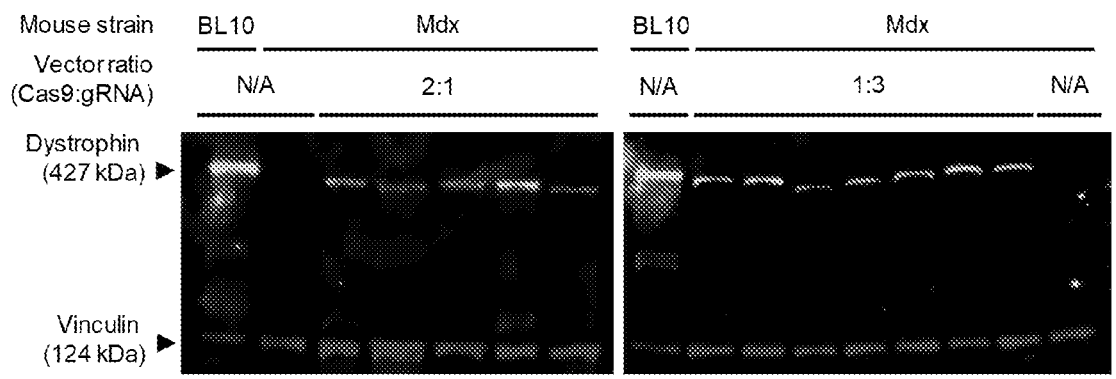
FIG. 38A. Quantification of dystrophin restoration in the heart by two-color western blot for the 2:1 study and the female 1:3 study. Left panel. Results from all five CRISPR treated mice in the 2:1 study. Right panel. Results from seven CRISPR treated mice in the female 1:3 study.
Figure 38B:
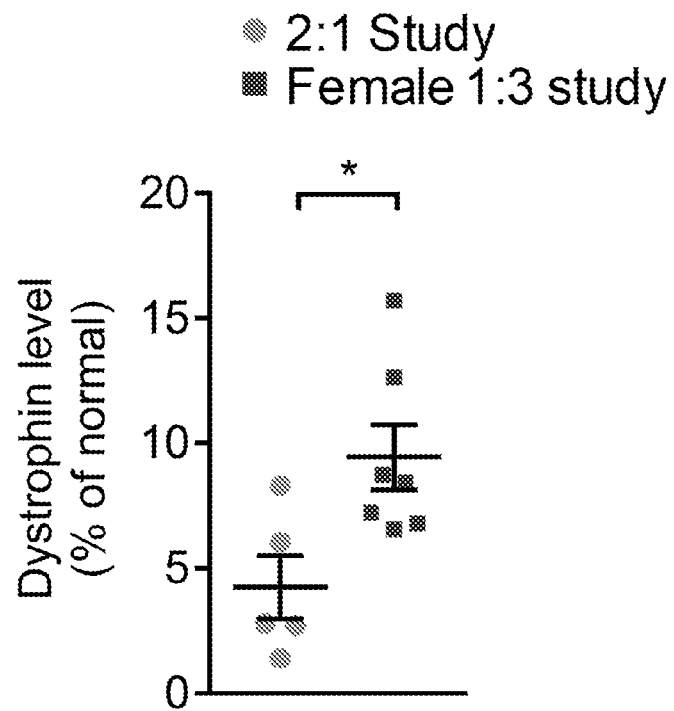
FIG. 38B shows the quantification results from the two color western blot for the 2:1 study and the female 1:3 study. Asterisk, statistically significant (p<0.05).

In this example, results from the studies described in Examples 1 and 3 are compared. A two-color western blot was performed to validate chemiluminescent western blot results shown in FIGS. 4 and 27 for the mouse 2:1 study (Example 1) and the female 3:1 study (Example 3). Briefly, to validate chemiluminescent western blot results, heart lysates were re-electrophoresed in a separated gel and evaluated using the LICOR two-color infrared fluorescence detection method. Heart lysates from BL10 and mdx mice were included as positive and negative controls, respectively. The loading of the BL10 lane was one-fourth of the other lanes. FIG. 38A, left panel, shows results from all five CRISPR treated mice in the 2:1 study. FIG. 38A, right panel, shows results from seven CRISPR treated mice in the female 1:3 study. FIG. 38B shows the quantification of dystrophin protein levels across these two studies. The dystrophin levels obtained using the infrared fluorescence detection method were similar to those obtained using the chemiluminescent detection method in FIGS. 4 and 27. Further, the dystrophin levels were significantly higher in the female 3:1 study compared to the 2:1 study (asterisk, statistically significant ($p<0.05$)).

Example 5: Local Delivery of Viral Vectors

Given the unexpected observation of gRNA vector depletion in systematically treated mice, a study was designed to test the effect of the vector ratio on local (i.e., intramuscular) CRISPR therapy. Table 13 summarizes the vector ratio (Cas9:gRNA) and vector doses (vg/muscle) delivered to 2 month old male mdx mice (sample size of 4-6 mice). The indicated amount of the Cas9 and gRNA vectors were delivered to the tibialis anterior muscle of mdx mice in a volume of 50 μL/muscle.

TABLE 13

| Vector ratio (Cas9:gRNA) | n | Cas9 Vector (vg/muscle) | gRNA Vector (vg/muscle) |
|---|---|---|---|
| Un-injected | 6 | 0 | 0 |
| (0:1) | 4 | 0 | 1.00E+11 |
| (1:0) | 4 | 1.00E+11 | 0 |
| (1:1) | 4 | 1.00E+11 | 1.00E+11 |
| (1:2) | 4 | 1.00E+11 | 2.00E+11 |
| (1:3) | 4 | 1.00E+11 | 3.00E+11 |
| (2:1) | 4 | 2.00E+11 | 1.00E+11 |

Figure 39A:
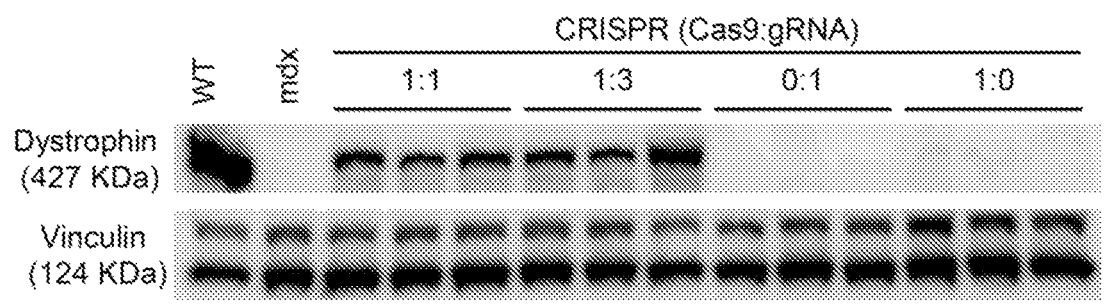
FIG. 39A shows a representative dystrophin western blot measuring dystrophin expression in mice locally injected with the indicated ratios of Cas9 to gRNA: 1:0 ($1 \times 10^{11}$ vg Cas9 only), 0:1 ($1 \times 10^{11}$ vg gRNA only), 1:1 ($1 \times 10^{11}$ vg Cas9 and $1 \times 10^{11}$ vg gRNA) or 1:3 ($1 \times 10^{11}$ vg Cas9 and $3 \times 10^{11}$ vg gRNA). Tissue was evaluated at 3 months.
Figure 39B:
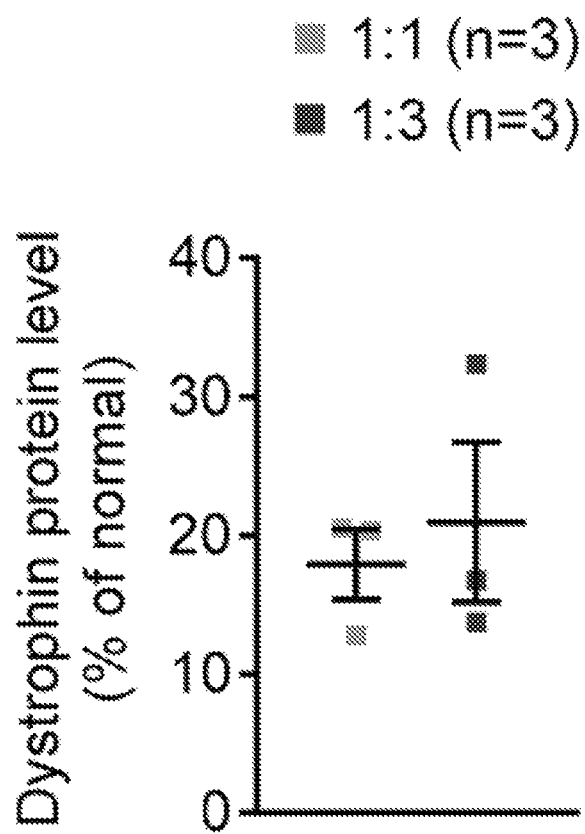
FIG. 39B shows the quantification of dystrophin protein level in tissue (tibalis anterior muscle) obtained from mice locally injected with a 1:1 ($1 \times 10^{11}$ vg Cas9 and $1 \times 10^{11}$ vg gRNA) or 1:3 ratio ($1 \times 10^{11}$ vg Cas9 and $3 \times 10^{11}$ vg gRNA) of Cas9:gRNA.
Figure 40A:
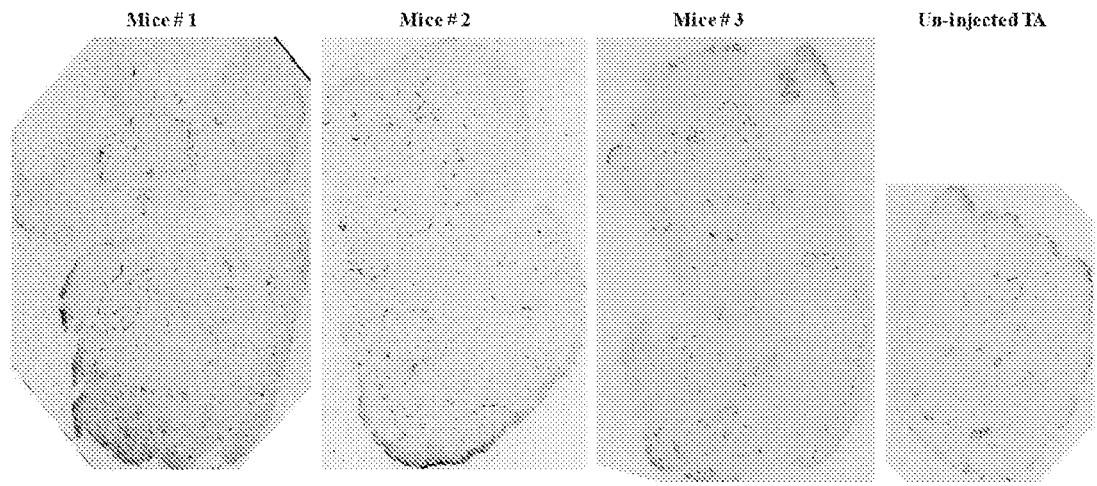
FIG. 40A depicts representative full-view photomicrographs of dystrophin immunostaining from three independent CRISPR treated muscles and one untreated muscle from a group treated in the local 0:1 (Cas9 vector:gRNA vector) study.
Figure 40B:
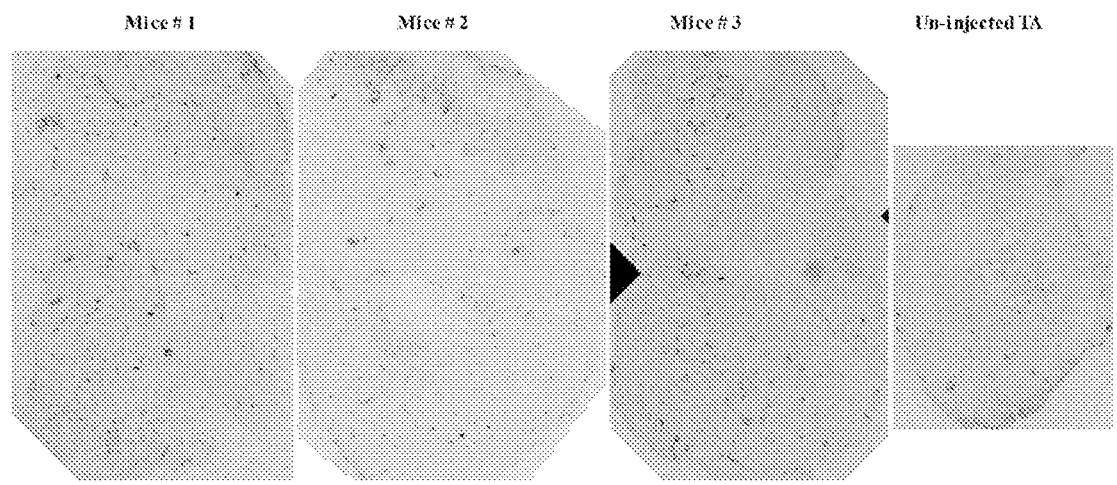
FIG. 40B depicts representative full-view photomicrographs of dystrophin immunostaining from three independent CRISPR treated muscles and one untreated muscle from a group treated in the local 1:0 (Cas9 vector:gRNA vector) study.
Figure 40C:
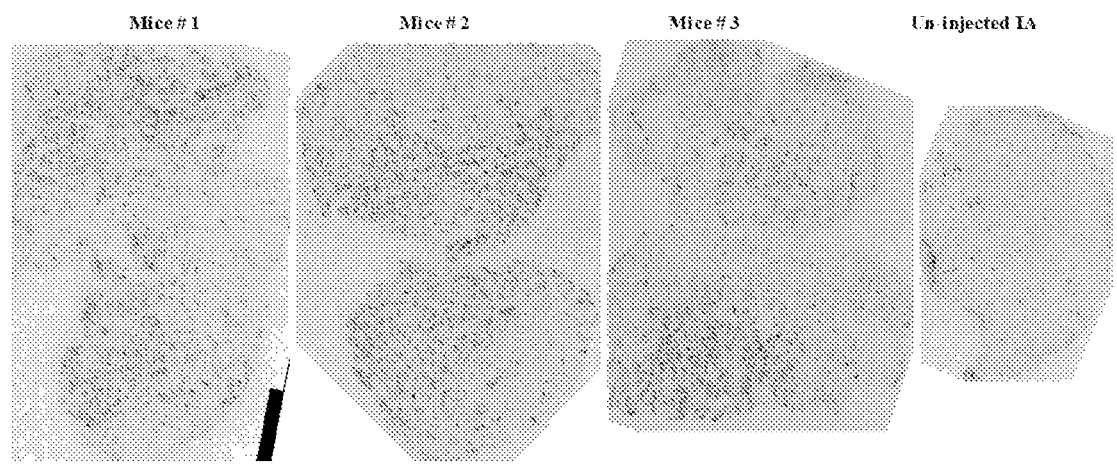
FIG. 40C depicts representative full-view photomicrographs of dystrophin immunostaining from three independent CRISPR treated muscles and one untreated muscle from a group treated in the local 1:1 (Cas9 vector:gRNA vector) study.
Figure 40D:
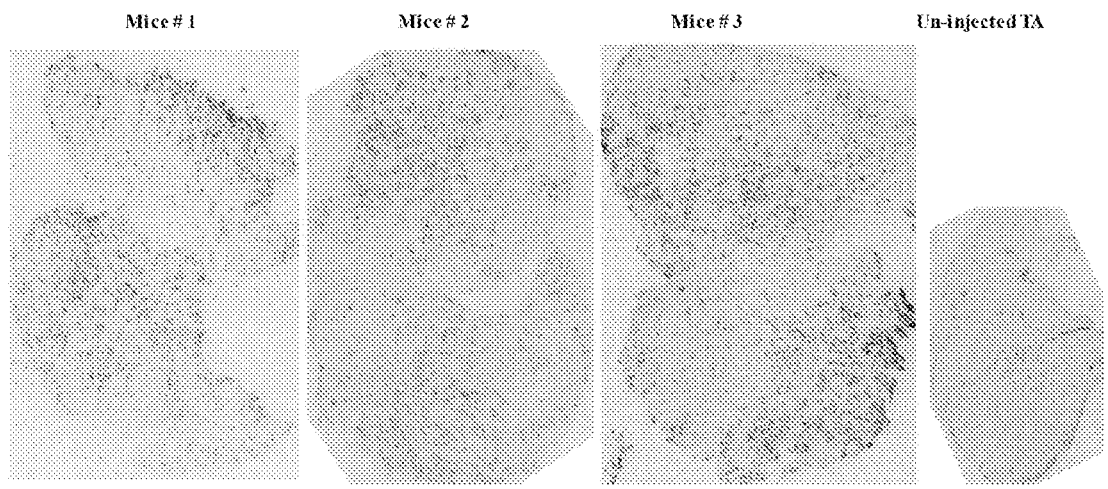
FIG. 40D depicts representative full-view photomicrographs of dystrophin immunostaining from three independent CRISPR treated muscles and one untreated muscle from a group treated in the local 1:2 (Cas9 vector:gRNA vector) study.
Figure 40E:
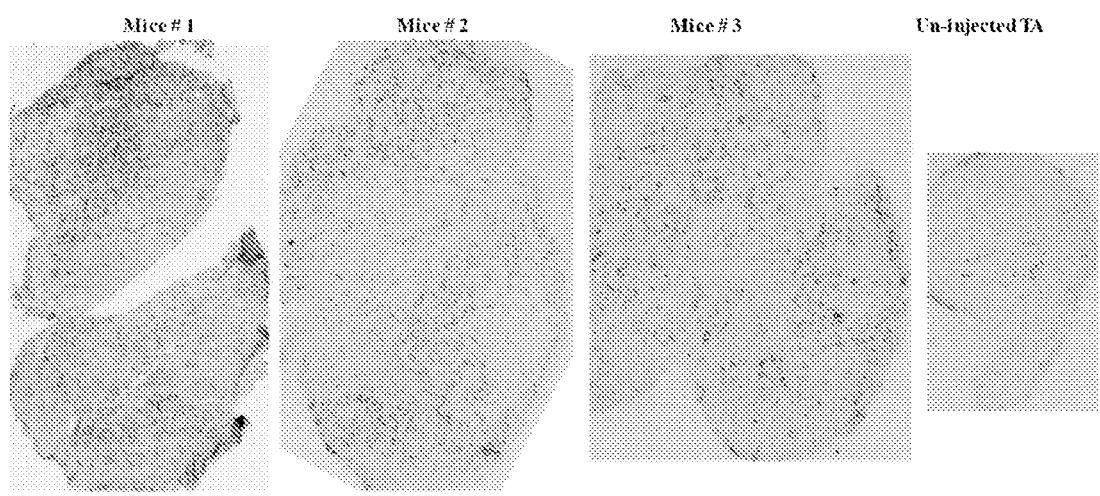
FIG. 40E depicts representative full-view photomicrographs of dystrophin immunostaining from three independent CRISPR treated muscles and one untreated muscle from a group treated in the local 1:3 (Cas9 vector:gRNA vector) study.
Figure 40F:
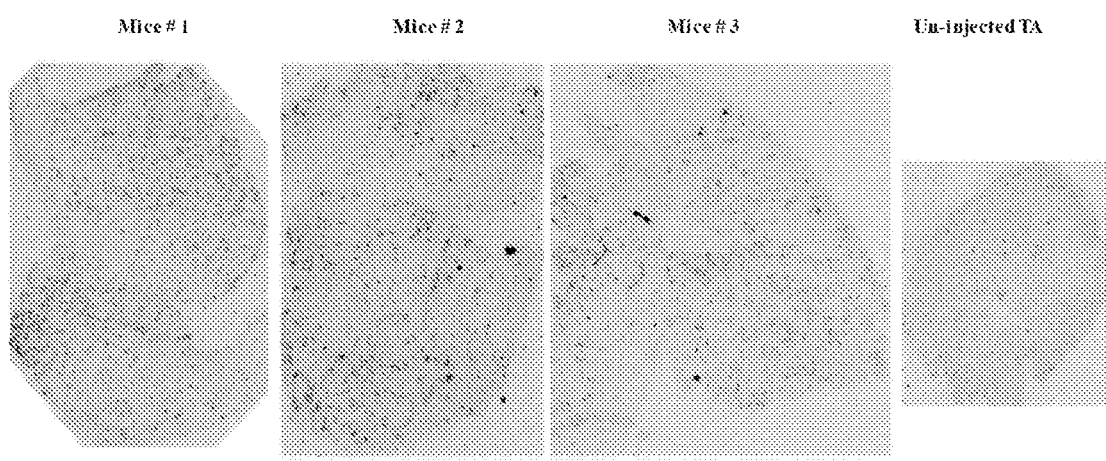
FIG. 40F depicts representative full-view photomicrographs of dystrophin immunostaining from three independent CRISPR treated muscles and one untreated muscle from a group treated in the local 2:1 (Cas9 vector:gRNA vector) study.

Surprisingly, increasing the Cas9-to-gRNA vector ratio from 1:1 to 1:3 did not enhance dystrophin expression (FIG. 39A-39B). As done in Examples 1-3 above, dystrophin expression in CRISPR treated animals was evaluated by immunostaining and compared to untreated animals. FIGS. 40A-40F show representative full-view photomicrographs of dystrophin immunostaining from three independent CRISPR treated muscles and one untreated muscle in each group. FIG. 40A shows images from the local 0:1 (Cas9 vector:gRNA vector) study. FIG. 40B shows images from the local 1:0 (Cas9 vector:gRNA vector) study. FIG. 40C shows images from the local 1:1 (Cas9 vector:gRNA vector) study. FIG. 40D shows images from the local 1:2 (Cas9 vector:gRNA vector) study. FIG. 40E shows images from the local 1:3 (Cas9 vector:gRNA vector) study. FIG. 40F shows images from the local 2:1 (Cas9 vector:gRNA vector) study.

Figure 41:
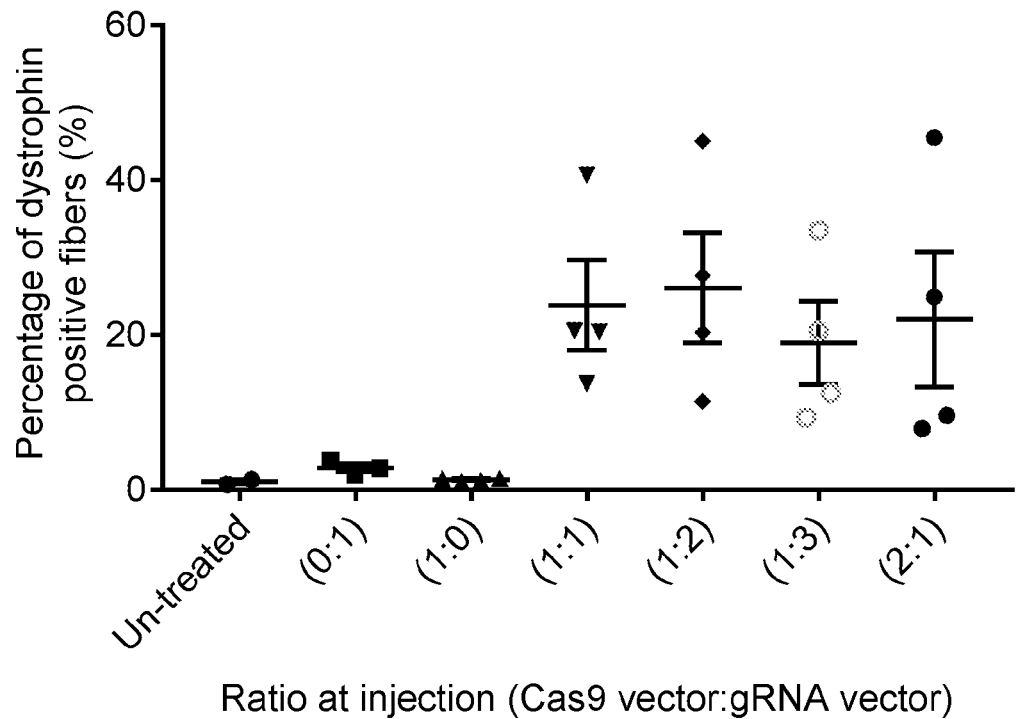
FIG. 41 is a scatter plot indicating the percent dystrophin positive fibers detected in the different local ratios studies (AAV vectors delivered locally via an intramuscular injection).

The percentage of dystrophin positive cells were quantified in untreated mdx mice and mdx mice treated with the ratios described in Table 13 above and results are shown in FIG. 41. Only nominal dystrophin positive myofibers were detected in untreated mdx mice, and mdx mice treated with only the gRNA vector (0:1) or only the Cas9 vector (1:0). Similar levels of dystrophin positive myofibers were detected in mice that received both Cas9 and gRNA vectors. Surprisingly, increasing the Cas9-to-gRNA vector ratio from 1:1 to 1:3 did not enhance dystrophin expression. No significant difference was detected among different ratios (1:1, 1:2, 1:3, or 2:1).

Figure 42:
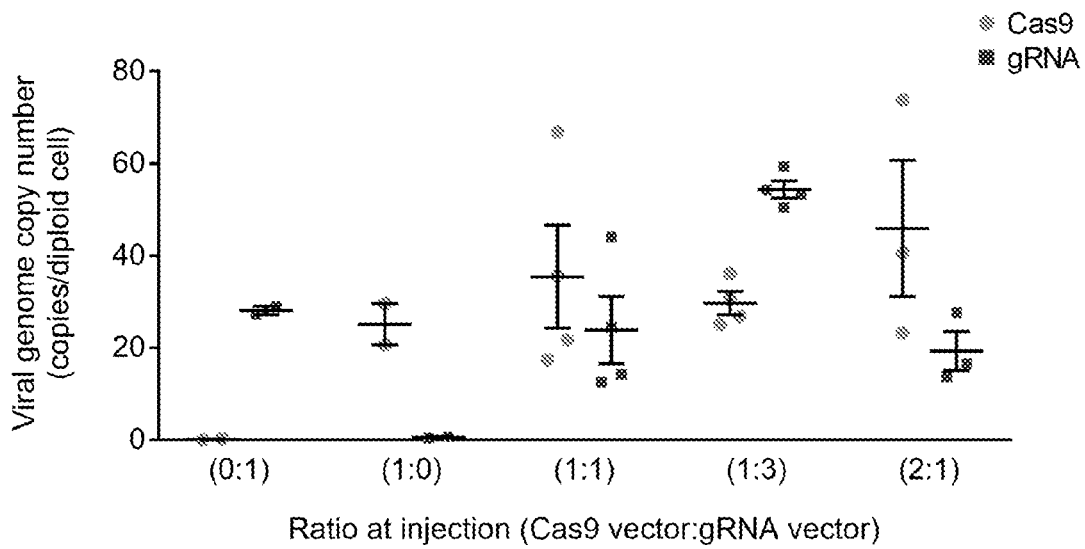
FIG. 42 is a scatter plot indicating the viral genome copy number across the groups in the local ratio study.
Figure 43:
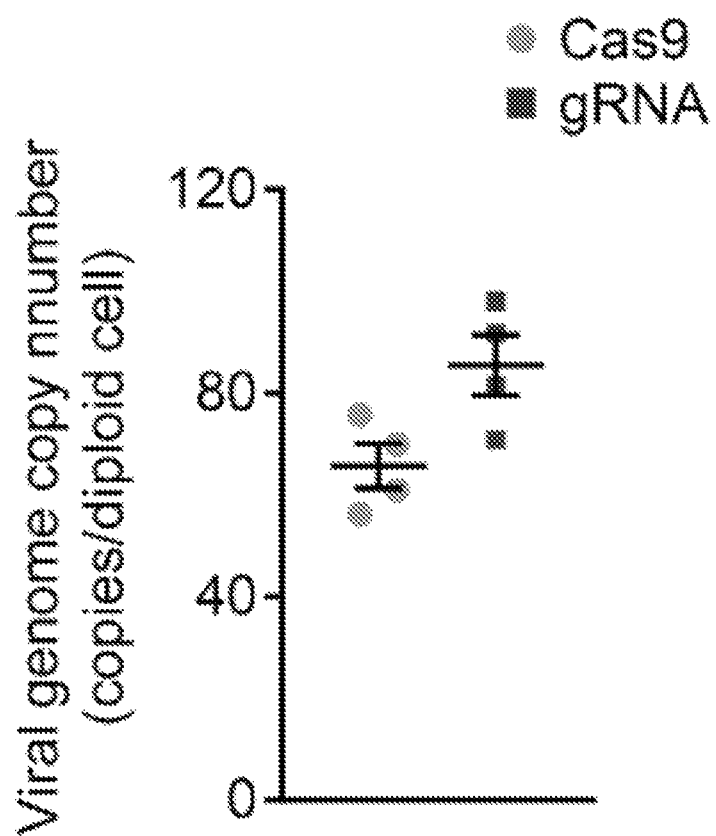
FIG. 43 is a scatter plot depicting viral genome copy number of Cas9 and gRNA vectors in treated animals from a previously published local administration study (Nelson et al., 2015).

The AAV genome copy number for Cas9 and gRNA vectors was determined in the local ratio study (FIG. 42). For mice that received single vector injection, only respective vector genome was detected. For mice treated with the 1:1 ratio (Cas9 vector:gRNA vector), approximately equal amount of viral genome copies were detected for each vector. For mice treated with the 1:3 ratio (Cas9 vector:gRNA vector), approximately two-fold more gRNA viral genome copies were detected. For mice treated with the 2:1 ratio (Cas9 vector:gRNA vector), approximately two-fold more Cas9 viral genome copies were detected. Thus, similar to the dystrophin expression, there was no observed preferential gRNA vector loss in this local study. The Cas9 to gRNA vector genome ratio in harvested muscle was proportional to that at injection. To further validate these results, we quantified the AAV genome copy number in muscles harvested from previously published local injection studies (Nelson et al., 2016). Similarly, there was no evidence of selective gRNA vector depletion (FIG. 43).

Together, these examples demonstrate that preferential gRNA vector depletion is a unique feature of systemic AAV CRISPR therapy that may be rectified by increased dosing of the gRNA vector relative to the Cas9 vector.

REFERENCES

1. Long C, et al. Postnatal genome editing partially restores dystrophin expression in a mouse model of muscular dystrophy. Science. 2016; 351(6271):400-403.
2. Nelson C E, et al. In vivo genome editing improves muscle function in a mouse model of Duchenne muscular dystrophy. Science. 2016; 351(6271):403-407.
3. Tabebordbar M, et al. In vivo gene editing in dystrophic mouse muscle and muscle stem cells. Science. 2016; 351(6271):407-411.
4. Ousterout D G, Kabadi A M, Thakore P I, Majoros W H, Reddy T E, Gersbach C A. Multiplex CRISPR/Cas9-based genome editing for correction of dystrophin mutations that cause Duchenne muscular dystrophy. Nat Commun. 2015; 6:6244.
5. Wojtal D, et al. Spell Checking Nature: Versatility of CRISPR/Cas9 for developing treatments for inherited disorders. Am J Hum Genet. 2016; 98(1):90-101.
6. Xu L, et al. CRISPR-mediated genome editing restores dystrophin expression and function in mdx mice. Mol Ther. 2016; 24(3):564-569.
7. Bengtsson N E, et al. Muscle-specific CRISPR/Cas9 dystrophin gene editing ameliorates pathophysiology in a mouse model for Duchenne muscular dystrophy. Nat Commun. 2017; 8:14454.
8. Young C S, et al. A single CRISPR-Cas9 deletion strategy that targets the majority of DMD patients restores dystrophin function in hiPSC-derived muscle cells. Cell Stem Cell. 2016; 18(4):533-540.
9. Zhang Y, et al. CRISPR-Cpf1 correction of muscular dystrophy mutations in human cardiomyocytes and mice. Set Adv. 2017; 3(4):e1602814.
10. El Refaey M, et al. In vivo genome editing restores dystrophin expression and cardiac function in dystrophic mice. Circ Res. 2017; 121(8):923-929.
11. Amoasii L, et al. Single-cut genome editing restores dystrophin expression in a new mouse model of muscular dystrophy. Sci Transl Med. 2017; 9(418).
12. Sicinski P, Geng Y, Ryder-Cook A S, Barnard E A, Darlison M G, Barnard P J. The molecular basis of muscular dystrophy in the mdx mouse: a point mutation. Science. 1989; 244(4912):1578-1580.
13. Hakim C H, et al. A five-repeat micro-dystrophin gene ameliorated dystrophic phenotype in the severe DBA/2J-mdx model of Duchenne muscular dystrophy. Mol Ther Methods Clin Dev. 2017; 6:216-230.
14. Duan D. Systemic delivery of adeno-associated viral vectors. Curr Opin Virol. 2016; 21:16-25.
15. Inagaki K, et al. Robust systemic transduction with AAV9 vectors in mice: efficient global cardiac gene transfer superior to that of AAV8. Mol Ther. 2006; 14(1): 45-53.
16. Zincarelli C, Soltys S, Rengo G, Rabinowitz J E. Analysis of AAV serotypes 1-9 mediated gene expression and tropism in mice after systemic injection. Mol Ther. 2008; 16(6):1073-1080.
17. Ghosh A, Yue Y, Shin J H, Duan D. Systemic Trans-splicing adeno-associated viral delivery efficiently transduces the heart of adult mdx mouse, a model for Duchenne muscular dystrophy. Hum Gene Ther. 2009; 20(11): 1319-1328.
18. Cox D B, Platt R J, Zhang F. Therapeutic genome editing: prospects and challenges. Nat Med. 2015; 21(2): 121-131.
19. Zhang Y, Long C, Bassel-Duby R, Olson E N. Myoediting: Toward prevention of muscular dystrophy by therapeutic genome editing. Physiol Rev. 2018; 98(3): 1205-1240.
20. Nelson C E, Robinson-Hamm I N, Gersbach C A. Genome engineering: a new approach to gene therapy for neuromuscular disorders. Nat Rev Neurol. 2017; 13(11): 647-661.
21. Ishizaki M, Kobayashi M, Adachi K, Matsumura T, Kimura E. Female dystrophinopathy: Review of current literature. Neuromuscul Disord. 2018; 28(7):572-581.
22. Hakim C H, Duan D. Gender differences in contractile and passive properties of mdx extensor digitorum longus muscle. Muscle Nerve. 2012; 45(2):250-256.
23. Bostick B, Yue Y, Duan D. Gender influences cardiac function in the mdx model of Duchenne cardiomyopathy. Muscle Nerve. 2010; 42(4):600-603.
24. Kerr T P, Sewry C A, Robb S A, Roberts R G. Long mutant dystrophins and variable phenotypes: evasion of nonsense-mediated decay? Hum Genet. 2001; 109(4): 402-407.
25. Qin J Y, et al. Systematic comparison of constitutive promoters and the doxycycline-inducible promoter. PLoS One. 2010; 5(5):e10611.
26. Varani G. Exceptionally stable nucleic acid hairpins. Annu Rev Biophys Biomol Struct. 1995; 24:379-404.
27. Hakim C H, Li D, Duan D. Monitoring murine skeletal muscle function for muscle gene therapy. Methods Mol Biol. 2011; 709:75-89.
28. Hakim C H, Wasala N B, Duan D. Evaluation of muscle function of the extensor digitorum longus muscle ex vivo and tibialis anterior muscle in situ in mice. J Vis Exp. 2013; (72):e50183.
29. Bostick B, Yue Y, Duan D. Phenotyping cardiac gene therapy in mice. Methods Mol Biol. 2011; 709:91-104.
30. Shin J H, Yue Y, Duan D. Recombinant adeno-associated viral vector production and purification. Methods Mol Biol. 2012; 798:267-284.
31. N B, Shin J H, Lai Y, Yue Y, Montanaro F, Duan D. Cardiac-specific expression of ΔH2-R15 mini-dystrophin normalized all electrocardiogram abnormalities and the end-diastolic volume in a 23-month-old mouse model of Duchenne dilated cardiomyopathy. Hum Gene Ther. 2018; 29(7):737-748.
32. Pinello L, et al. Analyzing CRISPR genome-editing experiments with CRISPResso. Nat Biotechnol. 2016; 34(7):695-697.
33. Mendez J, Keys A. Density and composition of mammalian muscle. Metabolism. 1960; 9(2):184-188.
34. Burkholder T J, Fingado B, Baron S, Lieber R L. Relationship between muscle fiber types and sizes and muscle architectural properties in the mouse hindlimb. J Morphol. 1994; 221(2):177-190.
35. Brooks S V, Faulkner J A. Contractile properties of skeletal muscles from young, adult and aged mice. J Physiol (Lond). 1988; 404:71-82.
36. Bostick B, Shin J H, Yue Y, Duan D. AAV-microdystrophin therapy improves cardiac performance in aged female mdx mice. Mol Ther. 2011; 19(10):1826-1832.
37. Wasala N B, Bostick B, Yue Y, Duan D. Exclusive skeletal muscle correction does not modulate dystrophic heart disease in the aged mdx model of Duchenne cardiomyopathy. *Hum Mol Genet.* 2013; 22(13):2634-2641.
38. Mitchell G F, Jeron A, Koren G. Measurement of heart rate and Q-T interval in the conscious mouse. *Am J Physiol.* 1998; 274(3 Pt 2):H747-H751
39. Nigro G, Comi L I, Politano L. Electrocardiographic evaluation of the P-type stage of dystrophic cardiomyopathy. *Cardiomyology.* 1984; 3:45-58.
40. Duan D, et al. Standard operating procedures (SOPs) for evaluating the heart in preclinical studies of Duchenne muscular dystrophy. *J Cardiovasc Transl Res.* 2016; 9(1): 85-86.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

We claim:

1. A method for systemically editing a gene in a subject, the method comprising:
   administering to the subject via systemic delivery:
   (a) a gene editing adeno-associated virus (AAV) vector comprising a CRISPR associated system (Cas) gene under control of regulatory sequences which direct its expression in a target cell of the subject; and
   (b) a targeting AAV vector providing at least one guide ribonucleic acid (gRNA) targeted to the gene; and
   wherein, the ratio of the targeting AAV vector to the gene editing AAV vector is greater than or equal to 2:1 and wherein administering the mixture of the gene editing AAV and targeting AAV vector edits the gene by inducing a double stranded break (DSB) in the gene that is repaired using non-homologous end joining (NHEJ).

2. The method of claim 1 further comprising systemically treating a genetic disorder in the subject, wherein the genetic disorder is caused by a mutation in the gene targeted by the gene editing AAV vector and targeting AAV.

3. The method of claim 1 wherein the gene comprises a frame shift mutation.

4. The method of claim 3 wherein the frameshift mutation results in the loss of an open reading frame and the method further comprises restoring the open reading frame in the gene.

5. The method of claim 3 wherein the frameshift mutation results in a premature stop codon and the method comprises deleting a portion of the target gene comprising the premature stop codon.

6. The method of claim 5, wherein the portion of the target gene comprising the premature stop codon comprises an exon.

7. The method of claim 3 wherein the frameshift mutation causes alternative splicing of the gene and the method comprises inducing an insertion or deletion in the gene to restore normal splicing of the gene.

8. The method of claim 7 wherein the method comprises modifying at least one of: a splicing signal, an exonic splicing enhancer/silencer (ESE/ESS), or an intronic splicing enhancer/silencer (ISE/ISS).

9. The method of claim 1 wherein the mixture does not comprise a donor nucleic acid.

10. The method of claim 2 wherein the genetic disorder is caused by loss of expression of a protein or expression of a truncated non-functional protein.

11. The method of claim 2 wherein the genetic disorder is selected from the group consisting of an inherited muscle disease, a lysosomal storage disease, a heritable disorder of connective tissue, a neurodegenerative disorder, and a skeletal dysplasia.

12. The method of claim 2 wherein the genetic disorder is selected from the group consisting of Duchenne muscular dystrophy or Becker muscular dystrophy.

13. The method of claim 1 wherein the targeting AAV vector further comprises one or more promoter sequences that drive gRNA expression and/or at least one gRNA.

14. The method of claim 1 wherein the gene editing AAV vector further comprises a ubiquitous or tissue-specific promoter, and/or a polyadenylation signal.

15. The method of claim 1 wherein the Cas gene encodes a Cas protein selected from the group consisting of: type I Cas, type II Cas, type III Cas, type IV Cas, and type V Cas.

16. The method of claim 15 wherein the Cas protein is Cas9 or Cas12.

17. The method of claim 1 wherein the ratio of the targeting AAV vector to the gene editing vector is from about 2:1 to about 10:1.

18. The method of claim 1 wherein the ratio of the targeting AAV vector to the gene editing AAV vector is about 3:1.

19. The method of claim 1 wherein the subject is a mouse or a human.

\* \* \* \* \*